United States Patent
Blanden et al.

(10) Patent No.: US 11,414,454 B2
(45) Date of Patent: Aug. 16, 2022

(54) COMPOSITIONS, METHODS, AND SYSTEMS FOR AFFINITY-BASED PROTEIN IDENTIFICATION AND PURIFICATION

(71) Applicant: Auctus Biologies, Inc., Lafayette, NY (US)

(72) Inventors: Adam Blanden, Manlius, NY (US); Aaron Wolfe, Syracuse, NY (US)

(73) Assignee: Auctus Biologies, Inc., Lafayette, NY (US)

( * ) Notice: Subject to any disclaimer, the term of this patent is extended or adjusted under 35 U.S.C. 154(b) by 209 days.

(21) Appl. No.: 16/492,038

(22) PCT Filed: Mar. 7, 2018

(86) PCT No.: PCT/US2018/021385
§ 371 (c)(1),
(2) Date: Sep. 6, 2019

(87) PCT Pub. No.: WO2018/165328
PCT Pub. Date: Sep. 13, 2018

(65) Prior Publication Data
US 2020/0102347 A1    Apr. 2, 2020

Related U.S. Application Data

(60) Provisional application No. 62/627,349, filed on Feb. 7, 2018, provisional application No. 62/559,143, filed on Sep. 15, 2017, provisional application No. 62/468,323, filed on Mar. 7, 2017.

(51) Int. Cl.
| | | |
|---|---|---|
| *C07K 14/245* | (2006.01) | |
| *C07K 14/49* | (2006.01) | |
| *C12N 15/62* | (2006.01) | |
| *G01N 33/566* | (2006.01) | |
| *G01N 33/68* | (2006.01) | |
| *C07K 1/22* | (2006.01) | |

(52) U.S. Cl.
CPC .............. *C07K 1/22* (2013.01); *C07K 14/245* (2013.01); *C07K 14/49* (2013.01); *C12N 15/62* (2013.01); *G01N 33/566* (2013.01); *G01N 33/68* (2013.01); *C07K 2319/40* (2013.01); *C07K 2319/61* (2013.01); *C07K 2319/75* (2013.01)

(58) Field of Classification Search
CPC ...... C12N 15/62; G01N 33/566; G01N 33/68; C07K 2319/40; C07K 2319/61; C07K 2319/75
See application file for complete search history.

(56) References Cited

U.S. PATENT DOCUMENTS

2006/0040327 A1   2/2006  Amiss et al.
2011/0020911 A1   1/2011  Riggs et al.
2014/0259212 A1   9/2014  Plesch et al.
2015/0010947 A1   1/2015  Loh et al.
2015/0185216 A1   7/2015  Albert et al.

FOREIGN PATENT DOCUMENTS

WO    2017066441 A1    4/2017
WO    2018076008 A1    4/2018

OTHER PUBLICATIONS

International Search Report and Written Opinion of the International Searching Authority for International Patent Application No. PCT/US2018/021385, dated Jun. 20, 2018 (14 pages).
Bjorkman, et al., "Probing Protein-Protein Interactions," The Journal of Biological Chemistry, Dec. 2, 1994, pp. 30206-30211, vol. 269, No. 48.
Derosa, et al., "RPtag as an Orally Bioavailable, Hyperstable Epitope Tag and Generalizable Protein Binding Scaffold," Biochemistry, 2018, pp. 3036-3049, vol. 57.
Ha, et al., "Engineered Domain Swapping as and On/Off Switch for Protein Function," Chemistry & Biology, Oct. 22, 2015, pp. 1384-1393, vol. 22.
Karchin, et al., "Small Molecule-Induced Domain Swapping as a Mechanism for Controlling Protein Function and Assembly," Scientific Reports, Mar. 13, 2017, pp. 1-12, vol. 7, No. 44388.
Verbeke, et al., "Genomic Evaluation of *Thermoanaerobacter* spp. for the Construction of Designer Co-Cultures to Improve Lignocellulosic Biofuel Production," PLOS ONE, Mar. 2013, pp. 1-18, vol. 8. Issue 3.
Cuneo, Matthew et al. "The backbone structure of hte termophilic Thermoanaerobacter tengcongensis ribose binding protein is essentially identical to its mesophilic *E. coli* homolog", BMC Structural Biology, Biomed Central Ltd., vol. 8 ,No. 1, Mar. 28, 2008.
Derosa, Jennifer R. et al. "RPtag as an Orally Bioavailable, Hyperstable Epitope Tag and Generalizable Protein Binding Scaffold", Biochemistry, vol. 57, No. 21, May 3, 2018.
Supplemental European Search Report dated Aug. 26, 2020 in connection with European Patent Application No. 18764681.5, 8 pages.
Ha, Jeung-Hoi et al. "Stepwise Conversion of a Binding Protein to a Fluorscent Switch: Application to Thermoanaerobacter tengcongensis Ribose Binding Protein", Biochemistry, vol. 52, No. 5, Jan. 17, 2013.
"Periplasmic sugar-binding protein from *Caldanaerobacter subterraneus* subsp. *pacificus* DSM 12653", Feb. 10, 2009.

*Primary Examiner* — Changhwa J Cheu

(74) *Attorney, Agent, or Firm* — Dorsey & Whitney LLP

(57) ABSTRACT

Disclosed herein are compositions, methods, and systems for the purification and/or detection of recombinant and other proteins. In some embodiments, compositions may comprise recombinant protein with one or more sequences having substantial homology to RP-Tag Small or RP-Tag Large. In some cases, the disclosed compositions may be useful in binding or recognizing target proteins.

14 Claims, 12 Drawing Sheets

Specification includes a Sequence Listing.

Fig. 3

```
ATGGGCAGCA GCTGCCATCACCA TCATCACCAC AGCCAGGATC CGAATTCGAG CTCGATGAAA
GAGGGCAAAA CGATTGGCCT GGTGATCTCT ACCCTGAACA ATCCGTTCTT TGTGACCCTG
AAAAATGGTG CGGAAGAAAA AGCGAAAGAA CTGGGTTACA AAATTATCGT TGAAGATTCG
CAAAATGATT CCTCTAAAGA GCTGTCTAAT GTCGAAGATT TGATTCAACA GAAAGTTGAT
GTTCTGCTGA TCAATCCGGT GGATAGCGAT GCGGTTGTTA CGGCGATTAA AGAAGCGAAT
AGCAAAAATA TCCCGGTTAT TACCATCGAT CGCAGCGCGA ATGGTGGTGA TGTTGTTTCC
CATATCGCCA GCGATAATGT TAAGGGTGGC GAAATGGCCG CGGAATTTAT CGCGAAAGCC
CTGAAAGGCA AGGGGAATGT TGTGGAACTG GAAGGTATCC CGGGGGCGTC TGCGGCACGT
GATCGCGGCA AAGGGTTTGA TGAAGCCATT GCTAAGTATC CGGATATTAA AATCGTTGCA
AAGCAGGCGG CGGATTTTGA TCGTTCCAAA GGTCTGTCAG TGATGGAAAA CATCTTGCAA
GCCCAGCCGA AAATTGATGC AGTGTTTGCG CAAAATGATG AAATGGCTCT GGGCGCTATC
AAAGCCATTG AGGCCGCGAA TCGTCAAGGT ATTATTGTTG TGGGCTTTGA TGGGACCGAA
GATGCTCTGA AAGCGATTAA AGAAGGGAAA ATGGCTGCGA CCATTGCGCA GCAGCCGGCC
CTGATGGGCT CACTGGGTGT GGAGATGGCT GATAAATACC TGAAA
```

Fig. 4

Sequence 1: Full length tteRBP used as a solubility and expression enhancing tag.

MKEGKTIGLVISTLNNPFFVTLKNGAEEKAKELGYKIIVEDSQNDSSKELSNVEDLIQQK
VDVLLINPVDSDAVVTAIKEANSKNIPVITIDRSANGGDVVSHIASDNVKGGEMAAEFIA
KALKGKGNVVELEGIPGASAARDRGKGFDEAIAKYPDIKIVAKQAADFDRSKGLSVMENI
LQAQPKIDAVFAQNDEMALGAIKAIEAANRQGIIVVGFDGTEDALKAIKEGKMAATIAQQ
PALMGSLGVEMADKYLKGEKIPNFIPAELKLITKENVQ

Sequence 2: Large fragment of tteRBP used as an affinity tag. We will call this RP-tag (large). Base sequence shown in bold. Linkers shown as plain text. N terminal his tag (*italics*) included for purification, N terminal Cys included as a handle for site specific labeling and immobilization in our test systems.

MGSSC*HHHHHH*SQDPNSSS**MKEGKTIGLVISTLNNPFFVTLKNGAEEKAKELGYKIIVED
SQNDSSKELSNVEDLIQQKVDVLLINPVDSDAVVTAIKEANSKNIPVITIDRSANGGDVV
SHIASDNVKGGEMAAEFIAKALKGKGNVVELEGIPGASAARDRGKGFDEAIAKYPDIKIV
AKQAADFDRSKGLSVMENILQAQPKIDAVFAQNDEMALGAIKAIEAANRQGIIVVGFDGT
EDALKAIKEGKMAATIAQQPALMGSLGVEMADKYLK**

Sequence 3: Small fragment of tteRBP used as an affinity tag. We will call this RP-tag (small) Base sequence shown in bold, linkers shown as plain text. For the binding experiments shown in this description, the peptide also included an N-terminal Rhodamine 6B label.

GEKIPNFIPAELKLITKENVQGS

SEQUENCE LISTING

<160> NUMBER OF SEQ ID NOS: 94

<210> SEQ ID NO 1
<211> LENGTH: 7
<212> TYPE: PRT
<213> ORGANISM: Artificial Sequence
<220> FEATURE:
<223> OTHER INFORMATION: recombinant

```
<400> SEQUENCE: 1

Gly His His His His His
1               5

<210> SEQ ID NO 2
<211> LENGTH: 19
<212> TYPE: PRT
<213> ORGANISM: Artificial Sequence
<220> FEATURE:
<223> OTHER INFORMATION: recombinant

<400> SEQUENCE: 2

Lys Ile Ala Asn Phe Ile Pro Ala Glu Leu Lys Leu Ile Thr Lys Ala
1               5                   10                  15

Asn Val Gln

<210> SEQ ID NO 3
<211> LENGTH: 276
<212> TYPE: PRT
<213> ORGANISM: Artificial Sequence
<220> FEATURE:
<223> OTHER INFORMATION: recombinant

<400> SEQUENCE: 3

Met Gly Ser Ser Cys His His His His His Ser Gln Asp Pro Asn
1               5                   10                  15

Ser Ser Ser Met Lys Glu Gly Lys Thr Ile Gly Leu Val Ile Ser Thr
                20                  25                  30

Leu Asn Asn Pro Phe Phe Val Thr Leu Lys Asn Gly Ala Glu Glu Lys
            35                  40                  45

Ala Lys Glu Leu Gly Tyr Lys Ile Ile Val Glu Asp Ser Gln Asn Asp
        50                  55                  60

Ser Ser Lys Glu Leu Ser Asn Val Glu Asp Leu Ile Gln Gln Lys Val
65                  70                  75                  80

Asp Val Leu Leu Ile Asn Pro Val Asp Ser Ala Val Val Thr Ala
                85                  90                  95

Ile Lys Glu Ala Asn Ser Lys Asn Ile Pro Val Ile Thr Ile Asp Arg
            100                 105                 110

Ser Ala Asn Gly Gly Asp Val Val Ser His Ile Ala Ser Asp Asn Val
        115                 120                 125

Lys Gly Gly Glu Met Ala Ala Glu Phe Ile Ala Lys Ala Leu Lys Gly
    130                 135                 140

Lys Gly Asn Val Val Glu Leu Glu Gly Ile Pro Gly Ala Ser Ala Ala
145                 150                 155                 160

Arg Asp Arg Gly Lys Gly Phe Asp Glu Ala Ile Ala Lys Tyr Pro Asp
                165                 170                 175

Ile Lys Ile Val Ala Lys Gln Ala Ala Asp Phe Asp Arg Ser Lys Gly
            180                 185                 190

Leu Ser Val Met Glu Asn Ile Leu Gln Ala Gln Pro Lys Ile Asp Ala
        195                 200                 205

Val Phe Ala Gln Asn Asp Glu Met Ala Leu Gly Ala Ile Lys Ala Ile
    210                 215                 220

Glu Ala Ala Asn Arg Gln Gly Ile Ile Val Val Gly Phe Asp Gly Thr
225                 230                 235                 240

Glu Asp Ala Leu Lys Ala Ile Lys Glu Gly Lys Met Ala Ala Thr Ile
                245                 250                 255

Ala Gln Gln Pro Ala Leu Met Gly Ser Leu Gly Val Glu Met Ala Asp
```

Lys Tyr Leu Lys
        275

<210> SEQ ID NO 4
<211> LENGTH: 285
<212> TYPE: PRT
<213> ORGANISM: Artificial Sequence
<220> FEATURE:
<223> OTHER INFORMATION: recombinant

<400> SEQUENCE: 4

Met Gly Ser Ser Gly Glu Lys Ile Pro Asn Phe Ile Pro Ala Glu Leu
1               5                   10                  15

Lys Leu Ile Thr Lys Glu Asn Val Gln Gly Ser Glu Asn Leu Tyr Phe
            20                  25                  30

Gln Gly Gly Ser Met Val Ser Lys Gly Glu Glu Leu Ile Lys Glu Asn
        35                  40                  45

Met His Met Lys Leu Tyr Met Glu Gly Thr Val Asn Asn His His Phe
    50                  55                  60

Lys Cys Thr Ser Glu Gly Glu Gly Lys Pro Tyr Glu Gly Thr Gln Thr
65                  70                  75                  80

Met Arg Ile Lys Val Val Glu Gly Gly Pro Leu Pro Phe Ala Phe Asp
                85                  90                  95

Ile Leu Ala Thr Ser Phe Met Tyr Gly Ser Arg Thr Phe Ile Asn His
            100                 105                 110

Thr Gln Gly Ile Pro Asp Phe Phe Lys Gln Ser Phe Pro Glu Gly Phe
        115                 120                 125

Thr Trp Glu Arg Val Thr Thr Tyr Glu Asp Gly Gly Val Leu Thr Ala
    130                 135                 140

Thr Gln Asp Thr Ser Leu Gln Asp Gly Cys Leu Ile Tyr Asn Val Lys
145                 150                 155                 160

Ile Arg Gly Val Asn Phe Pro Ser Asn Gly Pro Val Met Gln Lys Lys
                165                 170                 175

Thr Leu Gly Trp Glu Ala Asn Thr Glu Met Leu Tyr Pro Ala Asp Gly
            180                 185                 190

Gly Leu Glu Gly Arg Ser Asp Met Ala Leu Lys Leu Val Gly Gly Gly
        195                 200                 205

His Leu Ile Cys Asn Phe Lys Thr Thr Tyr Arg Ser Lys Lys Pro Ala
    210                 215                 220

Lys Asn Leu Lys Met Pro Gly Val Tyr Tyr Val Asp His Arg Leu Glu
225                 230                 235                 240

Arg Ile Lys Glu Ala Asp Lys Glu Thr Tyr Val Glu Gln His Glu Val
                245                 250                 255

Ala Val Ala Arg Tyr Cys Asp Leu Pro Ser Lys Leu Gly His Lys Leu
            260                 265                 270

Asn Gly Ser Ser Gly His His His His His His
        275                 280                 285

<210> SEQ ID NO 5
<211> LENGTH: 529
<212> TYPE: PRT
<213> ORGANISM: Artificial Sequence
<220> FEATURE:
<223> OTHER INFORMATION: recombinant

<400> SEQUENCE: 5

```
Met Gly Ser Ser Ser Gln Asp Pro Asn Ser Ser Met Lys Glu Gly
1               5                   10                  15

Lys Thr Ile Gly Leu Val Ile Ser Thr Leu Asn Asn Pro Phe Phe Val
            20                  25                  30

Thr Leu Lys Asn Gly Ala Glu Glu Lys Ala Lys Glu Leu Gly Tyr Lys
            35                  40                  45

Ile Ile Val Glu Asp Ser Gln Asn Asp Ser Ser Lys Glu Leu Ser Asn
50                  55                  60

Val Glu Asp Leu Ile Gln Gln Lys Val Asp Leu Leu Ile Asn Pro
65                  70                  75                  80

Val Asp Ser Asp Ala Val Val Thr Ala Ile Lys Glu Ala Asn Ser Lys
                85                  90                  95

Asn Ile Pro Val Ile Thr Ile Asp Arg Ser Ala Asn Gly Gly Asp Val
            100                 105                 110

Val Ser His Ile Ala Ser Asp Asn Val Lys Gly Gly Glu Met Ala Ala
            115                 120                 125

Glu Phe Ile Ala Lys Ala Leu Lys Gly Lys Gly Asn Val Val Glu Leu
    130                 135                 140

Glu Gly Ile Pro Gly Ala Ser Ala Ala Arg Asp Arg Gly Lys Gly Phe
145                 150                 155                 160

Asp Glu Ala Ile Ala Lys Tyr Pro Asp Ile Lys Ile Val Ala Lys Gln
                165                 170                 175

Ala Ala Asp Phe Asp Arg Ser Lys Gly Leu Ser Val Met Glu Asn Ile
            180                 185                 190

Leu Gln Ala Gln Pro Lys Ile Asp Ala Val Phe Ala Gln Asn Asp Glu
    195                 200                 205

Met Ala Leu Gly Ala Ile Lys Ala Ile Glu Ala Ala Asn Arg Gln Gly
210                 215                 220

Ile Ile Val Val Gly Phe Asp Gly Thr Glu Asp Ala Leu Lys Ala Ile
225                 230                 235                 240

Lys Glu Gly Lys Met Ala Ala Thr Ile Ala Gln Gln Pro Ala Leu Met
                245                 250                 255

Gly Ser Leu Gly Val Glu Met Ala Asp Lys Tyr Leu Lys Gly Ser Glu
            260                 265                 270

Asn Leu Tyr Phe Gln Gly Gly Ser Met Val Ser Lys Gly Glu Glu Leu
    275                 280                 285

Ile Lys Glu Asn Met His Met Lys Leu Tyr Met Glu Gly Thr Val Asn
    290                 295                 300

Asn His His Phe Lys Cys Thr Ser Glu Gly Glu Gly Lys Pro Tyr Glu
305                 310                 315                 320

Gly Thr Gln Thr Met Arg Ile Lys Val Val Glu Gly Gly Pro Leu Pro
                325                 330                 335

Phe Ala Phe Asp Ile Leu Ala Thr Ser Phe Met Tyr Gly Ser Arg Thr
            340                 345                 350

Phe Ile Asn His Thr Gln Gly Ile Pro Asp Phe Phe Lys Gln Ser Phe
    355                 360                 365

Pro Glu Gly Phe Thr Trp Glu Arg Val Thr Thr Tyr Glu Asp Gly Gly
    370                 375                 380

Val Leu Thr Ala Thr Gln Asp Thr Ser Leu Gln Asp Gly Cys Leu Ile
385                 390                 395                 400

Tyr Asn Val Lys Ile Arg Gly Val Asn Phe Pro Ser Asn Gly Pro Val
                405                 410                 415

Met Gln Lys Lys Thr Leu Gly Trp Glu Ala Asn Thr Glu Met Leu Tyr
```

```
                        420                 425                 430
Pro Ala Asp Gly Gly Leu Glu Gly Arg Ser Asp Met Ala Leu Lys Leu
            435                 440                 445

Val Gly Gly Gly His Leu Ile Cys Asn Phe Lys Thr Thr Tyr Arg Ser
    450                 455                 460

Lys Lys Pro Ala Lys Asn Leu Lys Met Pro Gly Val Tyr Tyr Val Asp
465                 470                 475                 480

His Arg Leu Glu Arg Ile Lys Glu Ala Asp Lys Glu Thr Tyr Val Glu
                485                 490                 495

Gln His Glu Val Ala Val Ala Arg Tyr Cys Asp Leu Pro Ser Lys Leu
            500                 505                 510

Gly His Lys Leu Asn Gly Ser Ser Gly His His His His His His
            515                 520                 525

His

<210> SEQ ID NO 6
<211> LENGTH: 287
<212> TYPE: PRT
<213> ORGANISM: Artificial Sequence
<220> FEATURE:
<223> OTHER INFORMATION: recombinant

<400> SEQUENCE: 6

Met Gly Ser Ser His His His His His His Gly Ser Met Val
1               5                   10                  15

Ser Lys Gly Glu Glu Leu Ile Lys Glu Asn Met His Met Lys Leu Tyr
            20                  25                  30

Met Glu Gly Thr Val Asn Asn His His Phe Lys Cys Thr Ser Glu Gly
        35                  40                  45

Glu Gly Lys Pro Tyr Glu Gly Thr Gln Thr Met Arg Ile Lys Val Val
    50                  55                  60

Glu Gly Gly Pro Leu Pro Phe Ala Phe Asp Ile Leu Ala Thr Ser Phe
65                  70                  75                  80

Met Tyr Gly Ser Arg Thr Phe Ile Asn His Thr Gln Gly Ile Pro Asp
                85                  90                  95

Phe Phe Lys Gln Ser Phe Pro Glu Gly Phe Thr Trp Glu Arg Val Thr
            100                 105                 110

Thr Tyr Glu Asp Gly Gly Val Leu Thr Ala Thr Gln Asp Thr Ser Leu
        115                 120                 125

Gln Asp Gly Cys Leu Ile Tyr Asn Val Lys Ile Arg Gly Val Asn Phe
    130                 135                 140

Pro Ser Asn Gly Pro Val Met Gln Lys Lys Thr Leu Gly Trp Glu Ala
145                 150                 155                 160

Asn Thr Glu Met Leu Tyr Pro Ala Asp Gly Gly Leu Glu Gly Arg Ser
                165                 170                 175

Asp Met Ala Leu Lys Leu Val Gly Gly Gly His Leu Ile Cys Asn Phe
            180                 185                 190

Lys Thr Thr Tyr Arg Ser Lys Lys Pro Ala Lys Asn Leu Lys Met Pro
        195                 200                 205

Gly Val Tyr Tyr Val Asp His Arg Leu Glu Arg Ile Lys Glu Ala Asp
    210                 215                 220

Lys Glu Thr Tyr Val Glu Gln His Glu Val Ala Val Ala Arg Tyr Cys
225                 230                 235                 240

Asp Leu Pro Ser Lys Leu Gly His Lys Leu Asn Gly Ser Ser Gly Glu
                245                 250                 255
```

Asn Leu Tyr Phe Gln Gly Gly Ser Gly Glu Lys Ile Pro Asn Phe Ile
            260                 265                 270

Pro Ala Glu Leu Lys Leu Ile Thr Lys Glu Asn Val Gln Gly Ser
        275                 280                 285

<210> SEQ ID NO 7
<211> LENGTH: 529
<212> TYPE: PRT
<213> ORGANISM: Artificial Sequence
<220> FEATURE:
<223> OTHER INFORMATION: recombinant

<400> SEQUENCE: 7

Met Gly Ser Ser His His His His His His Gly Ser Met Val
1               5                   10                  15

Ser Lys Gly Glu Glu Leu Ile Lys Glu Asn Met His Met Lys Leu Tyr
            20                  25                  30

Met Glu Gly Thr Val Asn Asn His His Phe Lys Cys Thr Ser Glu Gly
        35                  40                  45

Glu Gly Lys Pro Tyr Glu Gly Thr Gln Thr Met Arg Ile Lys Val Val
    50                  55                  60

Glu Gly Gly Pro Leu Pro Phe Ala Phe Asp Ile Leu Ala Thr Ser Phe
65                  70                  75                  80

Met Tyr Gly Ser Arg Thr Phe Ile Asn His Thr Gln Gly Ile Pro Asp
                85                  90                  95

Phe Phe Lys Gln Ser Phe Pro Glu Gly Phe Thr Trp Glu Arg Val Thr
            100                 105                 110

Thr Tyr Glu Asp Gly Gly Val Leu Thr Ala Thr Gln Asp Thr Ser Leu
        115                 120                 125

Gln Asp Gly Cys Leu Ile Tyr Asn Val Lys Ile Arg Gly Val Asn Phe
    130                 135                 140

Pro Ser Asn Gly Pro Val Met Gln Lys Lys Thr Leu Gly Trp Glu Ala
145                 150                 155                 160

Asn Thr Glu Met Leu Tyr Pro Ala Asp Gly Gly Leu Glu Gly Arg Ser
                165                 170                 175

Asp Met Ala Leu Lys Leu Val Gly Gly Gly His Leu Ile Cys Asn Phe
            180                 185                 190

Lys Thr Thr Tyr Arg Ser Lys Lys Pro Ala Lys Asn Leu Lys Met Pro
        195                 200                 205

Gly Val Tyr Tyr Val Asp His Arg Leu Glu Arg Ile Lys Glu Ala Asp
    210                 215                 220

Lys Glu Thr Tyr Val Glu Gln His Glu Val Ala Val Ala Arg Tyr Cys
225                 230                 235                 240

Asp Leu Pro Ser Lys Leu Gly His Lys Leu Asn Gly Ser Ser Gly Glu
                245                 250                 255

Asn Leu Tyr Phe Gln Gly Gly Ser Ser Gln Asp Pro Asn Ser Ser Ser
            260                 265                 270

Met Lys Glu Gly Lys Thr Ile Gly Leu Val Ile Ser Thr Leu Asn Asn
        275                 280                 285

Pro Phe Phe Val Thr Leu Lys Asn Gly Ala Glu Glu Lys Ala Lys Glu
    290                 295                 300

Leu Gly Tyr Lys Ile Ile Val Glu Asp Ser Gln Asn Asp Ser Ser Lys
305                 310                 315                 320

Glu Leu Ser Asn Val Glu Asp Leu Ile Gln Gln Lys Val Asp Val Leu
                325                 330                 335

Leu Ile Asn Pro Val Asp Ser Asp Ala Val Thr Ala Ile Lys Glu
          340                 345                 350

Ala Asn Ser Lys Asn Ile Pro Val Ile Thr Ile Asp Arg Ser Ala Asn
              355                 360                 365

Gly Gly Asp Val Val Ser His Ile Ala Ser Asp Asn Val Lys Gly Gly
          370                 375                 380

Glu Met Ala Ala Glu Phe Ile Ala Lys Ala Leu Lys Gly Lys Gly Asn
385                 390                 395                 400

Val Val Glu Leu Glu Gly Ile Pro Gly Ala Ser Ala Ala Arg Asp Arg
              405                 410                 415

Gly Lys Gly Phe Asp Glu Ala Ile Ala Lys Tyr Pro Asp Ile Lys Ile
              420                 425                 430

Val Ala Lys Gln Ala Ala Asp Phe Asp Arg Ser Lys Gly Leu Ser Val
              435                 440                 445

Met Glu Asn Ile Leu Gln Ala Gln Pro Lys Ile Asp Ala Val Phe Ala
          450                 455                 460

Gln Asn Asp Glu Met Ala Leu Gly Ala Ile Lys Ala Ile Glu Ala Ala
465                 470                 475                 480

Asn Arg Gln Gly Ile Ile Val Val Gly Phe Asp Gly Thr Glu Asp Ala
              485                 490                 495

Leu Lys Ala Ile Lys Glu Gly Lys Met Ala Ala Thr Ile Ala Gln Gln
          500                 505                 510

Pro Ala Leu Met Gly Ser Leu Gly Val Glu Met Ala Asp Lys Tyr Leu
              515                 520                 525

Lys

<210> SEQ ID NO 8
<211> LENGTH: 273
<212> TYPE: PRT
<213> ORGANISM: Artificial Sequence
<220> FEATURE:
<223> OTHER INFORMATION: recombinant

<400> SEQUENCE: 8

Met Gly Ser Ser Pro Ala Glu Leu Lys Leu Ile Thr Lys Gly Ser Glu
1               5                   10                  15

Asn Leu Tyr Phe Gln Gly Gly Ser Met Val Ser Lys Gly Glu Glu Leu
              20                  25                  30

Ile Lys Glu Asn Met His Met Lys Leu Tyr Met Glu Gly Thr Val Asn
          35                  40                  45

Asn His His Phe Lys Cys Thr Ser Glu Gly Glu Gly Lys Pro Tyr Glu
    50                  55                  60

Gly Thr Gln Thr Met Arg Ile Lys Val Val Glu Gly Gly Pro Leu Pro
65                  70                  75                  80

Phe Ala Phe Asp Ile Leu Ala Thr Ser Phe Met Tyr Gly Ser Arg Thr
                85                  90                  95

Phe Ile Asn His Thr Gln Gly Ile Pro Asp Phe Phe Lys Gln Ser Phe
            100                 105                 110

Pro Glu Gly Phe Thr Trp Glu Arg Val Thr Thr Tyr Glu Asp Gly Gly
          115                 120                 125

Val Leu Thr Ala Thr Gln Asp Thr Ser Leu Gln Asp Gly Cys Leu Ile
      130                 135                 140

Tyr Asn Val Lys Ile Arg Gly Val Asn Phe Pro Ser Asn Gly Pro Val
145                 150                 155                 160

```
Met Gln Lys Lys Thr Leu Gly Trp Glu Ala Asn Thr Glu Met Leu Tyr
            165                 170                 175

Pro Ala Asp Gly Gly Leu Glu Gly Arg Ser Asp Met Ala Leu Lys Leu
        180                 185                 190

Val Gly Gly Gly His Leu Ile Cys Asn Phe Lys Thr Thr Tyr Arg Ser
        195                 200                 205

Lys Lys Pro Ala Lys Asn Leu Lys Met Pro Gly Val Tyr Tyr Val Asp
    210                 215                 220

His Arg Leu Glu Arg Ile Lys Glu Ala Asp Lys Glu Thr Tyr Val Glu
225                 230                 235                 240

Gln His Glu Val Ala Val Ala Arg Tyr Cys Asp Leu Pro Ser Lys Leu
                245                 250                 255

Gly His Lys Leu Asn Gly Ser Ser Gly His His His His His His
            260                 265                 270

His

<210> SEQ ID NO 9
<211> LENGTH: 283
<212> TYPE: PRT
<213> ORGANISM: Artificial Sequence
<220> FEATURE:
<223> OTHER INFORMATION: recombinant

<400> SEQUENCE: 9

Met Gly Ser Ser Lys Ile Ala Asn Phe Ile Pro Ala Glu Leu Lys Leu
1               5                   10                  15

Ile Thr Lys Ala Asn Val Gln Gly Ser Glu Asn Leu Tyr Phe Gln Gly
            20                  25                  30

Gly Ser Met Val Ser Lys Gly Glu Glu Leu Ile Lys Glu Asn Met His
        35                  40                  45

Met Lys Leu Tyr Met Glu Gly Thr Val Asn Asn His His Phe Lys Cys
    50                  55                  60

Thr Ser Glu Gly Glu Gly Lys Pro Tyr Glu Gly Thr Gln Thr Met Arg
65                  70                  75                  80

Ile Lys Val Val Glu Gly Gly Pro Leu Pro Phe Ala Phe Asp Ile Leu
                85                  90                  95

Ala Thr Ser Phe Met Tyr Gly Ser Arg Thr Phe Ile Asn His Thr Gln
            100                 105                 110

Gly Ile Pro Asp Phe Phe Lys Gln Ser Phe Pro Glu Gly Phe Thr Trp
        115                 120                 125

Glu Arg Val Thr Thr Tyr Glu Asp Gly Gly Val Leu Thr Ala Thr Gln
    130                 135                 140

Asp Thr Ser Leu Gln Asp Gly Cys Leu Ile Tyr Asn Val Lys Ile Arg
145                 150                 155                 160

Gly Val Asn Phe Pro Ser Asn Gly Pro Val Met Gln Lys Lys Thr Leu
                165                 170                 175

Gly Trp Glu Ala Asn Thr Glu Met Leu Tyr Pro Ala Asp Gly Gly Leu
            180                 185                 190

Glu Gly Arg Ser Asp Met Ala Leu Lys Leu Val Gly Gly His Leu
        195                 200                 205

Ile Cys Asn Phe Lys Thr Thr Tyr Arg Ser Lys Lys Pro Ala Lys Asn
    210                 215                 220

Leu Lys Met Pro Gly Val Tyr Tyr Val Asp His Arg Leu Glu Arg Ile
225                 230                 235                 240

Lys Glu Ala Asp Lys Glu Thr Tyr Val Glu Gln His Glu Val Ala Val
```

```
                    245                 250                 255
Ala Arg Tyr Cys Asp Leu Pro Ser Lys Leu Gly His Lys Leu Asn Gly
                260                 265                 270

Ser Ser Gly His His His His His His His
            275                 280

<210> SEQ ID NO 10
<211> LENGTH: 479
<212> TYPE: PRT
<213> ORGANISM: Artificial Sequence
<220> FEATURE:
<223> OTHER INFORMATION: recombinant

<400> SEQUENCE: 10

Met Gly Ser Pro Ala Glu Leu Lys Leu Ile Thr Lys Gly Gly Ser Glu
1               5                   10                  15

Gln Lys Leu Ile Ser Glu Glu Asp Leu Gly Gly Ser Met Arg Glu Cys
            20                  25                  30

Ile Ser Ile His Val Gly Gln Ala Gly Val Gln Ile Gly Asn Ala Cys
        35                  40                  45

Trp Glu Leu Tyr Cys Leu Glu His Gly Ile Gln Pro Asp Gly Gln Met
    50                  55                  60

Pro Ser Asp Lys Thr Ile Gly Gly Asp Asp Ser Phe Asn Thr Phe
65                  70                  75                  80

Phe Ser Glu Thr Gly Ala Gly Lys His Val Pro Arg Ala Val Phe Val
                85                  90                  95

Asp Leu Glu Pro Thr Val Ile Asp Glu Val Arg Thr Gly Thr Tyr Arg
            100                 105                 110

Gln Leu Phe His Pro Glu Gln Leu Ile Thr Gly Lys Glu Asp Ala Ala
        115                 120                 125

Asn Asn Tyr Ala Arg Gly His Tyr Thr Ile Gly Lys Glu Ile Ile Asp
    130                 135                 140

Leu Val Leu Asp Arg Ile Arg Lys Leu Ala Asp Gln Cys Thr Gly Leu
145                 150                 155                 160

Gln Gly Phe Leu Val Phe His Ser Phe Gly Gly Gly Thr Gly Ser Gly
                165                 170                 175

Phe Thr Ser Leu Leu Met Glu Arg Leu Ser Val Asp Tyr Gly Lys Lys
            180                 185                 190

Ser Lys Leu Glu Phe Ser Ile Tyr Pro Ala Pro Gln Val Ser Thr Ala
        195                 200                 205

Val Val Glu Pro Tyr Asn Ser Ile Leu Thr Thr His Thr Thr Leu Glu
    210                 215                 220

His Ser Asp Cys Ala Phe Met Val Asp Asn Glu Ala Ile Tyr Asp Ile
225                 230                 235                 240

Cys Arg Arg Asn Leu Asp Ile Glu Arg Pro Thr Tyr Thr Asn Leu Asn
                245                 250                 255

Arg Leu Ile Gly Gln Ile Val Ser Ile Thr Ala Ser Leu Arg Phe
            260                 265                 270

Asp Gly Ala Leu Asn Val Asp Leu Thr Glu Phe Gln Thr Asn Leu Val
        275                 280                 285

Pro Tyr Pro Arg Ile His Phe Pro Leu Ala Thr Tyr Ala Pro Val Ile
    290                 295                 300

Ser Ala Glu Lys Ala Tyr His Glu Gln Leu Ser Val Ala Glu Ile Thr
305                 310                 315                 320

Asn Ala Cys Phe Glu Pro Ala Asn Gln Met Val Lys Cys Asp Pro Arg
```

```
                    325                 330                 335
His Gly Lys Tyr Met Ala Cys Cys Leu Leu Tyr Arg Gly Asp Val Val
                340                 345                 350

Pro Lys Asp Val Asn Ala Ala Ile Ala Thr Ile Lys Thr Lys Arg Thr
            355                 360                 365

Ile Gln Phe Val Asp Trp Cys Pro Thr Gly Phe Lys Val Gly Ile Asn
        370                 375                 380

Tyr Gln Pro Pro Thr Val Val Pro Gly Gly Asp Leu Ala Lys Val Gln
385                 390                 395                 400

Arg Ala Val Cys Met Leu Ser Asn Thr Thr Ala Ile Ala Glu Ala Trp
                405                 410                 415

Ala Arg Leu Asp His Lys Phe Asp Leu Met Tyr Ala Lys Arg Ala Phe
            420                 425                 430

Val His Trp Tyr Val Gly Glu Gly Met Glu Glu Gly Glu Phe Ser Glu
        435                 440                 445

Ala Arg Glu Asp Met Ala Ala Leu Glu Lys Asp Tyr Glu Glu Val Gly
450                 455                 460

Val Asp Ser Val Glu Gly Glu Gly Glu Glu Glu Gly Glu Glu Tyr
465                 470                 475

<210> SEQ ID NO 11
<211> LENGTH: 127
<212> TYPE: PRT
<213> ORGANISM: Artificial Sequence
<220> FEATURE:
<223> OTHER INFORMATION: recombinant

<400> SEQUENCE: 11

Met Gly Ser Ser His His His His His His Glu Asn Leu Tyr
1               5                   10                  15

Phe Gln Ser Leu Gly Ser Leu Thr Ile Ala Glu Pro Ala Met Ile Ala
                20                  25                  30

Glu Cys Lys Thr Arg Thr Glu Val Phe Glu Ile Ser Arg Arg Leu Ile
            35                  40                  45

Asp Arg Thr Asn Ala Asn Phe Leu Val Trp Pro Pro Cys Val Glu Val
        50                  55                  60

Gln Arg Cys Ser Gly Cys Cys Asn Asn Arg Asn Val Gln Cys Arg Pro
65                  70                  75                  80

Thr Gln Val Gln Leu Arg Pro Val Gln Val Arg Lys Ile Glu Ile Val
                85                  90                  95

Arg Lys Lys Pro Ile Phe Lys Lys Ala Thr Val Thr Leu Glu Asp His
            100                 105                 110

Leu Ala Cys Lys Cys Glu Thr Val Ala Ala Ala Arg Pro Val Thr
        115                 120                 125

<210> SEQ ID NO 12
<211> LENGTH: 16
<212> TYPE: PRT
<213> ORGANISM: Artificial Sequence
<220> FEATURE:
<223> OTHER INFORMATION: recombinant

<400> SEQUENCE: 12

Gly Ser Leu Gly Ser Leu Thr Ile Ala Glu Pro Ala Met Ile Ala Glu
1               5                   10                  15

<210> SEQ ID NO 13
<211> LENGTH: 21
```

```
<212> TYPE: PRT
<213> ORGANISM: Thermoanaerobacter tengcongensis

<400> SEQUENCE: 13

Gly Glu Lys Ile Pro Asn Phe Ile Pro Ala Glu Leu Lys Leu Ile Thr
1               5                   10                  15

Lys Glu Asn Val Gln
            20

<210> SEQ ID NO 14
<211> LENGTH: 21
<212> TYPE: PRT
<213> ORGANISM: Artificial Sequence
<220> FEATURE:
<223> OTHER INFORMATION: recombinant

<400> SEQUENCE: 14

Ala Glu Lys Ile Pro Asn Phe Ile Pro Ala Glu Leu Lys Leu Ile Thr
1               5                   10                  15

Lys Glu Asn Val Gln
            20

<210> SEQ ID NO 15
<211> LENGTH: 21
<212> TYPE: PRT
<213> ORGANISM: Artificial Sequence
<220> FEATURE:
<223> OTHER INFORMATION: recombinant

<400> SEQUENCE: 15

Gly Ala Lys Ile Pro Asn Phe Ile Pro Ala Glu Leu Lys Leu Ile Thr
1               5                   10                  15

Lys Glu Asn Val Gln
            20

<210> SEQ ID NO 16
<211> LENGTH: 21
<212> TYPE: PRT
<213> ORGANISM: Artificial Sequence
<220> FEATURE:
<223> OTHER INFORMATION: recombinant

<400> SEQUENCE: 16

Gly Glu Ala Ile Pro Asn Phe Ile Pro Ala Glu Leu Lys Leu Ile Thr
1               5                   10                  15

Lys Glu Asn Val Gln
            20

<210> SEQ ID NO 17
<211> LENGTH: 21
<212> TYPE: PRT
<213> ORGANISM: Artificial Sequence
<220> FEATURE:
<223> OTHER INFORMATION: recombinant

<400> SEQUENCE: 17

Gly Glu Lys Ala Pro Asn Phe Ile Pro Ala Glu Leu Lys Leu Ile Thr
1               5                   10                  15

Lys Glu Asn Val Gln
            20

<210> SEQ ID NO 18
<211> LENGTH: 21
<212> TYPE: PRT
```

<213> ORGANISM: Artificial Sequence
<220> FEATURE:
<223> OTHER INFORMATION: recombinant

<400> SEQUENCE: 18

Gly Glu Lys Ile Ala Asn Phe Ile Pro Ala Glu Leu Lys Leu Ile Thr
1               5                   10                  15

Lys Glu Asn Val Gln
            20

<210> SEQ ID NO 19
<211> LENGTH: 21
<212> TYPE: PRT
<213> ORGANISM: Artificial Sequence
<220> FEATURE:
<223> OTHER INFORMATION: recombinant

<400> SEQUENCE: 19

Gly Glu Lys Ile Pro Ala Phe Ile Pro Ala Glu Leu Lys Leu Ile Thr
1               5                   10                  15

Lys Glu Asn Val Gln
            20

<210> SEQ ID NO 20
<211> LENGTH: 21
<212> TYPE: PRT
<213> ORGANISM: Artificial Sequence
<220> FEATURE:
<223> OTHER INFORMATION: recombinant

<400> SEQUENCE: 20

Gly Glu Lys Ile Pro Asn Ala Ile Pro Ala Glu Leu Lys Leu Ile Thr
1               5                   10                  15

Lys Glu Asn Val Gln
            20

<210> SEQ ID NO 21
<211> LENGTH: 21
<212> TYPE: PRT
<213> ORGANISM: Artificial Sequence
<220> FEATURE:
<223> OTHER INFORMATION: recombinant

<400> SEQUENCE: 21

Gly Glu Lys Ile Pro Asn Phe Ala Pro Ala Glu Leu Lys Leu Ile Thr
1               5                   10                  15

Lys Glu Asn Val Gln
            20

<210> SEQ ID NO 22
<211> LENGTH: 21
<212> TYPE: PRT
<213> ORGANISM: Artificial Sequence
<220> FEATURE:
<223> OTHER INFORMATION: recombinant

<400> SEQUENCE: 22

Gly Glu Lys Ile Pro Asn Phe Ile Ala Ala Glu Leu Lys Leu Ile Thr
1               5                   10                  15

Lys Glu Asn Val Gln
            20

<210> SEQ ID NO 23
<211> LENGTH: 21

```
<212> TYPE: PRT
<213> ORGANISM: Artificial Sequence
<220> FEATURE:
<223> OTHER INFORMATION: recombinant

<400> SEQUENCE: 23

Gly Glu Lys Ile Pro Asn Phe Ile Pro Ala Ala Leu Lys Leu Ile Thr
1               5                   10                  15

Lys Glu Asn Val Gln
            20

<210> SEQ ID NO 24
<211> LENGTH: 21
<212> TYPE: PRT
<213> ORGANISM: Artificial Sequence
<220> FEATURE:
<223> OTHER INFORMATION: recombinant

<400> SEQUENCE: 24

Gly Glu Lys Ile Pro Asn Phe Ile Pro Ala Glu Ala Lys Leu Ile Thr
1               5                   10                  15

Lys Glu Asn Val Gln
            20

<210> SEQ ID NO 25
<211> LENGTH: 21
<212> TYPE: PRT
<213> ORGANISM: Artificial Sequence
<220> FEATURE:
<223> OTHER INFORMATION: recombinant

<400> SEQUENCE: 25

Gly Glu Lys Ile Pro Asn Phe Ile Pro Ala Glu Leu Ala Leu Ile Thr
1               5                   10                  15

Lys Glu Asn Val Gln
            20

<210> SEQ ID NO 26
<211> LENGTH: 21
<212> TYPE: PRT
<213> ORGANISM: Artificial Sequence
<220> FEATURE:
<223> OTHER INFORMATION: recombinant

<400> SEQUENCE: 26

Gly Glu Lys Ile Pro Asn Phe Ile Pro Ala Glu Leu Lys Ala Ile Thr
1               5                   10                  15

Lys Glu Asn Val Gln
            20

<210> SEQ ID NO 27
<211> LENGTH: 21
<212> TYPE: PRT
<213> ORGANISM: Artificial Sequence
<220> FEATURE:
<223> OTHER INFORMATION: recombinant

<400> SEQUENCE: 27

Gly Glu Lys Ile Pro Asn Phe Ile Pro Ala Glu Leu Lys Leu Ala Thr
1               5                   10                  15

Lys Glu Asn Val Gln
            20

<210> SEQ ID NO 28
```

```
<211> LENGTH: 21
<212> TYPE: PRT
<213> ORGANISM: Artificial Sequence
<220> FEATURE:
<223> OTHER INFORMATION: recombinant

<400> SEQUENCE: 28

Gly Glu Lys Ile Pro Asn Phe Ile Pro Ala Glu Leu Lys Leu Ile Ala
1               5                   10                  15

Lys Glu Asn Val Gln
            20

<210> SEQ ID NO 29
<211> LENGTH: 21
<212> TYPE: PRT
<213> ORGANISM: Artificial Sequence
<220> FEATURE:
<223> OTHER INFORMATION: recombinant

<400> SEQUENCE: 29

Gly Glu Lys Ile Pro Asn Phe Ile Pro Ala Glu Leu Lys Leu Ile Thr
1               5                   10                  15

Ala Glu Asn Val Gln
            20

<210> SEQ ID NO 30
<211> LENGTH: 21
<212> TYPE: PRT
<213> ORGANISM: Artificial Sequence
<220> FEATURE:
<223> OTHER INFORMATION: recombinant

<400> SEQUENCE: 30

Gly Glu Lys Ile Pro Asn Phe Ile Pro Ala Glu Leu Lys Leu Ile Thr
1               5                   10                  15

Lys Ala Asn Val Gln
            20

<210> SEQ ID NO 31
<211> LENGTH: 21
<212> TYPE: PRT
<213> ORGANISM: Artificial Sequence
<220> FEATURE:
<223> OTHER INFORMATION: recombinant

<400> SEQUENCE: 31

Gly Glu Lys Ile Pro Asn Phe Ile Pro Ala Glu Leu Lys Leu Ile Thr
1               5                   10                  15

Lys Glu Asn Val Gln
            20

<210> SEQ ID NO 32
<211> LENGTH: 21
<212> TYPE: PRT
<213> ORGANISM: Artificial Sequence
<220> FEATURE:
<223> OTHER INFORMATION: recombinant

<400> SEQUENCE: 32

Gly Glu Lys Ile Pro Asn Phe Ile Pro Ala Glu Leu Lys Leu Ile Thr
1               5                   10                  15

Lys Glu Asn Val Gln
            20
```

<210> SEQ ID NO 33
<211> LENGTH: 21
<212> TYPE: PRT
<213> ORGANISM: Artificial Sequence
<220> FEATURE:
<223> OTHER INFORMATION: recombinant

<400> SEQUENCE: 33

Gly Glu Lys Ile Pro Asn Phe Ile Pro Ala Glu Leu Lys Leu Ile Thr
1               5                   10                  15

Lys Glu Asn Val Gln
            20

<210> SEQ ID NO 34
<211> LENGTH: 20
<212> TYPE: PRT
<213> ORGANISM: Artificial Sequence
<220> FEATURE:
<223> OTHER INFORMATION: recombinant

<400> SEQUENCE: 34

Glu Lys Ile Pro Asn Phe Ile Pro Ala Glu Leu Lys Leu Ile Thr Lys
1               5                   10                  15

Glu Asn Val Gln
            20

<210> SEQ ID NO 35
<211> LENGTH: 19
<212> TYPE: PRT
<213> ORGANISM: Artificial Sequence
<220> FEATURE:
<223> OTHER INFORMATION: recombinant

<400> SEQUENCE: 35

Lys Ile Pro Asn Phe Ile Pro Ala Glu Leu Lys Leu Ile Thr Lys Glu
1               5                   10                  15

Asn Val Gln

<210> SEQ ID NO 36
<211> LENGTH: 18
<212> TYPE: PRT
<213> ORGANISM: Artificial Sequence
<220> FEATURE:
<223> OTHER INFORMATION: recombinant

<400> SEQUENCE: 36

Ile Pro Asn Phe Ile Pro Ala Glu Leu Lys Leu Ile Thr Lys Glu Asn
1               5                   10                  15

Val Gln

<210> SEQ ID NO 37
<211> LENGTH: 17
<212> TYPE: PRT
<213> ORGANISM: Artificial Sequence
<220> FEATURE:
<223> OTHER INFORMATION: recombinant

<400> SEQUENCE: 37

Pro Asn Phe Ile Pro Ala Glu Leu Lys Leu Ile Thr Lys Glu Asn Val
1               5                   10                  15

Gln

<210> SEQ ID NO 38
<211> LENGTH: 16

```
<212> TYPE: PRT
<213> ORGANISM: Artificial Sequence
<220> FEATURE:
<223> OTHER INFORMATION: recombinant

<400> SEQUENCE: 38

Asn Phe Ile Pro Ala Glu Leu Lys Leu Ile Thr Lys Glu Asn Val Gln
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: recombinant

<400> SEQUENCE: 39

Phe Ile Pro Ala Glu Leu Lys Leu Ile Thr Lys Glu Asn Val Gln
1               5                   10                  15

<210> SEQ ID NO 40
<211> LENGTH: 14
<212> TYPE: PRT
<213> ORGANISM: Artificial Sequence
<220> FEATURE:
<223> OTHER INFORMATION: recombinant

<400> SEQUENCE: 40

Ile Pro Ala Glu Leu Lys Leu Ile Thr Lys Glu Asn Val Gln
1               5                   10

<210> SEQ ID NO 41
<211> LENGTH: 13
<212> TYPE: PRT
<213> ORGANISM: Artificial Sequence
<220> FEATURE:
<223> OTHER INFORMATION: recombinant

<400> SEQUENCE: 41

Pro Ala Glu Leu Lys Leu Ile Thr Lys Glu Asn Val Gln
1               5                   10

<210> SEQ ID NO 42
<211> LENGTH: 12
<212> TYPE: PRT
<213> ORGANISM: Artificial Sequence
<220> FEATURE:
<223> OTHER INFORMATION: recombinant

<400> SEQUENCE: 42

Ala Glu Leu Lys Leu Ile Thr Lys Glu Asn Val Gln
1               5                   10

<210> SEQ ID NO 43
<211> LENGTH: 11
<212> TYPE: PRT
<213> ORGANISM: Artificial Sequence
<220> FEATURE:
<223> OTHER INFORMATION: recombinant

<400> SEQUENCE: 43

Glu Leu Lys Leu Ile Thr Lys Glu Asn Val Gln
1               5                   10

<210> SEQ ID NO 44
<211> LENGTH: 10
<212> TYPE: PRT
```

```
<213> ORGANISM: Artificial Sequence
<220> FEATURE:
<223> OTHER INFORMATION: recombinant

<400> SEQUENCE: 44

Leu Lys Leu Ile Thr Lys Glu Asn Val Gln
1               5                   10

<210> SEQ ID NO 45
<211> LENGTH: 9
<212> TYPE: PRT
<213> ORGANISM: Artificial Sequence
<220> FEATURE:
<223> OTHER INFORMATION: recombinant

<400> SEQUENCE: 45

Lys Leu Ile Thr Lys Glu Asn Val Gln
1               5

<210> SEQ ID NO 46
<211> LENGTH: 8
<212> TYPE: PRT
<213> ORGANISM: Artificial Sequence
<220> FEATURE:
<223> OTHER INFORMATION: recombinant

<400> SEQUENCE: 46

Leu Ile Thr Lys Glu Asn Val Gln
1               5

<210> SEQ ID NO 47
<211> LENGTH: 7
<212> TYPE: PRT
<213> ORGANISM: Artificial Sequence
<220> FEATURE:
<223> OTHER INFORMATION: recombinant

<400> SEQUENCE: 47

Ile Thr Lys Glu Asn Val Gln
1               5

<210> SEQ ID NO 48
<211> LENGTH: 6
<212> TYPE: PRT
<213> ORGANISM: Artificial Sequence
<220> FEATURE:
<223> OTHER INFORMATION: recombinant

<400> SEQUENCE: 48

Thr Lys Glu Asn Val Gln
1               5

<210> SEQ ID NO 49
<211> LENGTH: 5
<212> TYPE: PRT
<213> ORGANISM: Artificial Sequence
<220> FEATURE:
<223> OTHER INFORMATION: recombinant

<400> SEQUENCE: 49

Lys Glu Asn Val Gln
1               5

<210> SEQ ID NO 50
<211> LENGTH: 4
<212> TYPE: PRT
<213> ORGANISM: Artificial Sequence
```

```
<220> FEATURE:
<223> OTHER INFORMATION: recombinant

<400> SEQUENCE: 50

Glu Asn Val Gln
1

<210> SEQ ID NO 51
<211> LENGTH: 20
<212> TYPE: PRT
<213> ORGANISM: Artificial Sequence
<220> FEATURE:
<223> OTHER INFORMATION: recombinant

<400> SEQUENCE: 51

Gly Glu Lys Ile Pro Asn Phe Ile Pro Ala Glu Leu Lys Leu Ile Thr
1               5                   10                  15

Lys Glu Asn Val
            20

<210> SEQ ID NO 52
<211> LENGTH: 19
<212> TYPE: PRT
<213> ORGANISM: Artificial Sequence
<220> FEATURE:
<223> OTHER INFORMATION: recombinant

<400> SEQUENCE: 52

Gly Glu Lys Ile Pro Asn Phe Ile Pro Ala Glu Leu Lys Leu Ile Thr
1               5                   10                  15

Lys Glu Asn

<210> SEQ ID NO 53
<211> LENGTH: 18
<212> TYPE: PRT
<213> ORGANISM: Artificial Sequence
<220> FEATURE:
<223> OTHER INFORMATION: recombinant

<400> SEQUENCE: 53

Gly Glu Lys Ile Pro Asn Phe Ile Pro Ala Glu Leu Lys Leu Ile Thr
1               5                   10                  15

Lys Glu

<210> SEQ ID NO 54
<211> LENGTH: 17
<212> TYPE: PRT
<213> ORGANISM: Artificial Sequence
<220> FEATURE:
<223> OTHER INFORMATION: recombinant

<400> SEQUENCE: 54

Gly Glu Lys Ile Pro Asn Phe Ile Pro Ala Glu Leu Lys Leu Ile Thr
1               5                   10                  15

Lys

<210> SEQ ID NO 55
<211> LENGTH: 16
<212> TYPE: PRT
<213> ORGANISM: Artificial Sequence
<220> FEATURE:
<223> OTHER INFORMATION: recombinant

<400> SEQUENCE: 55
```

```
Gly Glu Lys Ile Pro Asn Phe Ile Pro Ala Glu Leu Lys Leu Ile Thr
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: recombinant

<400> SEQUENCE: 56

```
Gly Glu Lys Ile Pro Asn Phe Ile Pro Ala Glu Leu Lys Leu Ile
1               5                   10                  15
```

<210> SEQ ID NO 57
<211> LENGTH: 14
<212> TYPE: PRT
<213> ORGANISM: Artificial Sequence
<220> FEATURE:
<223> OTHER INFORMATION: recombinant

<400> SEQUENCE: 57

```
Gly Glu Lys Ile Pro Asn Phe Ile Pro Ala Glu Leu Lys Leu
1               5                   10
```

<210> SEQ ID NO 58
<211> LENGTH: 13
<212> TYPE: PRT
<213> ORGANISM: Artificial Sequence
<220> FEATURE:
<223> OTHER INFORMATION: recombinant

<400> SEQUENCE: 58

```
Gly Glu Lys Ile Pro Asn Phe Ile Pro Ala Glu Leu Lys
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: recombinant

<400> SEQUENCE: 59

```
Gly Glu Lys Ile Pro Asn Phe Ile Pro Ala Glu Leu
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: recombinant

<400> SEQUENCE: 60

```
Gly Glu Lys Ile Pro Asn Phe Ile Pro Ala Glu
1               5                   10
```

<210> SEQ ID NO 61
<211> LENGTH: 10
<212> TYPE: PRT
<213> ORGANISM: Artificial Sequence
<220> FEATURE:
<223> OTHER INFORMATION: recombinant

<400> SEQUENCE: 61

```
Gly Glu Lys Ile Pro Asn Phe Ile Pro Ala
```

```
1               5                    10
```

<210> SEQ ID NO 62
<211> LENGTH: 9
<212> TYPE: PRT
<213> ORGANISM: Artificial Sequence
<220> FEATURE:
<223> OTHER INFORMATION: recombinant

<400> SEQUENCE: 62

```
Gly Glu Lys Ile Pro Asn Phe Ile Pro
1               5
```

<210> SEQ ID NO 63
<211> LENGTH: 8
<212> TYPE: PRT
<213> ORGANISM: Artificial Sequence
<220> FEATURE:
<223> OTHER INFORMATION: recombinant

<400> SEQUENCE: 63

```
Gly Glu Lys Ile Pro Asn Phe Ile
1               5
```

<210> SEQ ID NO 64
<211> LENGTH: 7
<212> TYPE: PRT
<213> ORGANISM: Artificial Sequence
<220> FEATURE:
<223> OTHER INFORMATION: recombinant

<400> SEQUENCE: 64

```
Gly Glu Lys Ile Pro Asn Phe
1               5
```

<210> SEQ ID NO 65
<211> LENGTH: 6
<212> TYPE: PRT
<213> ORGANISM: Artificial Sequence
<220> FEATURE:
<223> OTHER INFORMATION: recombinant

<400> SEQUENCE: 65

```
Gly Glu Lys Ile Pro Asn
1               5
```

<210> SEQ ID NO 66
<211> LENGTH: 5
<212> TYPE: PRT
<213> ORGANISM: Artificial Sequence
<220> FEATURE:
<223> OTHER INFORMATION: recombinant

<400> SEQUENCE: 66

```
Gly Glu Lys Ile Pro
1               5
```

<210> SEQ ID NO 67
<211> LENGTH: 8
<212> TYPE: PRT
<213> ORGANISM: Artificial Sequence
<220> FEATURE:
<223> OTHER INFORMATION: recombinant

<400> SEQUENCE: 67

```
Glu Leu Lys Leu Ile Thr Lys Glu
1               5
```

-continued

```
<210> SEQ ID NO 68
<211> LENGTH: 8
<212> TYPE: PRT
<213> ORGANISM: Artificial Sequence
<220> FEATURE:
<223> OTHER INFORMATION: recombinant

<400> SEQUENCE: 68

Glu Leu Lys Leu Ile Thr Lys Ala
1               5

<210> SEQ ID NO 69
<211> LENGTH: 6
<212> TYPE: PRT
<213> ORGANISM: Artificial Sequence
<220> FEATURE:
<223> OTHER INFORMATION: recombinant

<400> SEQUENCE: 69

Glu Leu Lys Leu Ile Thr
1               5

<210> SEQ ID NO 70
<211> LENGTH: 10
<212> TYPE: PRT
<213> ORGANISM: Artificial Sequence
<220> FEATURE:
<223> OTHER INFORMATION: recombinant

<400> SEQUENCE: 70

Pro Ala Glu Leu Lys Leu Ile Thr Lys Glu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: recombinant

<400> SEQUENCE: 71

Pro Ala Glu Leu Lys Leu Ile Thr Lys Ala
1               5                   10

<210> SEQ ID NO 72
<211> LENGTH: 9
<212> TYPE: PRT
<213> ORGANISM: Artificial Sequence
<220> FEATURE:
<223> OTHER INFORMATION: recombinant

<400> SEQUENCE: 72

Pro Ala Glu Leu Lys Leu Ile Thr Lys
1               5

<210> SEQ ID NO 73
<211> LENGTH: 12
<212> TYPE: PRT
<213> ORGANISM: Artificial Sequence
<220> FEATURE:
<223> OTHER INFORMATION: recombinant

<400> SEQUENCE: 73

Phe Ile Pro Ala Glu Leu Lys Leu Ile Thr Lys Glu
1               5                   10
```

<210> SEQ ID NO 74
<211> LENGTH: 12
<212> TYPE: PRT
<213> ORGANISM: Artificial Sequence
<220> FEATURE:
<223> OTHER INFORMATION: recombinant

<400> SEQUENCE: 74

Phe Ile Pro Ala Glu Leu Lys Leu Ile Thr Lys Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: recombinant

<400> SEQUENCE: 75

Phe Ile Pro Ala Glu Leu Lys Leu Ile Thr Lys
1               5                   10

<210> SEQ ID NO 76
<211> LENGTH: 18
<212> TYPE: PRT
<213> ORGANISM: Artificial Sequence
<220> FEATURE:
<223> OTHER INFORMATION: recombinant

<400> SEQUENCE: 76

Ile Ala Asn Phe Ile Pro Ala Glu Leu Lys Leu Ile Thr Lys Ala Asn
1               5                   10                  15

Val Gln

<210> SEQ ID NO 77
<211> LENGTH: 16
<212> TYPE: PRT
<213> ORGANISM: Artificial Sequence
<220> FEATURE:
<223> OTHER INFORMATION: recombinant

<400> SEQUENCE: 77

Lys Ile Pro Asn Phe Ile Pro Ala Glu Leu Lys Leu Ile Thr Lys Glu
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: recombinant

<400> SEQUENCE: 78

Lys Ile Pro Asn Phe Ile Pro Ala Glu Leu Lys Leu Ile Thr Lys Ala
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: recombinant

<400> SEQUENCE: 79

Lys Ile Pro Asn Phe Ile Pro Ala Glu Leu Lys Leu Ile Thr Lys
1               5                   10                  15

```
<210> SEQ ID NO 80
<211> LENGTH: 16
<212> TYPE: PRT
<213> ORGANISM: Artificial Sequence
<220> FEATURE:
<223> OTHER INFORMATION: recombinant

<400> SEQUENCE: 80

Lys Ile Ala Asn Phe Ile Pro Ala Glu Leu Lys Leu Ile Thr Lys Glu
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: recombinant

<400> SEQUENCE: 81

Lys Ile Ala Asn Phe Ile Pro Ala Glu Leu Lys Leu Ile Thr Lys Ala
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: recombinant

<400> SEQUENCE: 82

Lys Ile Ala Asn Phe Ile Pro Ala Glu Leu Lys Leu Ile Thr Lys
1               5                   10                  15

<210> SEQ ID NO 83
<211> LENGTH: 19
<212> TYPE: PRT
<213> ORGANISM: Artificial Sequence
<220> FEATURE:
<223> OTHER INFORMATION: recombinant

<400> SEQUENCE: 83

Lys Ile Pro Asn Phe Ile Pro Ala Glu Leu Lys Leu Ile Thr Lys Ala
1               5                   10                  15

Asn Val Gln

<210> SEQ ID NO 84
<211> LENGTH: 19
<212> TYPE: PRT
<213> ORGANISM: Artificial Sequence
<220> FEATURE:
<223> OTHER INFORMATION: recombinant

<400> SEQUENCE: 84

Lys Ile Ala Asn Phe Ile Pro Ala Glu Leu Lys Leu Ile Thr Lys Ala
1               5                   10                  15

Asn Val Gln

<210> SEQ ID NO 85
<211> LENGTH: 19
<212> TYPE: PRT
<213> ORGANISM: Artificial Sequence
<220> FEATURE:
<223> OTHER INFORMATION: recombinant

<400> SEQUENCE: 85
```

```
Arg Ile Ala Asn Phe Ile Pro Ala Glu Leu Lys Leu Ile Thr Lys Ala
1               5                   10                  15

Asn Val Gln

<210> SEQ ID NO 86
<211> LENGTH: 19
<212> TYPE: PRT
<213> ORGANISM: Artificial Sequence
<220> FEATURE:
<223> OTHER INFORMATION: recombinant

<400> SEQUENCE: 86

Ala Ile Ala Asn Phe Ile Pro Ala Glu Leu Lys Leu Ile Thr Lys Ala
1               5                   10                  15

Asn Val Gln

<210> SEQ ID NO 87
<211> LENGTH: 19
<212> TYPE: PRT
<213> ORGANISM: Artificial Sequence
<220> FEATURE:
<223> OTHER INFORMATION: recombinant

<400> SEQUENCE: 87

Ala Ile Ala Asn Phe Ile Pro Ala Glu Leu Lys Leu Ile Thr Lys Glu
1               5                   10                  15

Asn Val Gln

<210> SEQ ID NO 88
<211> LENGTH: 19
<212> TYPE: PRT
<213> ORGANISM: Artificial Sequence
<220> FEATURE:
<223> OTHER INFORMATION: recombinant

<400> SEQUENCE: 88

Lys Ile Pro Asn Phe Ile Pro Ala Glu Leu Lys Leu Ile Thr Lys Ala
1               5                   10                  15

Asn Ala Ala

<210> SEQ ID NO 89
<211> LENGTH: 19
<212> TYPE: PRT
<213> ORGANISM: Artificial Sequence
<220> FEATURE:
<223> OTHER INFORMATION: recombinant

<400> SEQUENCE: 89

Lys Ile Ala Asn Phe Ile Pro Ala Glu Leu Lys Leu Ile Thr Lys Ala
1               5                   10                  15

Asn Ala Ala

<210> SEQ ID NO 90
<211> LENGTH: 21
<212> TYPE: PRT
<213> ORGANISM: Artificial Sequence
<220> FEATURE:
<223> OTHER INFORMATION: recombinant

<400> SEQUENCE: 90

Gly Glu Lys Ile Pro Asn Phe Ile Pro Ala Glu Leu Lys Lys Ile Thr
1               5                   10                  15
```

Lys Glu Asn Val Gln
        20

<210> SEQ ID NO 91
<211> LENGTH: 24
<212> TYPE: PRT
<213> ORGANISM: Thermoanaerobacter tengcongensis

<400> SEQUENCE: 91

Gly Glu Lys Ile Pro Asn Phe Ile Pro Ala Glu Leu Lys Leu Ile Thr
1               5                   10                  15

Lys Glu Asn Val Gln Gly Gly Cys
        20

<210> SEQ ID NO 92
<211> LENGTH: 22
<212> TYPE: PRT
<213> ORGANISM: Artificial Sequence
<220> FEATURE:
<223> OTHER INFORMATION: recombinant

<400> SEQUENCE: 92

Lys Ile Ala Asn Phe Ile Pro Ala Glu Leu Lys Leu Ile Thr Lys Ala
1               5                   10                  15

Asn Val Gln Gly Gly Cys
        20

<210> SEQ ID NO 93
<211> LENGTH: 828
<212> TYPE: DNA
<213> ORGANISM: Thermoanaerobacter tengcongensis

<400> SEQUENCE: 93

| | | |
|---|---|---|
| atgggcagca gctgccatca ccatcatcac cacagccagg atccgaattc gagctcgatg | 60 |
| aaagagggca aaacgattgg cctggtgatc tctaccctga caatccgtt ctttgtgacc | 120 |
| ctgaaaaatg gtgcggaaga aaaagcgaaa gaactgggtt acaaaattat cgttgaagat | 180 |
| tcgcaaaatg attcctctaa agagctgtct aatgtcgaag atttgattca acagaaagtt | 240 |
| gatgttctgc tgatcaatcc ggtggatagc gatgcggttg ttacggcgat taagaagcg | 300 |
| aatagcaaaa atatcccggt tattaccatc gatcgcagcg cgaatggtgg tgatgttgtt | 360 |
| tcccatatcg ccagcgataa tgttaagggt ggcgaaatgg ccgcggaatt tatcgcgaaa | 420 |
| gccctgaaag caaggggaa tgttgtggaa ctggaaggta tcccggggggc gtctgcggca | 480 |
| cgtgatcgcg gcaagggtt tgatgaagcc attgctaagt atccggatat aaaatcgtt | 540 |
| gcaaagcagg cggcggattt tgatcgttcc aaaggtctgt cagtgatgga aacatcttg | 600 |
| caagcccagc cgaaaattga tgcagtgttt gcgcaaaatg atgaaatggc tctgggcgct | 660 |
| atcaaagcca ttgaggccgc gaatcgtcaa ggtattattg ttgtgggctt tgatgggacc | 720 |
| gaagatgctc tgaaagcgat taagaaggg aaaatggctg cgaccattgc gcagcagccg | 780 |
| gccctgatgg gctcactggg tgtggagatg gctgataaat acctgaaa | 828 |

<210> SEQ ID NO 94
<211> LENGTH: 278
<212> TYPE: PRT
<213> ORGANISM: Thermoanaerobacter tengcongensis

<400> SEQUENCE: 94

Met Lys Glu Gly Lys Thr Ile Gly Leu Val Ile Ser Thr Leu Asn Asn
1               5                   10                  15

-continued

```
Pro Phe Phe Val Thr Leu Lys Asn Gly Ala Glu Glu Lys Ala Lys Glu
            20                  25                  30

Leu Gly Tyr Lys Ile Ile Val Glu Asp Ser Gln Asn Asp Ser Ser Lys
            35                  40                  45

Glu Leu Ser Asn Val Glu Asp Leu Ile Gln Gln Lys Val Asp Val Leu
 50                  55                  60

Leu Ile Asn Pro Val Asp Ser Asp Ala Val Val Thr Ala Ile Lys Glu
 65              70                  75                  80

Ala Asn Ser Lys Asn Ile Pro Val Ile Thr Ile Asp Arg Ser Ala Asn
                85                  90                  95

Gly Gly Asp Val Val Ser His Ile Ala Ser Asp Asn Val Lys Gly Gly
            100                 105                 110

Glu Met Ala Ala Glu Phe Ile Ala Lys Ala Leu Lys Gly Lys Gly Asn
            115                 120                 125

Val Val Glu Leu Glu Gly Ile Pro Gly Ala Ser Ala Ala Arg Asp Arg
130                 135                 140

Gly Lys Gly Phe Asp Glu Ala Ile Ala Lys Tyr Pro Asp Ile Lys Ile
145             150                 155                 160

Val Ala Lys Gln Ala Ala Asp Phe Asp Arg Ser Lys Gly Leu Ser Val
                165                 170                 175

Met Glu Asn Ile Leu Gln Ala Gln Pro Lys Ile Asp Ala Val Phe Ala
            180                 185                 190

Gln Asn Asp Glu Met Ala Leu Gly Ala Ile Lys Ala Ile Glu Ala Ala
            195             200                 205

Asn Arg Gln Gly Ile Ile Val Val Gly Phe Asp Gly Thr Glu Asp Ala
            210                 215                 220

Leu Lys Ala Ile Lys Glu Gly Lys Met Ala Ala Thr Ile Ala Gln Gln
225                 230                 235                 240

Pro Ala Leu Met Gly Ser Leu Gly Val Glu Met Ala Asp Lys Tyr Leu
                245                 250                 255

Lys Gly Glu Lys Ile Pro Asn Phe Ile Pro Ala Glu Leu Lys Leu Ile
                260                 265                 270

Thr Lys Glu Asn Val Gln
            275
```

COMPOSITIONS, METHODS, AND SYSTEMS FOR AFFINITY-BASED PROTEIN IDENTIFICATION AND PURIFICATION

CROSS-REFERENCE TO RELATED APPLICATIONS

This application claims benefit of priority pursuant to 35 U.S.C. § 119(e) of U.S. provisional patent application No. 62/468,323 filed on Mar. 7, 2017, U.S. provisional patent application No. 62/559,143, filed on Sep. 15, 2017, and U.S. provisional patent application No. 62/627,349, filed on Feb. 7, 2018, all of which are hereby incorporated by reference in their entirety.

SEQUENCE LISTING

A sequence listing submitted in computer readable format is hereby incorporated by reference. The computer readable file is named P265260_WO-US_01-504865-00008_SL.txt, is 51,110 bytes in size, created on Nov. 5, 2019.

FIELD

The disclosed processes, methods, and systems are directed to peptide sequences useful in expression, identification, and isolation of recombinant proteins and peptides.

BACKGROUND

Much of bio-medical research relies on the ability to identify, express, engineer, isolate, and analyze proteins in a clinical or research laboratory setting. In some cases, this requires a large array of different methods, kits, and reagents. While recombinant proteins are useful in analyzing a protein's function by making mutations in its sequence, it must be isolated and purified in order to test that function. There are a variety of reagents and systems for purifying proteins, but existing methods have important disadvantages. To minimize these disadvantages researchers are required to use multiple techniques, which result in increased costs and time.

There is a need for improved compositions, methods, systems, and kits for enhancing the expression, isolation, and identification of proteins, especially recombinant/engineered proteins.

SUMMARY

The present disclosure is directed to compositions, proteins, nucleic acids, methods, and systems for purification and/or detection of recombinant proteins. In many embodiments, a Ribose Binding Protein is separated at or near its carboxyl end to generate two fragments that bind specifically, and with high affinity. When one or the other fragment is immobilized to a solid support, this specific interaction is robust and is able to withstand exposure to a wide range of pH environments. The disclosed interaction is also stable in a variety of denaturing conditions. The interaction may be further stabilized by addition of D-ribose. Also disclosed is a system that enhances recombinant protein expression and solubility.

The disclosed compositions, proteins, nucleic acids, methods, and systems are novel, non-obvious, and have great and varied utility. For example, the disclosed compositions may be useful in creating a variety of affinity purification resins, as well as various applications involving the expression, purification, or isolation of tagged recombinant proteins, including without limitation western blots, ELISAs, immunocytochemistry, etc.

BRIEF DESCRIPTION OF THE DRAWINGS

FIG. 3 is a nucleotide sequence of SEQ ID NO: 93, one embodiment of the RP Tag Large protein including tag, linkers, and engineered Cys residue.

FIG. 4 amino acid sequences of various embodiments of the RP Tag proteins including SEQ ID NO:94 (Sequence 1), SEQ ID NO: 3 (Sequence 2), and SEQ ID NO:13 with a glyicine serine tail (Sequence 3).

DETAILED DESCRIPTION

Figure 1:
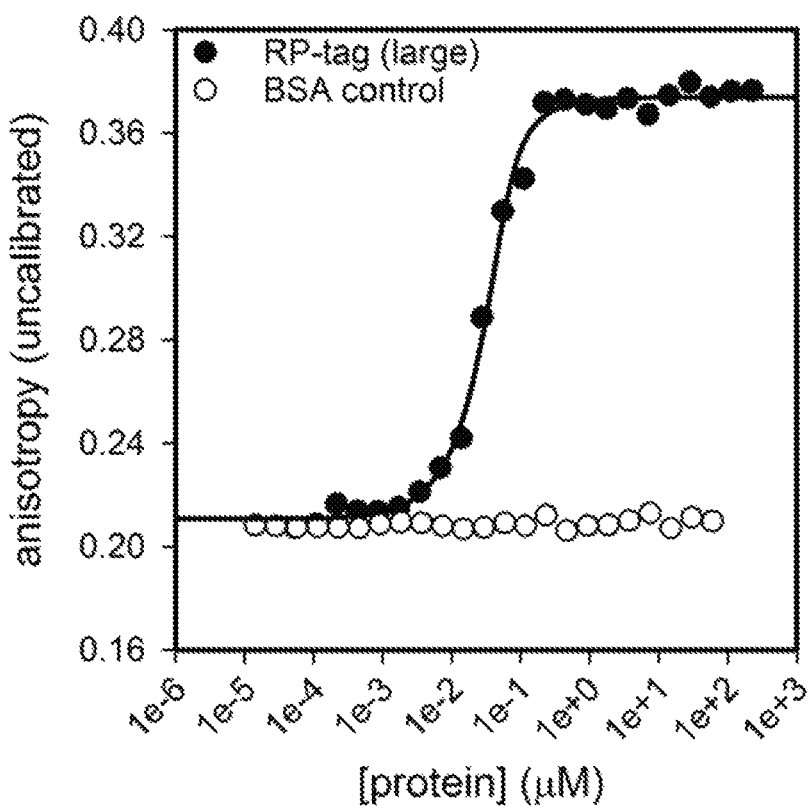
FIG. 1 is a graph depicting the interaction of one embodiment of the disclosed system, used to determine an affinity between one embodiment of RP-Tag Small and one embodiment of RP-Tag Large.

Disclosed herein are compositions, methods, systems, and kits useful in the expression, identification, and isolation/purification of engineered proteins. In some embodiments, a two-part peptide tag system is disclosed that is useful for affinity purification and/or specifically identifying tagged proteins. The system is also useful in aiding solubility and expression of recombinant proteins while also providing a tag for identifying and isolating/purifying the recombinant protein. The disclosed system is also useful in performing protein interaction studies.

The disclosed two parts of the tag system are derived from bacterial ribose binding (RB) protein. In some embodiments, the disclosed ribose binding protein (RP-Tag, RPtag, Tag protein, Tag peptide, RPtag protein, RPtag peptide may be used to describe the presently disclosed proteins and peptides) is from the thermophilic bacterium *Thermoanaerobacter tengcongensis* (also referred to as *C. subterraneous*), and may be more stable than other RB proteins. However, other sources of RB proteins, for use with the disclosed RB-Tag system, are appropriate. In many embodiments, the disclosed ribose binding protein sequence may be altered/mutated to remove a putative N-terminal periplasmic localization sequence. In most embodiments, the disclosed RB-Tag sequences may also be altered to change naturally-occurring cysteine residues (Cys; for example, Cys 102) to serine residues (Ser; sequence of the intact protein below, Seq. 94).

Full length sequence of RB Protein from *Thermoanaerobacter tengcongensis* lacking the putative periplasmic localization sequence and including a C102S mutation is shown blow. A break, //, identifies, generally, the separation between the two fragments (RPtag(large) and RPtag(small))—SEQ ID NO: 94.
MKEGKTIGLVISTLNNPFFVTLKNGAEEKAKEL-GYKIIVEDSQNDSSKELSNV EDLIQQKVDVLLINPVDSDAVVTAIKEAN-SKNIPVITIDRSANGGDVVSHIASD NVKGGE-MAAEFIAKALKGKGNVVELEGIP-GASAARDRGKGFDEAIAKYPDIK IVAKQAADFDRSKGLSVMENILQAQPKI-DAVFAQNDEMALGAIKAIEAANRQ GIIV-VGFDGTEDALKAIKEGKMAA-TIAQQPALMGSLGVEMADKYLK// GEKIPNFIPAELKLITKENVQ PRtag Proteins The disclosed RB protein, from thermophilic bacteria, is very stable. In many cases, the disclosed RB protein has a melting temperature of over 100° C. The disclosed protein is also highly resistant to denaturants like guanidine hydrochloride and urea. Applicants have identified a peptide at the C-teminus of the RB protein that binds with very high affinity. Specifically, Applicants truncate the RB protein sequence at position 257, generating two RP-Tag fragments. The two fragments are referred to as RP-Tag Large (a.a. 1-257) and RP-Tag Small (a.a. 258-279; GEKIPNFIPAEL-KLITKENVQ; SEQ ID NO: 13). When expressed independently, the two fragments may be engineered to have short linker sequences at the C- and/or N-termini. The disclosed fragments may include any number of additional amino acids from the RB sequence (i.e. RP-Tag Large may comprise a.a. 1-260; and RP-Tag small may comprise a.a. 250-279), or amino acids from some other source, at the N- and/or C-termini. Additionally, the disclosed RP-Tag proteins may include fewer RB residues (i.e. RP-Tag Large may include a.a. 5-250, instead of a.a. 1-257).

Various embodiments of the disclosed proteins and peptides may include one or more changes selected from one or more of natural amino acid, synthetic amino acid, fusion, conjugation, derivatization, mutation, substitution, addition, or deletion. In many embodiments, the sequence of the disclosed RP-Tag proteins and peptides may possess less than 100% identity to the sequence of tte RB protein, for example less than 90%, 85%, 80%, 75%, 70%, 65%, 60%, 55%, or 50%, and greater than about 50%, 60%, 70%, 80%, 90%, or 95%. In some embodiments, the disclosed proteins and peptides may comprise one or more synthetic amino acids or residues.

The disclosed proteins and peptides may include one or more deletions. In some embodiments, the deletions may be truncations at one or both termini of the protein or peptide. In some embodiments, such deletions may aid in enhancing affinity or reducing affinity. The disclosed deletions may include from about 1 to about 20 contiguous, or non-contiguous residues, for example more than about 2 aa, 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, or 19 aa, and less than about 20 aa, 19 aa, 18 aa, 17 aa, 16 aa, 15 aa, 14 aa, 13 aa, 12 aa, 11 aa, 10 aa, 9 aa, 8 aa, 7 aa, 6 aa, 5 aa, 4 aa, 3 aa, or 2 aa.

The disclosed proteins and peptides may have one or more amino acid changes in one or more functional and/or structural domains. For example, RPtag(small) peptide may include a domain that may aid in binding with another protein or peptide, such as RPtag(large), and another domain for stabilizing a bi-molecular complex (for example RPtag (large): RPtag(small)) or for stabilizing or destabilizing an intermediate form.

Binding Affinity

The disclosed RP-Tag proteins and peptides bind with specificity and with high affinity to each other. In many embodiments the equilibrium binding constant, $K_d$, is in the nanomolar range, for example less than about 100 nM, 10 nM, 1.0 nM, 0.1 nM, 0.01 nM. In many embodiments, the $K_d$ is less than about 10 nM. As demonstrated below, in FIG. 1, Applicants have measured a $K_d$ of about 8 nM for one embodiment, and 2 nM for another embodiment. In many embodiments, one or more changes in the amino acid sequence may aid in enhancing or reducing binding affinity. Binding affinity may be altered by adjusting the kinetics and/or equilibria of the binding reaction. This adjustment may be accomplished by modifying the amino acid sequence of one or both RPtag proteins and/or modifying the composition of a buffer system. The interaction of these two proteins is specific and there is no detectable binding of the RP-Tag proteins to BSA.

Amino acid substitutions in the sequence of RPtag(small) peptide are useful in modulating the affinity for RPtag (large). In some embodiments, amino acid substitutions in the sequence of RPtag(large) peptide may be useful in modulating the affinity for RPtag(small). For example, amino acid substitutions at positions 2E, 18E, and 21Q may aid in increasing the affinity of RPtag(small) for RPtag (large). In some embodiments, the substitutions may be alanine, while in other embodiments enhancing mutations may be other than alanine, and at positions other than 2, 18, and 21.

Buffer Systems

Affinity and specificity may be changed depending upon the surrounding environment, for example the solution wherein binding occurs. In many embodiments, affinity may be affected by adding one or more organic solvents, alcohols, disulfide reducers, aromatics, sugars, salts, denaturants, detergents, etc. In some embodiments, the buffer system for the disclosed proteins and peptides may include one or more of DMSO, EtOH, MeOH, acetone, glycerol, BME, DTT, PG, imidazole, ribose, sorbitol, NaCl, KCl, $NH_4SO_4$, $MgCl_2$, $CaCl_2$, $NiCl_2$, $MnSO_4$, Gdn-HCl, urea, Tween20, TritonX-100, SDS. In some embodiments, salts may enhance or lessen binding affinity. In one embodiment, kosmotropic salts may aid in enhancing binding affinity, while chaotropic salts may decrease binding affinity. In many embodiments, NaCl and KCl may aid in stabilizing the interaction of RPtag(large) and RPtag(small). In these embodiments, the buffer may include a salt concentration of between about 5 mM and 5 M. In many embodiments, the effect on affinity may be similar for all peptides and protein, or may be different depending upon the sequence of the protein and/or peptide. In other embodiments, one or more compounds or molecules may be used to disrupt and/or lessen the disclosed interactions. In one embodiment, a pH buffer, denaturant, polyion, or imidazole may be used to disrupt binding. In these cases, the solution may help elute a target protein or target peptide from a solid support.

Disclosed herein are buffer systems for promoting and for disrupting interaction between the disclosed RPtag proteins. In some embodiments, buffers that promote binding may have pH between about 4 and 10, and a kosmotropic salt between about 10 mm and 5 M. In some embodiments, preferred buffers include about 0.1 M tris or phosphate pH 8.0, 3 M NaCl for binding. In some embodiments, buffers that may disrupt a RPtag complex may have a pH greater than about 10 and less than about 4, may comprise a chaotropic salt, may comprise imidazole, and combinations thereof. In some embodiments, preferred buffers include about 0.1 M tris or phosphate pH 8.0, 3 M imidazole for elution.

Protein Expression

The large RP-Tag protein is also useful in aiding the stability and expression of other protein sequences to which it is fused. In many embodiments, fusion proteins, having the sequence of the Large RP-Tag protein may express to greater than about 400 mg/L when expressed in bacteria (for example BL21(DE3) *E. coli*). In some embodiments, high expression of stable, functional, fusion proteins may be achieved with pH-stat fed-batch bioreactor and methods of using the stated bioreactors.

The disclosed RP-Tag proteins may be expressed in or from a variety of prokaryotic and eukaryotic cell and systems. In some embodiments, the RP-Tag protein is expressed from a yeast cell, bacterial cell, mammalian cell, insect cell, plant cell, etc., such as *Saccharomyces cerevisiae, Pichia pastoris*, Human Embryonic Kidney cell, Chinese Hamster Ovary Cell, *Spodoptera frugiperda*, etc. or extracts thereof. In some embodiments, the disclosed proteins and peptides may be chemically synthesized.

The disclosed RP-Tag interaction may be stabilized in the presence of ribose. Ribose is bound by the large RP-Tag protein, and its interaction with RP-Tag Large may help to stabilize the structure of this fragment and may also help to stabilize interaction between the two RP-Tag fragments.

Solid Supports

The disclosed Tag proteins may be affixed to a solid support to aid in isolating the complement Tag protein. For example, in some embodiments, the Large RP-Tag protein may be affixed to a matrix for a column, and a fusion protein comprising the Small RP-Tag protein may be combined with the matrix (either in solution [or batch processing], or by adding the RP-Tag fusion protein to a column comprising the solid matrix/RP-Tag protein, as in Example 1, below) to isolate and purify the fusion protein. In other embodiments, the Small Tag protein is affixed to the column matrix to aid in binding a fusion protein comprising the Large Tag protein. Thus, a target protein may be fused to either the Small or Large Tag protein, and may be fused to either the C- or N-terminus of either protein. In some embodiments, the fusion protein may include a linker sequence between the Tag sequence and that target protein sequence. In many embodiments, this linker sequence may be from about 1 a.a. to about 30 a.a. in length. In some embodiments, this linker sequence may add functionality to the fusion protein, for example by introducing a labelling sequence, cleavage sequence, or recognition sequence.

Suitable resins for immobilization may comprise a bead of polymeric matrix (for example but not exclusive to: agarose, Sepharose, dextrans, acrylamide, bisacrylamide, silica, methacrylate, and various mixtures and cross linking formulations thereof), along with a chemistry for coupling to the peptide or protein (e.g. an aldehyde, maleimide, N-Hydroxysuccinimidyl ester, halo-acetyl group, sulfhydryl (activated or free), hydrazide, hydrazine, amine, alkyne, azide, carboxyl group, or other moiety commonly known in the art), that may or may not be on the end of a spacer which is attached to the polymer matrix.

A variety of methods may be used to affix an RP-Tag protein to a solid support. In some embodiments, it may be useful to add one or more amino acids to the RPtag protein to aid in linking the RPtag protein to the solid support. In other embodiments, the linkage may be chemical, for example via cysteine, di-sulfide bond, primary amines, amide bonds, or other covalent chemistry. In one embodiment, a Cys residue may be engineered in the RPtag protein to allow the protein to link a solid support via a thioether bond (e.g. using SULFOLINK™ technology from ThermoFisher Scientific). By another method, the RPtag protein or peptide might be immobilized via free amine groups to aldehyde resin, thus forming an imine, and then reduced via sodium cyanoborohydride to form a stable secondary amine.

Modifications—Tags, Linkers, Reporters, Etc.

The disclosed RPtag proteins may be labeled to aid in visualizing or locating one or both proteins. Suitable label and methods of labeling proteins are well known in the art. In some embodiments, specific amino acid residues may be targeted for attaching one or more labels. In other embodiments, target sequences (for example the linker sequences described above) may be added to the RPtag proteins to facilitate labeling. In some embodiments the label is visible (e.g. dyes or fluorescent labels), or the label may be visualized with detector equipment (e.g. radioactive labels, fluorophore, radioactive isotopes, chromophores, metals for electron microscopy like gold and iron, quantum dots, etc.), or other labeling techniques well known to those skilled in the art. In one embodiment, the RPtag protein is labeled with rhodamine.

Mutations may be introduced in the Tag protein using a variety of methods well known to those of skill in the art. In some embodiments, as discussed above, additional amino acids may be added to the Tag protein sequence to create linker sequences that may be useful in adding a label, tag, or other adduct to the protein. In other embodiments, the amino acid sequence of the Tag protein may be mutated to change one or more amino acid residues. In these embodiments, it may be useful to create specific amino acid substitutions to help increase or decrease affinity between the two Tag proteins. As one example, a Small mutant Tag protein may be engineered to have greater affinity for the Large Tag protein to aid in displacing, or competing away the disclosed Small Tag protein. In other embodiments, amino acid mutations may help to lower the affinity of the Large Tag protein for the Small Tag protein.

Protein Stability

The disclosed Tag protein affinity system is resistant to conditions that normally disrupt protein-protein interactions. Typically, protein-protein interactions are sensitive to disruption by changes in pH, ion concentrations, temperature, and denaturant concentration. For example, typical protein-protein concentrations may be disrupted by increasing or decreasing the pH of a solution containing a protein-protein interaction above about 8.0 pH or below about 6.5 pH. In many embodiments, the disclosed protein-protein interaction is stable in pH above 8.0 pH and below 6.5 pH. In some embodiments, the disclosed interaction is stable in high concentrations of one or more denaturant compounds (e.g. urea, guanidine, etc.), wherein the concentration of denaturant is greater than about 1M.

Definitions

"Polypeptide," "protein," and "peptide" are used interchangeably to refer to or describe a linear or branched chain of amino acid monomers linked by peptide bonds. Individual positions within those chains may be referred to as a "residue," or "amino acid." The disclosed polypeptides, proteins, and peptides may be of any length and comprise any number of natural or synthetic amino acids.

"Homology," "homologous," "identity," "identical," "similar," and "similarity" as used herein refer to a degree of nucleic acid and/or amino acid sequence similarity between two optimally aligned nucleic acid or peptide molecules. Percent homology and identity are determined by comparing positions in two or more sequences, aligned for purposes of such a comparison. In many cases, one of skill in the art can use one or more computer applications to determine such values, for example BLAST. Comparing equivalent positions in different sequences may identify the same residue or nucleotide—this is referred to as identity. In contrast, were the equivalent positions have amino acid residues with similar characteristics or properties (e.g. size, polarity, charge, etc.) the amino acids may be homologous but not identical.

Non-covalent interactions refer to interactions based on non-covalent forces, such as ionic, hydrophobic and hydrogen bond-based interactions. Non-covalent interactions do not include interactions based upon two atoms sharing electrons.

Affinity may be expressed in terms of the equilibrium binding constant $K_a$, or dissociation constant, $K_d$ or $K_D$. $K_d$ is expressed as a concentration and can be determined by measuring the association rate constant, $k_a$, and dissociation rate constant, $k_d$, and determining their ratio ($k_d/k_a$). One of skill in the art is readily able to determine affinities using a variety of techniques and methods. Typically, one of skill in the art may determine an equilibrium constant or $K_d$, by varying input concentrations of one component (here, [RP-Tag Large] or [RP-Tag Small]) to achieve equilibrium, and measuring the relative concentration of the complex (here [RP-Tag Large:RP-Tag Small]). Other techniques are able to monitor such interactions in real-time to determine on-rates and off-rates.

EXAMPLES

Example 1—Column-Based Interaction

One embodiment of the disclosed RP-Tag system was tested by creating a column with one component bound to a solid, agarose-based matrix. In these experiments, a Sulfo-Link™ Immobilization kit (ThermoFisher scientific) was used to affix RP-Tag Large to a solid support, according to the manufacturer's instructions. For these experiments, an N-terminal linker was added to RP-Large that included a Cys residue. One of skill in the art is able to select various techniques and chemistries to aid in affixing either RP-Tag protein to a solid support matrix.

Figure 2:
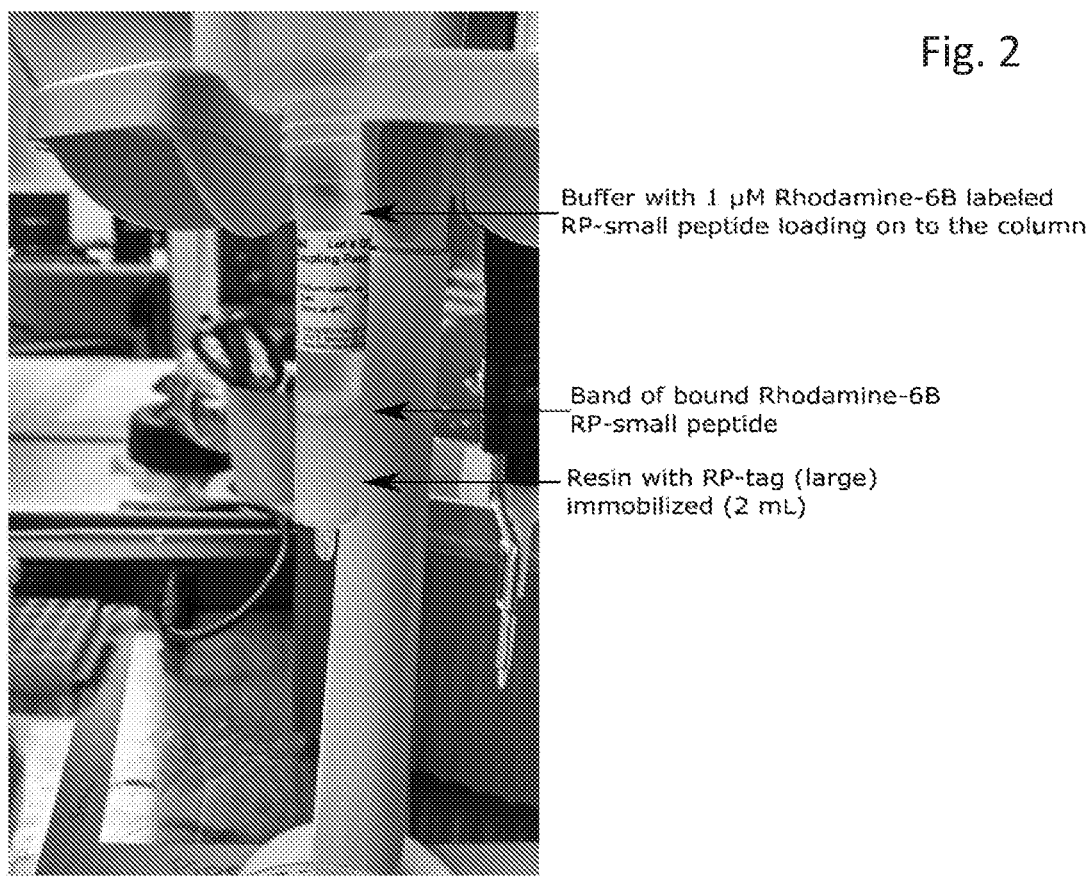
FIG. 2 shows a column comprising one embodiment of the disclosed compositions.

The amount of protein linked to the column was determined using a BCA assay with Bovine Serum Albumin (BSA) as a standard. This showed that 4.5 mg RP-Tag Large was immobilized onto 2 mL of the SulfoLink™ resin to create a RP-Tag Large-linked resin. The linked resin was poured into an included column and the column capped with a frit included in the kit (see photos in FIG. 2). The column was equilibrated with several volumes of 50 mM Tris pH 8.5, 150 mM NaCl, 5 mM EDTA.

Methods

An *E. coli* codon-optimized gene encoding tteRP-Tag Large was synthesized using solid-state methods. This gene was then cloned into a pET-28a(+) expression vector.

Labeled and unlabeled RP-Tag Small proteins were synthesized solid state, resuspended in DMSO (1-10 mM final peptide concentration) and stored at −20° C. until needed. Prior to use, the proteins were thawed and diluted into an appropriate buffer.

RP-Tag Large Expression and Purification

Chemically competent BL21(DE3) *E. coli* were transformed with 50 ng expression plasmid, streaked onto Luria Broth (LB)+50 mg/L kanamycin agar plates and grown at 37° C. overnight. Single colonies were then picked and grown in Fernbach flasks in LB+50 mg/L kanamycin at 37° C. with continuous shaking at 225 RPM until $OD_{600}$=0.6. The temperature was then dropped to 25° C. and the cultures induced with 20 mg/L Isopropyl β-D-1-thiogalactopyranoside (IPTG) and grown for an additional 18 h.

Cultures were submitted to centrifugation to pellet bacterial cells. Supernatant was discarded and cell pellets resuspended in 20 mM sodium phosphate pH 8.0, 300 mM NaCl, 10 mM 2-mercaptoethanol, and 10 mM imidazole. Cells were lysed enzymatically (Lysozyme, DNAaseI, 5 mM $MgSO_4$ 1 hour on ice), cell debris pelleted by centrifugation, and the clarified supernatant loaded onto a NiNTA column equilibrated with the lysis buffer. Protein was then eluted with a step gradient of imidazole (10 mM-250 mM), and protein-containing fractions pooled and dialyzed against 20 mM sodium phosphate 8.0, 150 mM NaCl, and 10 mM 2-mercaptoethanol.

Dialyzed protein samples were flash frozen in liquid nitrogen and stored at −80° C. until use. Concentrations were determined either using a BCA assay using Bovine Serum Albumin as a standard, or by $A_{280\ nm}$ using a calculated $\varepsilon_{280}$=4,470 $M^{-1}$ $cm^{-1}$. For pH-stated fed-batch bioreactor protocols, an identical protocol was used except cultures were grown in a 10-L New Brunswick Bioreactor, LB was additionally supplemented with 20 g/L glucose and 0.6 g/L magnesium sulfate, and pH was maintained between 6.85 and 6.95, adding 50% glucose and 1.5% MgSO4 mixture if the pH increased over 6.95 by peristaltic feed pump, and 30% ammonium hydroxide if pH dropped below 6.85 by peristaltic feed pump. Fed-batch cultures were induced at $OD_{600}$=6 with 1 mM IPTG. Purified protein was >95% pure as judged by SDS-PAGE stained with coomassie brilliant blue R-250.

Example 2—Solution State Affinity 50 nM of RP-Tag Small (see Sequence 3, below) with an N-terminal Rhodamine B label was incubated with increasing concentrations of either RP-Tag Large (see Sequence 2) or Bovine Serum Albumin (BSA) in 50 mM Tris pH 8.0, 150 mM NaCl, 10 mM 2-mercaptoethanol, and 0.005% Tween 20 for 5 min in black 96-well plates at room temperature. Anisotropy was then measured, and a $K_d$ calculated by fitting the data to the equation $f=y_0+(y_{max}-y_0)*(P_{tot}+x+K_d-\sqrt{(P_{tot}+x+K_d)^2-4*P_{tot}*x})/(2*P_{tot})$, where $y_0$ is the baseline anisotropy, $y_{max}$ is the maximum anisotropy, $P_{tot}$ is the fixed concentration of labeled peptide used, x is the variable concentration of protein used, and $K_d$ is the measured $K_d$. Fitting of the data resulted in a calculated $K_d$ of 8 nM for this interaction, and detected no binding to BSA (see FIG. 1).

Binding of RP-Tag Small to Immobilized RP-Tag Large 25 mL of 1 µM Rhodamine-6B labeled RP-Tag Small, in 50 mM Tris pH 8.5, 150 mM NaCl, 5 mM EDTA, was flowed over the column of immobilized RP-Tag Large protein. RP-Tag Small bound the column and formed a visibly bright red band (rhodamine B) at the top of the resin (see FIG. 2). This red band did not appreciably diffuse even after extensive washing (>20 column volumes), and was stable for >1 week at room temperature.

Example 3—Stability of RP-Tag Small:RP-Tag Large Interaction

Table 1 summarizes results from elution tests using a variety of conditions. Briefly, after binding, the RP-Tag Small red band was not observed to appreciably diffuse and/or elute after washing the column (and band) with various solutions. For these tests, 10 mL (5 column volumes) of various buffers were added to the column. The tested buffers ranged from about pH 1.5-13.7 and about 1 M sodium hydroxide. These results (see FIG. 2) suggest that this interaction (between RP-Tag Small and Large) possesses among the widest compatible pH ranges known for affinity resins.

TABLE 1

| Elution Buffer (5 column volumes) | Result |
| --- | --- |
| 1M sodium hydroxide | No band diffusion/elution |
| 0.1M sodium phosphate pH 13.7 | No band diffusion/elution |
| 0.1M sodium phosphate pH 13.0 | No band diffusion/elution |
| 0.1M sodium phosphate pH 12.0 | No band diffusion/elution |
| 0.1M Tris pH 8.5 | No band diffusion/elution |
| 0.1M Tris pH 8.0 | No band diffusion/elution |
| 0.1M Tris pH 7.5 | No band diffusion/elution |
| 0.05M sodium acetate pH 4.6 | No band diffusion/elution |
| 0.1M glycine pH 3.5 | No band diffusion/elution |
| 0.1M glycine pH 2.5 | No band diffusion/elution |
| 0.1M glycine pH 1.5 | Complete band elution |
| 0.1M Tris pH 7.5 + 6M guanidine hydrochloride | Complete band elution |
| 0.1M Tris pH 7.5 + 6M guanidine hydrochloride + 10 mM D-ribose | partial band elution, significant diffusion within column |
| 0.1M Tris pH 7.5 + 6M guanidine hydrochloride + 100 mM D-ribose | no band elution, significant diffusion within column |
| 0.1M Tris pH 7.5 + 6M guanidine hydrochloride + 1M D-ribose | No band elution, minor diffusion within the column |
| 0.1M Tris pH 7.5 + 100 µM unlabeled RP tag peptide | Partial band elution, slight diffusion throughout the column |

Table 1. Summary of elution trial data. The test system used was a column equilibrated with 50 mM Tris pH 8.5, 150 mM NaCl, 5 mM EDTA, and applied 25 mL 1 µM Rhodamine-6B labeled RP-small peptide in the same buffer. In cases where D-ribose was used, the indicated concentration was also included in the equilibration and loading buffer.

Diffusion and/or elution of the rhodamine-labelled band required subjecting the column to very strong buffers. For example, elution was seen with a buffer comprising 100 mM glycine and pH 1.5, as well as a buffer comprising 0.1 M Tris pH 7.5+6 M Guanidine-HCl. Even after elution with these strong buffers, the column was able to be re-equilibrated with neutral buffer (specifically 50 mM Tris pH 7.5), and its ability to bind RP-Tag Small was restored. These results indicate that the RP-Tag resin can be effectively washed with high concentrations of hydroxide (e.g. 1 M sodium hydroxide), low pH buffer (e.g. 100 mM glycine pH 1.5) and high concentrations of denaturants (e.g. 6 M guanidine hydrochloride), and still be regenerated to a functional state.

Example 4—Binding Under Denaturing Conditions

Conditions were investigated in which the RP-Tag Large resin would bind RP-Tag Small proteins under strongly denaturing conditions (e.g. 6 M Gdn-HCl). RP-Tag Large's ability to bind ribose was investigated. RP-Tag Small was bound as described above with 10 mM, 100 mM, and 1 M D-ribose. All concentrations of D-ribose significantly slowed diffusion of the bound rhodamine band with 5 column volumes (CVs) washing. About 100 mM D-ribose stopped virtually all peptide elution from the column, while at 1 M D-ribose even diffusion within the column was reduced to modest levels.

It should be noted that no tested concentration of D-ribose was able to stop diffusion of the rhodamine band entirely. In 6 M guanidine the capacity of the column is likely reduced and extensive washing would almost certainly cause the target to leach to some extent. Nonetheless, these results indicate that the inclusion of increasing concentrations of D-ribose can stabilize RP-tag under denaturing conditions, and make it an effective purification tool even with high concentrations of denaturants.

Example 5—RP-Tag Small:Large Competition

Conditions under which the labeled RP-Tag Small could be eluted at neutral pH were investigated. These experiments were directed to eluting bound RP-Tag Small using unlabeled RP-Tag Small—that is, disrupting the complex by competition. For these experiments, 100 µM of unlabeled RP-Tag Small in 0.1 mM Tris pH 7.5 was used. Slight diffusion of the rhodamine band within the column, was observed. In addition, these competition experiments successfully eluted a small amount of labeled RP-Tag (small) protein from the column.

These results demonstrate that bound RP-Tag proteins may be competed off the column under neutral conditions. In some embodiments, higher affinity RP-Tag proteins may be engineered to help compete with one or more of the existing RP-Tag proteins. In some embodiments, the affinity of the interaction may be modulated by mutating one or more residues to raise or lower the interaction's strength/affinity. In some embodiments, a closely related protein or peptide may be used for completion and/or a multimeric peptide used.

Example 6—Equilibrium Binding

Equilibrium binding affinities ($K_d$) of the native RPtag (large)/RPtag(small) interaction was compared to a commonly used, commercially available epitope tag antibody and its corresponding tag by fluorescence anisotropy (mouse monoclonal antibody purchased from ThermoFisher Scientific (4E3D10H2/E3)). In these studies, the tag sequence was GHHHHHH (SEQ ID NO: 1) with an N-terminal rhodamine B.

The indicated concentrations of RPtag (large) and an anti-His tag antibody (4E3D10H2/E3 purchased from ThermoFisher Scientific) were incubated with 1 nM rhodamine labeled native RPtag (small) peptide and 6×His peptide (Rhodamine-GHHHHHH), respectively, and fluorescence anisotropy measured. BSA incubated with native rhodamine labeled RPtag(small) is included as a control for non-specific binding. Kd's were calculated according to the equation $f=y0+(ymax-y0)*(Ptot+x+Kd-sqrt((Ptot+x+Kd)^2-4*Ptot*x))/(2*Ptot)$, where y0 is the baseline anisotropy, ymax is the maximum anisotropy, Ptot is the fixed concentration of labeled peptide used, x is the variable concentration of protein used, and Kd is the measured Kd. We measured a Kd of 0.2±0.1 nM for RPtag(large) binding RPtag(small), and a Kd of 6±1 nM for the antibody/6×His tag pair. There was no detectable binding of RPtag (small) to BSA up to the indicated concentrations.

Figure 5:
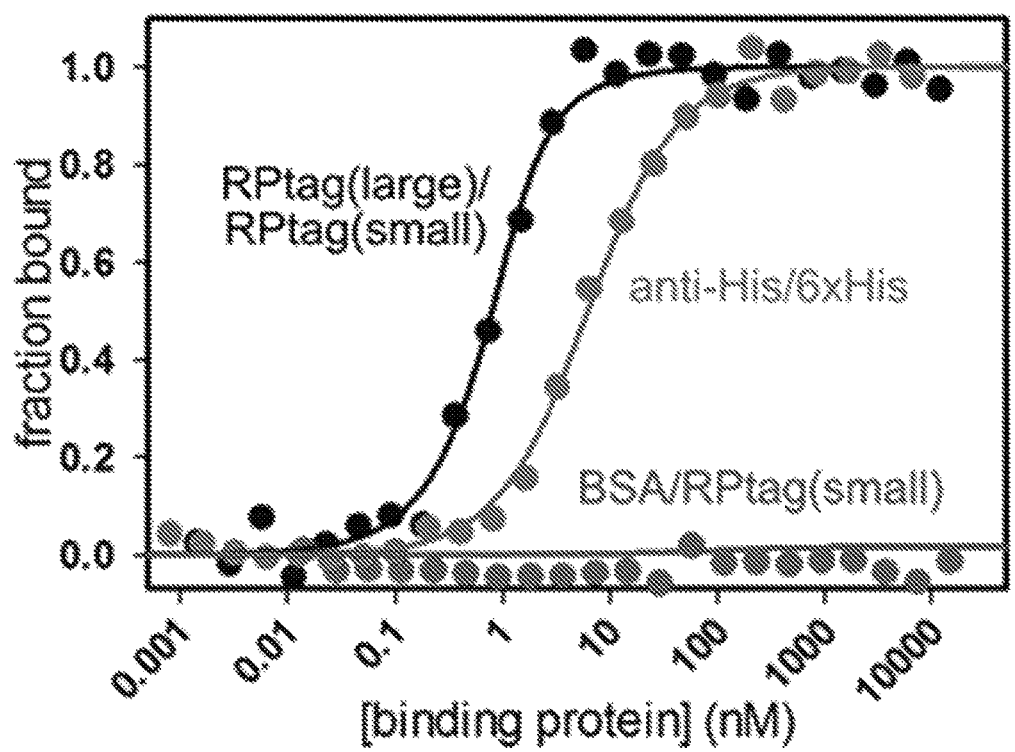
FIG. 5 shows Kd titrations for RP-tag (large) and RP-tag (small) and anti-6×His for a 6×His peptide as measured by fluorescence anisotropy.

Results presented in FIG. 5 demonstrated that the Kd of presently disclosed RPtag system was about 30 times better than that of the commercially available system. Specifically, the calculated Kd for the interaction of RPtag(large)/RPtag (small) was about 0.2 nM, while the Kd for anti-6×His and 6×His is about 6 nM. Further, the interaction between the native RPtag (small) and Bovine Serum Albumin (BSA) was also tested. Here again, no interaction was detected up to 10 µM BSA. This indicated a >50,000 fold selectivity for RPtag (large)/RPtag(small) over non-specific (BSA) interaction.

Example 7—Thermal Stability

The ability of the disclosed proteins and peptides to function after being subjected to thermal stress was also tested. Here again the RPtag (large) and anti-6×His antibody were selected for analysis. Briefly, the RPtag(large) or the anti-6×His antibody was subjected to sequential rounds of boiling and recovery. Specifically, the proteins were subjected to sequential rounds of: 5 min boiling in buffer, followed by recovery for 1 min on ice. After each round of boiling/recovery, the proteins were assayed for binding to their corresponding epitopes and the results plotted.

RPtag (large) and an the anti-His tag antibody (4E3D10H2/E3 purchased from ThermoFisher Scientific) were placed in a solution at about 0.1-1 µM [final] in a buffer of 50 mM Tris pH 8.0, 0.005% Tween20. The protein solutions were repeatedly heated for 5 min at 95° C. and then recovered on ice for 1 min. After each round of heating/cooling, an aliquot was taken and diluted to 100 nM, and incubated with 100 nM either rhodamine labeled RPtag (small) or rhodamine labeled 6x-His peptide (sequence: Rhodamine-GHHHHHH), and the fluorescence anisotropy measured. Fraction binding was calculated via the equation $F=(r-r_{min})/(r_0-r_{min})$ where F is the fraction binding, r is the measured anisotropy, $r_{min}$ is the anisotropy in the absence of binding protein, and $r_0$ is the anisotropy before any boiling trials.

Figure 6:
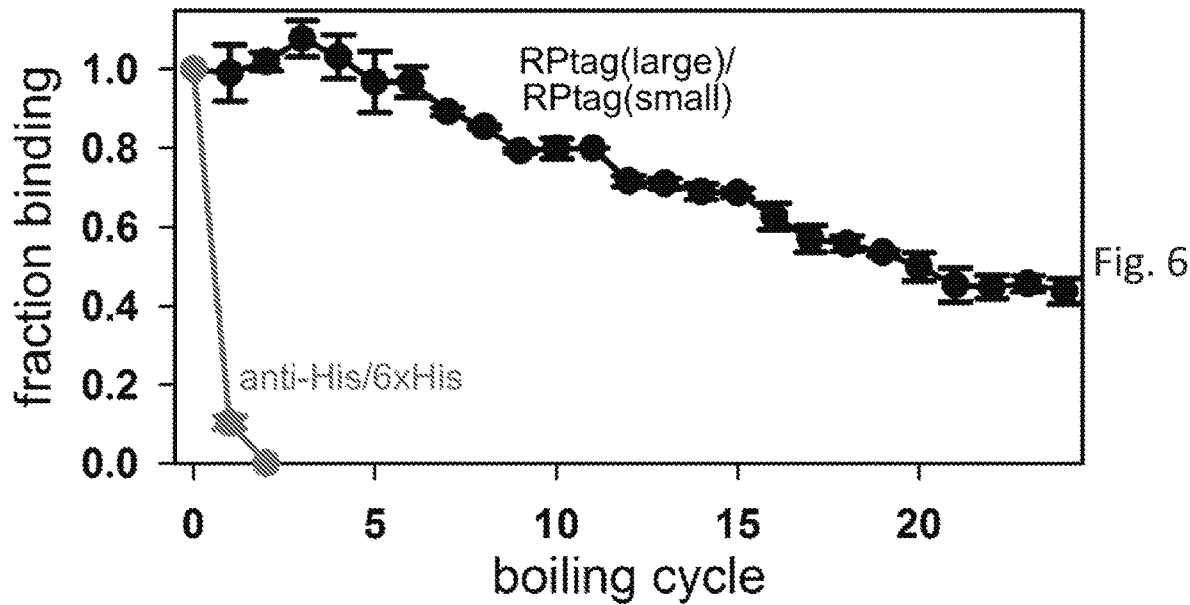
FIG. 6 shows fraction binding component after sequential boiling trials.

As shown in FIG. 6, the anti-6×His antibody lost greater than 90% of its binding capacity after a single round of boiling/recovery. In contrast, FIG. 6 shows that even after 24 rounds, the RPtag (large) possessed more binding capacity than did the anti-6× His antibody after a single round. This indicates that the RPtag (large) system is at least about 10-fold more stable than commercially available products.

A second stress test was performed on the proteins by subjecting them to a 15 min 121° C. autoclave cycle, after which the proteins' function was assayed.

Specifically, RP-tag (large) and the anti-6×His antibody (4E3D10H2/E3 purchased from ThermoFisher Scientific) at 5 µM were subjected to a 15 min 121° C. autoclave cycle with slow exhaust to prevent boiling (total time>100° C.~60 min) in 50 mM Tris pH 8.0, 150 mM NaCl, 1 mM EDTA, 10 mM β-ME, and the $K_d$ measured as above.

Figure 7:
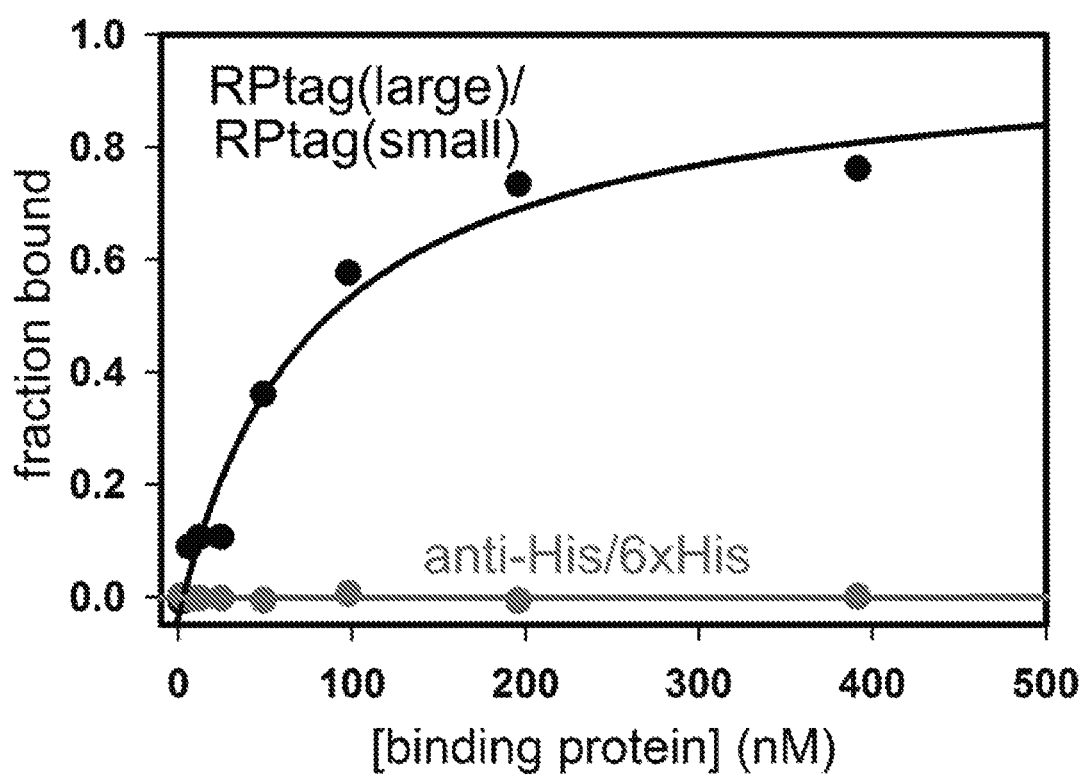
FIG. 7 shows results of autoclave trial for RPtag and antibody.

As expected, the antibody was completely destroyed by this treatment, losing all detectable binding to its target peptide (see FIG. 7). By contrast, RP-tag (large) survived, and maintained a measurable, albeit impaired, binding affinity (Kd=53±24 nM). These results indicate that the RP-tag (large) protein is extremely stable, and that alterations to the protein structure and/or sequence may allow the protein to survive and function in harsh biological or medical environments, for example, where existing systems may be inactivated completely.

Example 8—RP-Tagged Fusion Proteins

To examine the efficacy and specificity of the disclosed proteins, peptides, systems, and methods, fusion proteins were created comprising the disclosed proteins and peptides, and several biomolecules of interest. In one example, RPtag (large) or RPtag (small) were conjugated to a resin of agarose beads. In these experiments, the RPtag sequences were engineered to include N-terminal cysteines, which could be used to covalently bind activated agarose (via the manufacturer's instructions; SulfoLink™ resin purchased from ThermoFisher scientific). Immobilization efficiencies were about 2 mg RPtag (small)/mL resin, and ~38 mg RPtag(large)/mL resin).

Protein Purification

Briefly, codon-optimized DNA coding sequence of each protein was synthesized solid state and then sub-cloned into the pET-28a(+) bacterial expression plasmid. Chemically competent BL21 (DE3) were transformed with the expression plasmids and grown on LB agar+50 µg/mL kanamycin sulfate at 37° C. overnight. Colonies were picked and grown in shaker flasks in LB+50 µg/mL kanamycin sulfate (200 RPM) at 37° C. until OD600=0.6. The temperature was then dropped to 25° C. and expression induced with 1 mM isopropyl µ-D-1-thiogalactopyranoside for 16 hrs. Cells were then harvested by centrifugation and lysed enzymatically with lysozyme and DNAase in 20 mM Tris pH 8.0, 300 mM NaCl, 10 mM imidazole, 5 mM $MgCl_2$. Cell debris was pelleted by centrifugation, and proteins purified by single-step NiNTA chromatography (10 mM-500 mM imidazole step gradient). Concentrations were determined by absorbance using $\varepsilon_{595}=100,000$ $M^{-1}cm^{-1}$.

Column Production

SulfoLink™ resin was purchased from ThermoFisher Scientific. For immobilization of RPtag (large), 200 mg protein/mL resin was incubated at room temperature for 1 hour in Tris pH 8.5, 1 mM EDTA. The RPtag(large)-resin was then washed and incubated in the same buffer+10 mM cysteine. Next, the RPtag(large)-resin was packed into 1 mL FPLC-columns (Gold Biotechnology, Inc., St. Louis, Mo.; see FIG. 8). 38 mg RPtag (large; about 1.3 µmol) and 2 mg RPtag(small; about 0.84 µmol) was immobilized per ml of resin. Note that the RPtag(large) was immobilized to the column via an engineered N-terminal cysteine. The RPtag (small) peptide was immobilized to the resin via an engineered cysteine on its C-terminus (sequence GGC).

Binding Experiments

Figure 8:
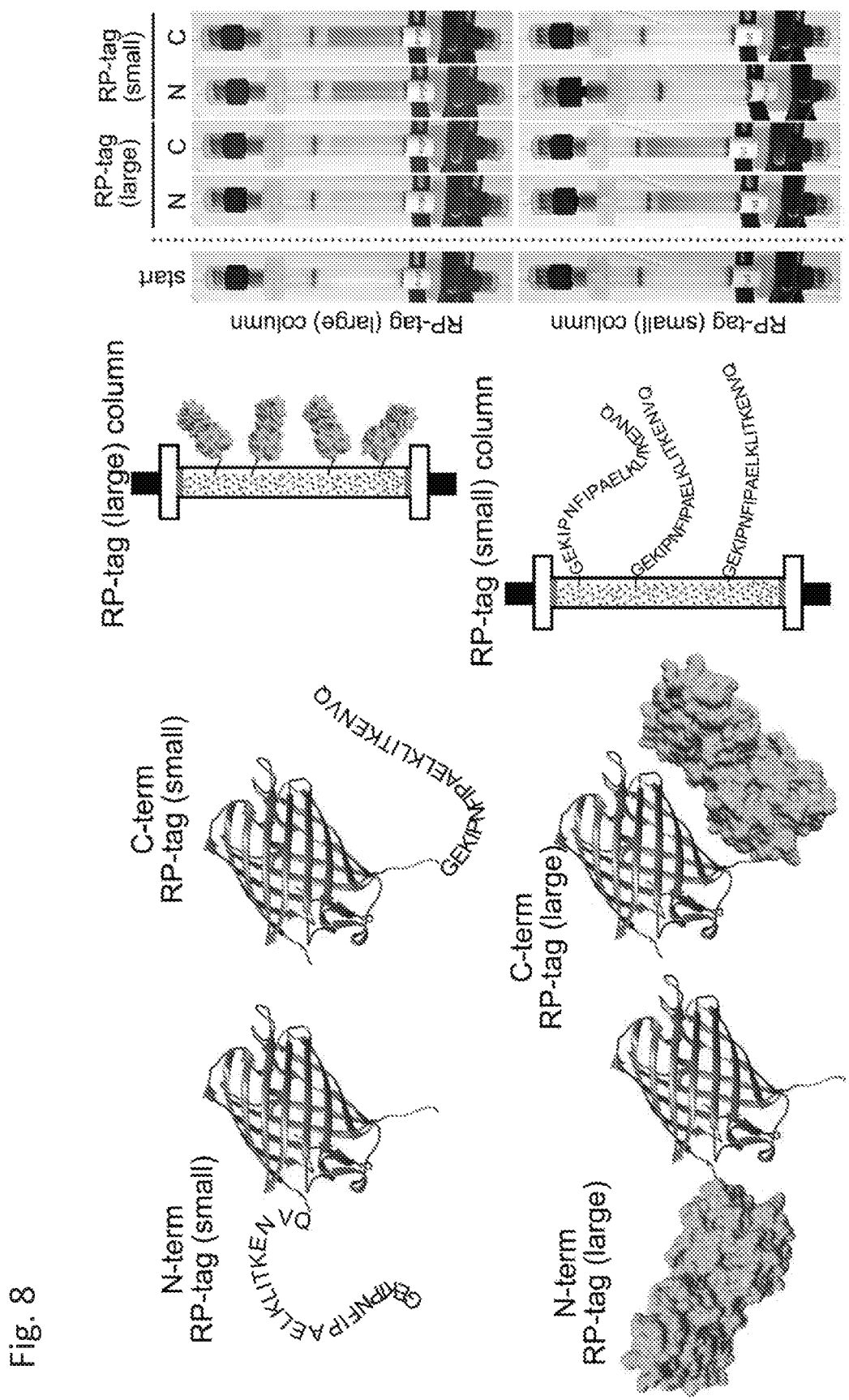
FIG. 8 shows schematic of the fusion proteins and the columns (left), along with photographs of the actual columns (right).

After purification of the tagged proteins, each was applied to its complementary column to evaluate binding. FIG. 8 provides a schematic of the experiment's setup. Briefly, columns were first equilibrated in 20 mM Tris pH 8.0, 150 mM NaCl, 1 mM EDTA (TNE buffer), then 25 mL of 1 µM tagged protein in TNE buffer was applied to the column at a flow rate of 1 ml/min, then washed with 10 mL of TNE buffer. Columns were cleaned with 10 mL 100 mM Glycine pH 1.5 between uses. As shown in photos of the columns at right of FIG. 8, both tags were effective whether attached to the N- or C-termini of the test proteins. These results demonstrate the versatility of the presently disclosed proteins, peptides, methods, and systems.

In some embodiments, immobilization of the RP-tag (small) peptide may allow for the use of a high-solubility, expression and solubility enhancing tag on either terminus of the protein of interest. In other embodiments, immobilization of the RP-tag(large) protein may allow for the use of a small, minimally perturbing tag on the protein of interest, again at either terminus.

As a test for specificity, non-complementary proteins were applied to each column using the same procedure described above. In these experiments, only a small amount of non-specific binding was observed. This background binding is not uncommon and may, in some cases be expected with agarose-based chromatography resins. In some cases, color in the photographs was enhanced to aid in visualization. Where such enhancement was performed, each panel received identical enhancements.

Next, N-terminal and C-terminal fusions of both RPtag (large) and RPtag(small) with a red fluorescent protein (tagRFP) were constructed. TagRFP allows visualization of the proteins (proteins also had an 8×his tag on the opposite terminus to aid in rapid purification). After purification of the tagged proteins, each was applied, separately to its complementary column to evaluate binding.

Briefly, columns were equilibrated in 20 mM Tris pH 8.0, 150 mM NaCl, 1 mM EDTA (TEN buffer), then 25 mL of 1 µM tagged protein in TEN buffer was applied to the column at a flow rate of 1 ml/min. Thereafter, the column was washed with 10 mL of TEN buffer, and the results recorded by photograph (FIG. 8). Columns were cleaned with 10 mL 100 mM Glycine pH 1.5 between uses. Both RPtags(large and small) were effective when attached to either the N- or C-termini of RFP.

Example 9—Mechanistic Studies

To define the mechanism of RPtag (large) and (small) binding, the reaction order of the rate-limiting step was determined.

Results

Figure 9:
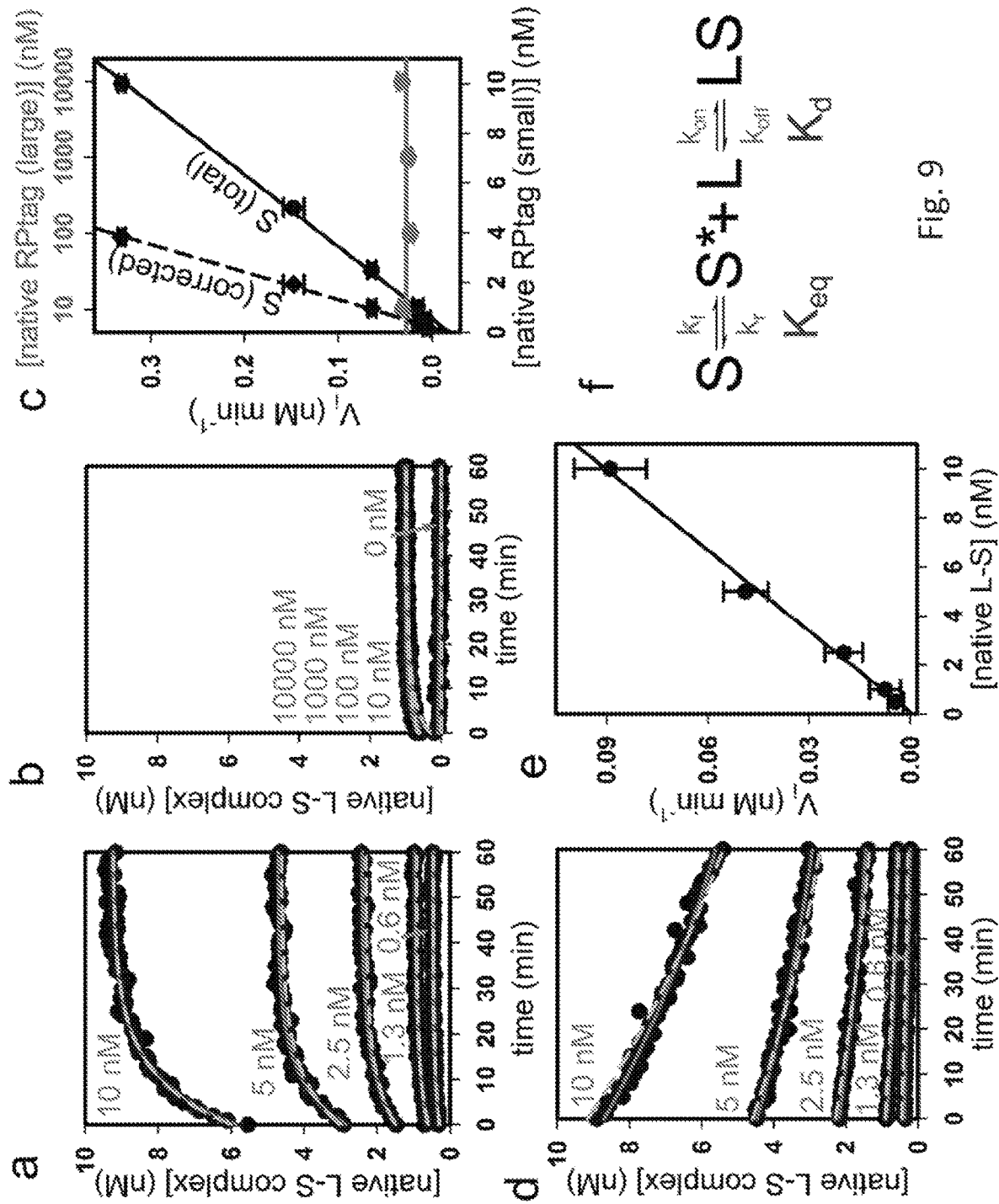
FIG. 9 shows studies of the binding mechanism of RPtag large (denoted as L) and small (denoted as S)

For these experiments, 1000 nM RPtag(large) was incubated with increasing concentrations of native RPtag (small) (from about 0.6 to 10 nM). These experiments identified a linear increase in the initial rate of formation of the complex (RPtag(large):RPtag(small)). This linear increase indicated that the rate limiting step is first order with respect to RPtag(small) (FIG. 9 panels a and c).

Panel a depicts representative association rate kinetics traces varying native RPtag small. Rhodamine labeled RPtag small at the indicated concentration was incubated with unlabeled RPtag large and the association measured by fluorescence anisotropy. L-S complex concentration was calculated by the equation $(r-r_{min})/(r_{max}-r_{min})*[S]$ where r is the measured anisotropy, rmin is the anisotropy in the absence of any RPtag large, rmax is the anisotropy measured in the presence of at saturating RPtag large, and [S] is the total concentration of RPtag small used in the experiment. As shown in FIG. 9, black circles are data, red lines are fits to the single exponential equation $y=y0+A*(1-exp(-b*t))$ where y0 is a baseline offset, A is the amplitude of the curve, and b is the first order rate constant, and t is time. Dashed cyan lines are simulations of the mechanism shown in f using the rate constants detailed herein. The concentrations in the simulations were multiplied by a correction factor of 0.925, which is well within the 90% purity specification of the purchased peptide.

Panel c shows initial velocities of traces represented in panels a (black) and b (red). The first 5 min of data were fit with a line, and plotted as a function of concentration. S(total) is plotted as a function of the total concentration of RPtag small used in the reaction, S (corrected) is plotted as a function of the concentration of S corrected for Keq as detailed herein. The slope of the line using S (total) is 0.035 min$^{-1}$, in much worse agreement with the data and single exponential fit rate constant than the 0.091 min$^{-1}$ slope of the S(corrected) line. Data shown are mean±SE (n=3).

Next, 1000 nM RPtag (small) peptide was incubated with increasing concentrations of RPtag (large) protein (from about 0 to 10,000 nM). These experiments resulted in no change in the rate (except at 0 nM RPtag(large)). These results indicated that the reaction is 0$^{th}$ order with respect to RPtag (large) (FIG. 9 panels b and c).

Panel b presents the representative kinetics traces varying native RPtag large. Indicated concentrations of RPtag large were incubated with 1000 nM RPtag small and anisotropy measured. All calculations were as in panel a.

Taken together, these studies demonstrated that the rate liming step of complex (RPtag(large):RPtag(small)) formation is first order only with respect to RPtag (small), consistent with a unimolecular process. Without wishing to be limited, this suggests the possibility of a conformational change in the RPtag(small) peptide prior to binding. The conformational change being from a "non-binding" (S) to "binding" (S*) state. This conformation change is then followed by a much faster bi-molecular binding event (to RPtag(large)). Again, without wishing to be limited, the data suggest a missing amplitude in the binding kinetics. Specifically, this may represent the proportion of the binding reaction that occurred in the dead time of the instrument (~1 min), and therefore the amount of RPtag (small) that was already in the S*, binding state at the start of the experiment. From the missing amplitude and total amplitude, an equilibrium constant for S and S* can be calculated (Keq~1.6).

These values can then be used to correct for the true concentration of S in the initial rate plots (FIG. 9 panel c). Using the linear fit from the initial rate plot, a rate constant was calculated for the conversion of S to S* of 0.091 min$^{-1}$. Fitting the association curves to a first-order rate law resulted in a rate constant of 0.092±0.001 min$^{-1}$ (n=15), which agreed well with the calculated value.

Knowing the Keq and kf (forward rate constant) for the reaction, the reverse rate constant (kr) of 0.056 min$^{-1}$ was calculated.

Resulting kinetics observed in these studies are shown in FIG. 9 panel d. Panel d shows representative dissociation kinetics of the LS complex. LS complex was performed by incubating 1000 nM RPtag large with the indicated concentrations of rhodamine labeled RPtag small. At the start of the experiment, 0.1 mM unlabeled native RPtag small was added and fluorescence anisotropy monitored. Data processing was done as in panel a, except the red fits were to the single exponential decay equation $y=y0+A*exp(-b*t)$. As expected, the initial dissociation rates were linear with respect to the LS complex.

Fitting to a line yields a rate constant (koff)=0.0091 min$^{-1}$ (FIG. 9 panel e). In good agreement, when the kinetics are fit with a first order rate law, a rate constant of 0.012±0.002 min$^{-1}$ (n=15) was observed. Knowing the koff and Kd, the association rate of the S* to LS binding interaction can be calculated to be about 4.6×10^7 M-1 min$^{-1}$. Panel e is a graph of the initial rates of the traces represented in d. Slope of the fit line is 0.0091 min$^{-1}$. Data are mean±SE (n=3).

These rate constants were used to simulate the mechanism shown in FIG. 9 panel f. When the first 1 min of the kinetics were eliminated, to account for the 1 min of dead time the experimental set up, near perfect agreement between the simulation results and the observed data, and the theoretical fits. Again, without wishing to be limited, this agreement indicated that the model accurately represents the mechanism of RPtag (large) and (small) binding. Panel f is a schematic representation of one embodiment of a proposed mechanism for RPtag binding. S is RPtag (small) in a non-binding conformation, S* is RPtag (small) in the binding conformation, L is free RPtag large, LS is the complex of RPtag large and small.

Example 10—Mutagenesis Studies on RPtag(Small)

Mutagenesis studies were carried out on the native RPtag (small) peptide sequence to attempt to identify the region required for binding to RPtag(large), and to identify specific mutations responsible for improving binding affinity or improving binding kinetics. Additionally, these studies might identify a minimal binding domain in RPtag(small) leading to a decrease in the size/number of amino acids in the RPtag(small) peptide.

Effect on Binding Equilibrium

First alanine scanning mutagenesis was performed along the sequence of RPtag(small). Specifically, each amino acid position in RPtag(small) was changed to alanine and the Kd of the resulting peptide measured. The Kds of these alanine mutants is shown in Table 2. These studies identified a cluster of amino acids from about F7 to about K17 that, when changed to alanine, significantly impaired binding affinity. This indicated that the RPtag(large) binding region lies within these about 11 amino acids. Structurally, this region corresponds roughly to the β-sheets on the crystal structure of the tteRBP (PDB 2IOY). Interestingly, despite being in the middle of the β-sheet region, P9 did not impair affinity when changed to alanine. Surprisingly, 3 mutations significantly increased binding affinity to RPtag(large)—E2A, E18A, and Q21A. These positions all lie outside of the putative binding region, and should therefore be amenable to incorporation into the sequences without disrupting the necessary interactions for binding.

TABLE 2

This table provides thermodynamic and kinetic constants measured for RPtag small sequences. All data are mean ± SE, (n = 3-15). All constants are for the transitions diagrammed in FIG. 9e. ND indicates that the parameter could not be determined. All measurements were made by fluorescence anisotropy using N-terminal rhodamine tagged peptides with unlabeled RPtag (large) as above in 50 mM Tris pH 8.0, 0.005% Tween 20.

| Peptide | $K_d$ (nM) | $k_{on}$ (M$^{-1}$ min$^{-1}$) (×10$^7$) | $k_{off}$ (min$^{-1}$) | $K_{eq}$ (S-S*) | $k_f$ (min$^{-1}$) | $k_r$ (min$^{-1}$) |
|---|---|---|---|---|---|---|
| native | 0.21 ± 0.03 | 4.3 ± 0.1 | 0.0091 ± 0.002 | 1.6 ± 0.1 | 0.092 ± 0.001 | 0.056 ± 0.001 |
| g1a | 0.29 ± 0.03 | 1.6 ± 0.1 | 0.0047 ± 0.0003 | 2.3 ± 0.1 | 0.086 ± 0.004 | 0.037 ± 0.001 |
| e2a | 0.10 ± 0.02 | 5.1 ± 0.7 | 0.0053 ± 0.0007 | 1.9 ± 0.1 | 0.084 ± 0.009 | 0.044 ± 0.004 |
| k3a | 0.49 ± 0.02 | 1.1 ± 0.1 | 0.0053 ± 0.0007 | ND | ND | ND |
| i4a | 0.26 ± 0.01 | 2.4 ± 0.1 | 0.0060 ± 0.0002 | 0.9 ± 0.1 | 0.086 ± 0.004 | 0.098 ± 0.016 |
| p5a | 0.23 ± 0.02 | 11 ± 1 | 0.024 ± 0.002 | 1.8 ± 0.2 | 0.093 ± 0.003 | 0.052 ± 0.001 |
| n6a | 0.34 ± 0.04 | 0.45 ± 0.09 | 0.0015 ± 0.0003 | 1.3 ± 0.2 | 0.082 ± 0.003 | 0.068 ± 0.010 |
| f7a | 2.0 ± 0.2 | 3.1 ± 0.1 | 0.063 ± 0.003 | 2.2 ± 0.1 | 0.080 ± 0.001 | 0.036 ± 0.002 |
| i8a | 1.1 ± 0.1 | 8.6 ± 0.9 | 0.090 ± 0.009 | 0.8 ± 0.2 | 0.078 ± 0.001 | 0.046 ± 0.012 |
| p9a | 0.18 ± 0.01 | 1.4 ± 0.2 | 0.0024 ± 0.0004 | 2.7 ± 0.5 | 0.092 ± 0.011 | 0.040 ± 0.010 |
| e11a | 0.80 ± 0.07 | 0.46 ± 0.06 | 0.0067 ± 0.0005 | 1.9 ± 0.1 | 0.080 ± 0.004 | 0.042 ± 0.004 |
| l12a | 4.7 ± 0.2 | 4.3 ± 1.2 | 0.20 ± 0.06 | 1.1 ± 0.1 | 0.089 ± 0.004 | 0.081 ± 0.006 |
| k13a | 1.1 ± 0.1 | 1.7 ± 0.1 | 0.018 ± 0.001 | ND | ND | ND |
| l14a | 8.9 ± 0.5 | ND | >2 | 1.8 ± 0.1 | 0.075 ± 0.005 | 0.044 ± 0.005 |
| i15a | 4.5 ± 0.4 | 25 ± 6 | 1.1 ± 0.3 | 1.4 ± 0.1 | 0.077 ± 0.006 | 0.053 ± 0.002 |
| t16a | 1.2 ± 0.1 | 7.5 ± 0.3 | 0.089 ± 0.003 | 2.5 ± 0.8 | 0.071 ± 0.006 | 0.038 ± 0.011 |
| k17a | 0.54 ± 0.03 | 1.0 ± 0.1 | 0.0057 ± 0.0002 | ND | ND | ND |
| e18a | 0.056 ± 0.013 | 16 ± 0.8 | 0.0087 ± 0.0004 | 1.1 ± 0.1 | 0.054 ± 0.005 | 0.048 ± 0.006 |
| n19a | 0.26 ± 0.02 | 14 ± 1 | 0.037 ± 0.003 | 1.6 ± 0.1 | 0.089 ± 0.003 | 0.057 ± 0.008 |
| v20a | 0.18 ± 0.03 | 6.8 ± 0.5 | 0.012 ± 0.001 | 1.5 ± 0.1 | 0.073 ± 0.003 | 0.050 ± 0.002 |
| q21a | 0.10 ± 0.01 | 3.5 ± 0.4 | 0.0034 ± 0.0003 | 0.8 ± 0.1 | 0.087 ± 0.005 | 0.11 ± 0.01 |
| Nd1 | 0.25 ± 0.03 | 3.4 ± 0.3 | 0.0088 ± 0.0001 | 2.7 ± 0.2 | 0.064 ± 0.008 | 0.024 ± 0.004 |
| Nd2 | 0.067 ± 0.017 | 5.3 ± 1.3 | 0.0035 ± 0.0008 | 0.7 ± 0.1 | 0.063 ± 0.003 | 0.086 ± 0.002 |
| Nd3 | 0.14 ± 0.01 | 8.8 ± 0.3 | 0.012 ± 0.001 | ND | ND | ND |
| Nd4 | 0.30 ± 0.02 | 9.4 ± 0.4 | 0.028 ± 0.001 | ND | ND | ND |
| Nd5 | 0.59 ± 0.08 | 9.6 ± 0.1 | 0.056 ± 0.001 | ND | ND | ND |
| Nd6 | 0.54 ± 0.05 | 12 ± 1 | 0.065 ± 0.003 | ND | ND | ND |
| Nd7 | 2.4 ± 0.1 | 1.8 ± 0.4 | 0.042 ± 0.010 | ND | ND | ND |
| Nd8 | 0.59 ± 0.04 | 9.3 ± 0.3 | 0.055 ± 0.002 | ND | ND | ND |
| Nd9 | 4.9 ± 0.4 | 8.2 ± 0.9 | 0.40 ± 0.04 | ND | ND | ND |
| Nd10 | 5.9 ± 0.2 | 4.3 ± 0.7 | 0.25 ± 0.04 | ND | ND | ND |
| Nd11 | 16 ± 1 | 7.1 ± 3.8 | 1.2 ± 0.6 | ND | ND | ND |
| Nd12 | 520 ± 49 | ND | >2 | ND | ND | ND |
| Nd13 | 84,000 ± 9,600 | ND | >2 | ND | ND | ND |
| Nd14 | >100,000 | ND | ND | ND | ND | ND |
| Nd15 | >100,000 | ND | ND | ND | ND | ND |
| Nd16 | >100,000 | ND | ND | ND | ND | ND |
| Nd17 | >100,000 | ND | ND | ND | ND | ND |
| Cd1 | 0.55 ± 0.04 | 1.1 ± 0.1 | 0.0061 ± 0.0006 | 2.5 ± 0.3 | 0.10 ± 0.01 | 0.042 ± 0.007 |
| Cd2 | 1.1 ± 0.1 | 9.8 ± 0.3 | 0.11 ± 0.01 | 3.5 ± 0.3 | 0.15 ± 0.02 | 0.043 ± 0.005 |
| Cd3 | 1.2 ± 0.1 | 11 ± 2 | 0.12 ± 0.02 | 3.1 ± 0.3 | 0.014 ± 0.01 | 0.045 ± 0.007 |

TABLE 2-continued

This table provides thermodynamic and kinetic constants measured for RPtag small sequences. All data are mean ± SE, (n = 3-15). All constants are for the transitions diagrammed in FIG. 9e. ND indicates that the parameter could not be determined. All measurements were made by fluorescence anisotropy using N-terminal rhodamine tagged peptides with unlabeled RPtag (large) as above in 50 mM Tris pH 8.0, 0.005% Tween 20.

| Peptide | $K_d$ (nM) | $k_{on}$ ($M^{-1}$ $min^{-1}$) ($\times 10^7$) | $k_{off}$ ($min^{-1}$) | $K_{eq}$ (S-S*) | $k_f$ ($min^{-1}$) | $k_r$ ($min^{-1}$) |
|---|---|---|---|---|---|---|
| Cd4 | 1.0 ± 0.1 | 22 ± 2 | 0.22 ± 0.02 | 1.3 ± 0.1 | 0.014 ± 0.01 | 0.11 ± 0.01 |
| Cd5 | 3.6 ± 0.2 | 11 ± 7 | 0.39 ± 0.23 | ND | ND | ND |
| Cd6 | 200 ± 11 | ND | >2 | ND | ND | ND |
| Cd7 | 30,000 ± 2,700 | ND | >2 | ND | ND | ND |
| Cd8 | >100,000 | ND | ND | ND | ND | ND |
| Cd9 | >100,000 | ND | ND | ND | ND | ND |
| Cd10 | >100,000 | ND | ND | ND | ND | ND |
| Cd11 | >100,000 | ND | ND | ND | ND | ND |
| Cd12 | >100,000 | ND | ND | ND | ND | ND |
| Cd13 | >100,000 | ND | ND | ND | ND | ND |
| Cd14 | >100,000 | ND | ND | ND | ND | ND |
| Cd15 | >100,000 | ND | ND | ND | ND | ND |
| Cd16 | >100,000 | ND | ND | ND | ND | ND |
| Nd10, Cd3 | 57 ± 2 | ND | >2 | ND | 0.32 ± 0.13 | 0.050 ± 0.012 |
| Nd10, Cd3, e18a | 71 ± 1 | ND | >2 | ND | ND | ND |
| Nd10, Cd5 | 250 ± 10 | ND | >2 | ND | ND | ND |
| Nd8, Cd3 | 11 ± 1 | ND | >2 | 6.5 ± 0.5 | 0.095 ± 0.013 | 0.015 ± 0.003 |
| Nd8, Cd3, e18a | 13 ± 1 | ND | >2 | ND | ND | ND |
| Nd8, Cd4 | 14 ± 1 | ND | >2 | ND | ND | ND |
| Nd6, Cd3 | 7.3 ± 0.3 | ND | >2 | ND | ND | ND |
| Nd6, Cd3, e18a | 8.2 ± 0.3 | ND | >2 | ND | ND | ND |
| Nd6, Cd4 | 9.9 ± 1.1 | ND | >2 | ND | ND | ND |
| Nd3, p5a, e18a | 0.63 ± 0.03 | 9.2 ± 0.4 | 0.058 ± 0.002 | ND | ND | ND |
| Nd2, Cd3 | 0.56 ± 0.04 | 8.2 ± 0.3 | 0.046 ± 0.002 | 0.6 ± 0.1 | 0.081 ± 0.001 | 0.14 ± 0.01 |
| Nd2, Cd3, e18a | 0.13 ± 0.02 | 40 ± 2 | 0.053 ± 0.002 | 0.3 ± 0.1 | 0.084 ± 0.006 | 0.26 ± 0.04 |
| Nd2, Cd4 | 0.41 ± 0.01 | 20 ± 2 | 0.079 ± 0.006 | 0.7 ± 0.1 | 0.093 ± 0.001 | 0.13 ± 0.01 |
| Nd2, Cd3, p5a | 0.64 ± 0.07 | 26 ± 1 | 0.16 ± 0.01 | 0.6 ± 0.1 | 0.093 ± 0.007 | 0.16 ± 0.03 |
| Nd2, Cd3, p5a, e18a | 0.56 ± 0.05 | 33 ± 2 | 0.18 ± 0.01 | 0.7 ± 0.1 | 0.086 ± 0.002 | 0.13 ± 0.01 |
| Nd2, Cd4, p5a | 0.82 ± 0.02 | 22 ± 1 | 0.18 ± 0.01 | 0.8 ± 0.1 | 0.11 ± 0.01 | 0.14 ± 0.01 |
| Nd2, e18a | 0.13 ± 0.03 | 6.5 ± 0.7 | 0.0083 ± 0.0010 | 0.4 ± 0.1 | 0.044 ± 0.001 | 0.13 ± 0.02 |
| Nd2, p5a, e18a | 0.047 ± 0.018 | 28 ± 2 | 0.013 ± 0.001 | 0.3 ± 0.1 | 0.051 ± 0.001 | 0.19 ± 0.02 |
| Nd2, k3r, p5a, e18a | 0.26 ± 0.02 | 3.4 ± 0.1 | 0.013 ± 0.001 | ND | ND | ND |
| Nd2, k3a, e18a | 0.88 ± 0.01 | 2.6 ± 0.1 | 0.032 ± 0.001 | ND | ND | ND |
| Nd2, k3a, p5a | 0.55 ± 0.01 | 2.4 ± 0.1 | 0.0090 ± 0.0004 | ND | ND | ND |
| Nd2, e18a, v20a, q21a | 0.36 ± 0.02 | 3.6 ± 0.3 | 0.023 ± 0.001 | 0.8 ± 0.1 | 0.045 ± 0.002 | 0.060 ± 0.005 |
| Nd2, p5a, e18a, v20a, q21a | 0.16 ± 0.03 | 20 ± 1 | 0.013 ± 0.001 | 0.4 ± 0.1 | 0.050 ± 0.003 | 0.14 ± 0.03 |

Next, sequential truncation mutagenesis from both the N- and C-termini of the peptide was performed (see Table 2). Beginning at about position Nd7 (deletion of 7 amino acids from N-terminus) impairments of ~10 fold or greater were identified. This level of Kd reduction was also seen with Cd5 mutations (removal of 5 amino acids from C-terminus). These truncations, respectively, correspond to the F7 and K17 identified above in the alanine scanning studies.

A second region of the irregular β-sheets was found between about L12 and K17. This region appears to also be involved in binding the RPtag(large) protein, like the first identified region between about F7 and E11. In this second region, $K_d$ impairments of >1000-fold resulted from truncating into the region from either the N or C terminus. Surprisingly, Nd8 (removing the first 8 amino acid positions while leaving P9 as the N-terminal amino acid) resulted in improving the binding affinity for RPtag(large), relative to the truncations to positions 7 or 9. This data aligns well with the observation that mutation P9A did not significantly impair the binding affinity, but A mutations at positions 8 and 11 did.

Effect of Binding Rates

The library of mutant RPtag(small) peptides, described above, was next analyzed to measure off rates (koff). The on rate was also calculated from measured koff and Kd (S*-LS transition), except instead of using unlabeled native peptide as the competitor, we used unlabeled Nd2,P5A,E18A (the tightest binding RPtag(small) peptide identified). These studies showed that kon and koff roughly tracked with Kd. However, there were notable exceptions. For example, although mutation P5A (proline at position 5 of RPtag (small) changed to alanine) did not have a significant effect on Kd, the mutation increased the kon and koff by a factor of ~7. This indicates, without wishing to be limited, that P5 may constrain the structure of the peptide. The increased flexibility imparted to the peptide by the P5A mutation may decrease the energy barrier required for binding/unbinding. N6A had the opposite effect, decreasing the on and off rates without having a significant effect on Kd, indicating that this mutation may increases the energy barrier.

Forward and reverse rate constants for the S-S* transition revealed additional notable mutants. Measured Keq's and kf's as well as the calculated kr's for the alanine scanning and truncation library peptides were all similar, with the exception of K3A, K13A, K17A, Nd3 truncations and further, and Cd5 truncations and further. A Keq or kf (and correspondingly kr) could not be determined for these mutants as the association reaction appeared to be completed within the dead time of the instrument (~1 min). Of note, the Nd3 deletion corresponds to deletion through K3, and Cd5 corresponds to deletion through K17. This indicated that lysines in the peptide may play a significant role in limiting the rate of LS complex formation. Moreover, again without wishing to be limited, the rate limiting structure/interaction may be alleviated by the mutation or removal of either lysine.

The kinetics data described above has at least two possible interpretations. Either these mutations cause a substantial increase in the rate of the S-S* transition, or they shift the Keq of S-S* such that it heavily favors S* (or some combination of the two). Without wishing to be limited, the end result may be a substantial increase in the rate of formation of the LS complex. Of the 3 lysines, only K3 falls outside the proposed RPtag(large)-binding region, which may allow the making mutations at or truncations of K3 much more readily than at either K12 or K17.

Mutant RPtag(Small) Peptides with One or More Alanine Substitutions and/or Truncations Several of the mutations identified above, in the alanine scanning mutagenesis and truncation mutagenesis, were combined and analyzed. These experiments were intended to potentially identify two peptides: the smallest peptide with antibody-like binding affinity to RPtag (large) (Kd≤$10^{-8}$ M) and fastest kinetics, and the peptide with the tightest binding regardless of size or kinetics.

These studies identified the Nd8 truncation with the Cd4 truncation (Nd8Cd4) as having favorable characteristics in terms of size, kinetics, and Kd. This peptide has a size of 9 amino acids, a Kd of ~14 nM, and binding/unbinding kinetics completed within the dead time (see Table 1; apparently meeting the criteria of the first desired peptide). Next, Nd2, p5a, and e18a were combined and analyzed. This peptide possessed a Kd of ~47 pM, which appeared to meet the criteria for the second desired peptides.

These two identified RPtag(small) mutant peptide sequences were subjected to additional testing, described below. Their sequences are:

```
PAELKLITK          -- "RPtag(small) (fast)" or
                      "Nd8Cd4)"

KIANFIPAELKLITKANVQ -- "RPtag(small) (tight)" or
                      "Nd2p5ae18a"
```

Example 11—Analysis of pH Profile

Figure 10:
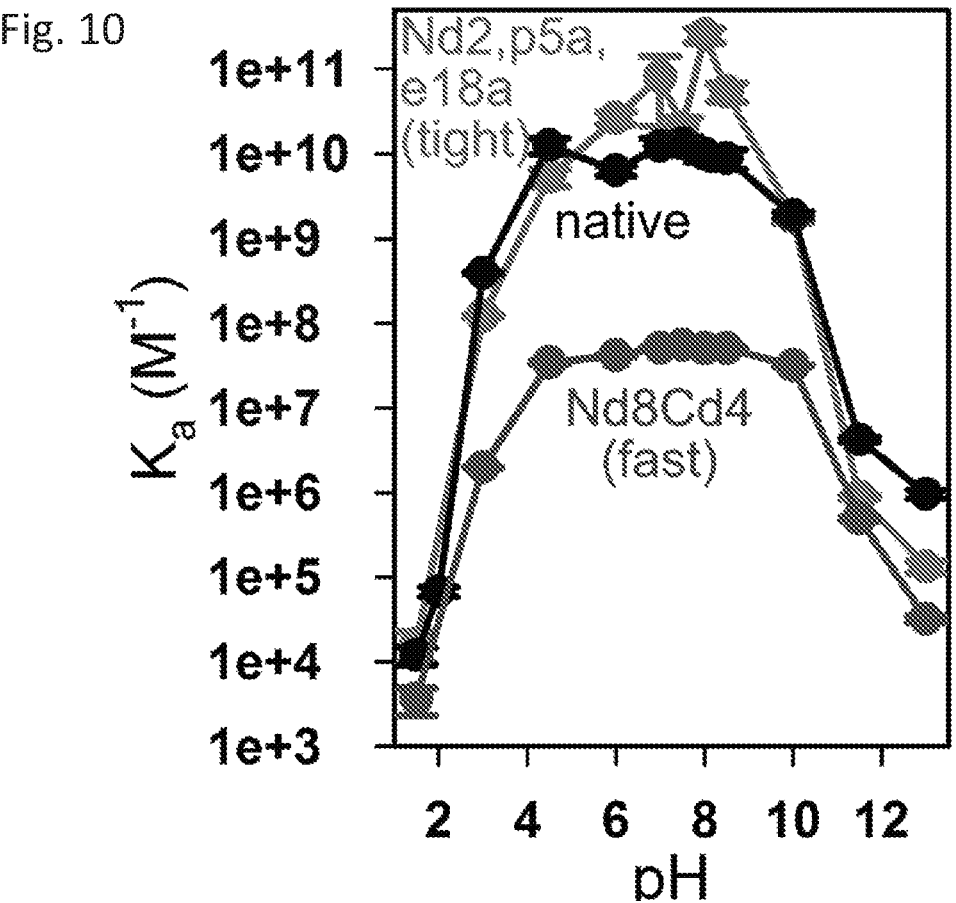
FIG. 10 shows pH profiles of representative sequences.

The Kds of Nd8,Cd4 for RPtag(large) was measured in the presence of buffers of different pHs ranging from 1.5 to 13. These studies found that native, Nd8Cd4, and Nd2p5ae18a all showed good stability over a wide pH range, and possessing a maximum affinity between pH 4-10, with a relative maximum at ~pH 8 (FIG. 10).

For these experiments, $K_d$s were measured by fluorescence anisotropy as described above in the following buffers, all at 100 mM with 0.005% Tween 20: glycine pH 1.5, glycine pH 2.0, glycine pH 3.0, acetate pH 4.5, 2-(N-morpholino)ethanesulfonic acid pH 6.0, tris pH 7.0, tris pH 7.5, tris pH 8.0, tris pH 8.5, borate pH 10.0, phosphate pH 11.5, phosphate pH 13.0.

Reagent Screening

To determine reagent compatibility with the disclosed system, an additive screen was performed, wherein the Kd between RPtag (large) and 3 RPtag (small) peptides—native, Nd8Cd4, and Nd2p5ae18a—were tested in the presence of several common buffer additives (Table 3).

TABLE 3

Buffer additive screen. Kd's were measured as above in 100 mM Tris pH 8.0, 0.005% Tween 20, and the indicated buffer additives. Shown are Kd's in nM.

| Buffer Additive | native | Nd8Cd4 | Nd2, p5a, e18a |
| --- | --- | --- | --- |
| No Additive | 0.21 | 14 | 0.037 |
| DMSO (20%) | 0.17 | 140 | 0.023 |
| EtOH (20%) | 0.17 | 733 | 0.10 |
| MeOH (20%) | 0.11 | 34 | 0.056 |
| acetone (20%) | 0.15 | 22 | .019 |
| glycerol (20%) | 0.034 | 27 | <0.001 |
| BME (10%) | 5.3 | 740 | 6.7 |
| DTT (100 mM) | 0.51 | 33 | 0.073 |
| PG (50%) | 19 | 4600 | 49 |
| imidazole (3M) | >10000 | >10000 | >10000 |
| ribose (3M) | 0.023 | 42 | <0.001 |
| sorbitol (3M) | 2.5 | 16 | <0.001 |
| NaCl (3M) | 0.0027 | 0.15 | <0.001 |
| KCl (3M) | <0.001 | 0.066 | 0.011 |
| $NH_4SO_4$ (3M) | 1.5 | 2.8 | 44 |
| $MgCl_2$ (3M) | 124 | 240 | 350 |
| $CaCl_2$ (3M) | 330 | >10000 | 150 |
| $NiCl_2$ (100 mM) | 3.2 | 42 | 2.2 |
| $MnSO_4$ (10 mM) | 160 | 160 | 22 |
| Gdn-HCl (6M) | >10000 | >10000 | >10000 |
| urea (8M) | >10000 | >10000 | >10000 |
| Tween20 (2%) | 0.49 | 45 | 4.7 |
| TritonX-100 (2%) | 0.64 | 180 | 0.046 |
| SDS (2%) | >10000 | >10000 | >10000 |

These experiments demonstrated that the disclosed proteins, peptides, and systems were robust in the presence of a number of organic compounds (DMSO, methanol, ethanol, glycerol, and acetone), reducing agents (DTT), and detergents (Tween20 and TritonX-100). Interestingly, kosmotropic salts such as NaCl and KCl significantly stabilized the interaction between RPtag(large) and RPtag(small). In particular, the RPtag(small) mutant peptide Nd8Cd4 showed an increased affinity of about >100-fold. In contrast, addition of chaotropic salts, such as $MgCl_2$ and $CaCl_2$, resulted in a destabilized LS complex. Surprisingly, addition of imidazole significantly destabilized the interaction of RPtag(small) and RPtag(large). Under the conditions of this experiment all apparent binding affinity between the two RPtags was removed.

Next the affinity of RPtag(small) mutant peptide Nd8Cd4 was analyzed as a function of NaCl and imidazole. These studies identified a dose-dependent enhancement of affinity in the presence of NaCl, and impairment of affinity with imidazole (not shown).

Example 12—Native Elution Condition

Because of the observed stabilizing character of NaCl and destabilizing character of imidazole on Nd8Cd4 binding, these reagents, among others, were incorporated into a novel buffering system for use with the disclosed proteins, peptides, systems, and methods. In particular, the effect of this novel buffer on binding of RPtag (small) Nd8Cd4 to an immobilized RPtag(large) column was studied. These experiments included eluting both (1) rhodamine labeled peptide and (2) N-terminally RPtag(small) Nd8Cd4 tagged with tagRFP from a column under native conditions. Generally, native conditions is taken to mean at or near biological conditions under which many proteins are folded, e.g. pH 4-9 at moderate temperature (4° C.-30° C.) in the absence of denaturants (e.g. guanidine hydrochloride, urea, SDS). This is in contrast to denaturing conditions, which generally rely on extreme pH (e.g. ≤2) denaturants, or high temperature to unfold proteins.

Briefly, columns, as described above, were first equilibrated with 10 mL 100 mM Tris pH 8.0, 3 M NaCl, 0.005% Tween20. Next, 1 mL of 10 uM rhodamine-tagged Nd8Cd4 or tagRFP containing an N-terminal RPtag (small) Nd8Cd4 tag was applied in the same buffer. The column was then washed with 10 mL of the same buffer. Finally, bound target molecules were eluted with 10 mL of 100 mM Tris pH 8.0, 3 M imidazole, 0.005% Tween20.

These experiments demonstrated that both the protein and the peptide could be eluted as a tight band. This demonstrated the efficacy of the disclosed buffering system for use in binding and elution of peptides and proteins at neutral pH. These same conditions caused native and Nd2p5ae18a peptides to bind in a tight band. Although these peptides were able to be eluted, instead of eluting as a tight band, the eluted band spread through the resin, creating a diffuse band. This suggested that modification of the disclosed buffering system for these sequences may be beneficial.

Example 13—Affinity-Based Precipitation/Pull-Down

The disclosed proteins and peptides were used in precipitation/pull-down assays. Specifically, rhodamine was tagged with the RPtag(small) Nd8Cd4 peptide and RPtag(large) was immobilized on a resin, as described above.

Briefly, 100 μL 1000 nM rhodamine labeled RPtag(small) peptide was incubated with 2.5 uL wet settled RPtag (large) resin generated as (as described above) in phosphate buffered saline (PBS; Gibco)+1% BSA+0.005% Tween 20 at 4° C. for 60 min with continuous orbital shaking. Samples were then washed 3× with 500 μL of the same buffer with no peptide to remove unbound peptide. Bound RPtag(small) peptides were then eluted with 100 μL 100 mM glycine pH 1.5+0.005% Tween20, and the pH raised by adding 1 μL 1 M borate pH 10.0. The amount eluted was calculated from the blank subtracted fluorescence of the elution versus the load. After each elution, resin was washed once with 500 μL 6M GdnHCl and once with 500 μL phosphate buffered saline (Gibco)+1% BSA+0.005% Tween 20, before repeating the assay. Data shown in FIG. 11 are mean±SE (n=3).

Sequential precipitation/pulldown trials were performed with the rhodamine labelled RPtag(small) Nd8Cd4 peptide, and the RPtag(large)-resin. After binding and pull-down, the rhodamine-peptide was eluted in 100 mM glycine pH 1.5, the column was washed with water and 6 M guanidine hydrochloride, and then re-equilibrated with buffer (50 mM Tris pH 8.0, 10 mM EDTA). RPtag(small) Cd12 peptide as used as a negative control due to its similar size (9 amino acids) and markedly lower binding affinity for RPtag(large).

Figure 11:
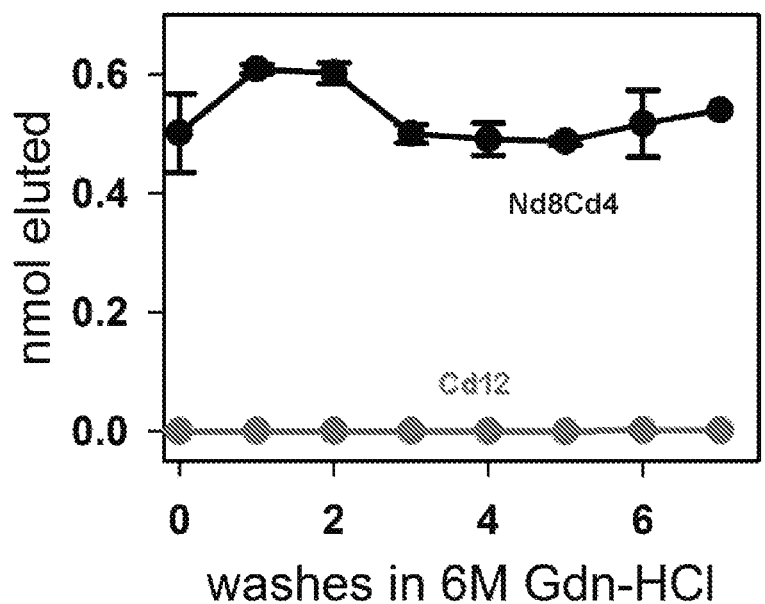
FIG. 11 shows results from sequential pulldown trials.

FIG. 11 shows that the rhodamine labeled RPtag(small) Nd8Cd4 peptide was repeatedly precipitated in these assays with little to no loss of binding capacity. Surprisingly, washing with 6 M guanidine hydrochloride did not appear to affect binding capacity, even after 7 sequential pulldowns, at which point the experiment was stopped (FIG. 11). As expected, no binding of the control peptide could be detected. These experiments show that the disclosed proteins, peptides, systems and methods are very specific. Moreover, binding capacities identified in these experiments were within the range of existing commercial affinity/pulldown kits (e.g. anti-myc agarose resin capacity from ThermoFisher ~102 nmol/mL RPtag resin capacity ~200 nmol/mL)

Example 14—Affinity-Based Detection

The disclosed proteins and peptides were used for detection assays. In these experiments, RPtag (small) was recombinantly fused to an alkaline phosphatase. Specifically, the RPtag(small) peptide Nd8Cd4 was fused to the N-terminus of a highly active monomeric alkaline phosphatase (PhoX class) from *Pasteurella multocida*. RPtag (large) with an engineered cysteine was immobilized to a white, polystyrene 96-well plate via activated maleimide (ThermoFisher) according to the manufacturer's instructions. Control wells were blocked with cysteine. 100 μL of 12.4 μM RPtag (small) Nd8Cd4-labeled alkaline phosphatase was added to both the experimental and control wells and then incubated for 1.5 hrs at room temperature. Wells were washed 3× in 50 mM Tris pH 8.0, 150 mM NaCl, 1% BSA, 0.05% Tween 20, and then either assayed with 0.25 mM CSPD purchased from ThermoFisher (a luminescent alkaline phosphatase activity probe) and measured immediately at room temperature, or 2 mM p-nitrophenyl phosphate (an absorbance alkaline phosphatase reagent) in 50 mM Tris pH 9.5, 150 mM NaCl, 100 μM $CaCl_2$), 0.2% Tween 20) and measured after 60 minutes at room temperature. Measurements were taken on a SpectraMax i3 (Molecular Devices). For luminescence, the plate was placed into the instrument, mixed for 60 seconds in the dark, and then all wavelengths were collected from each well. For absorbance, after 60 minutes the samples were transferred to a transparent 96 well plate and the absorbance measured at 405 nm.

Figure 12:
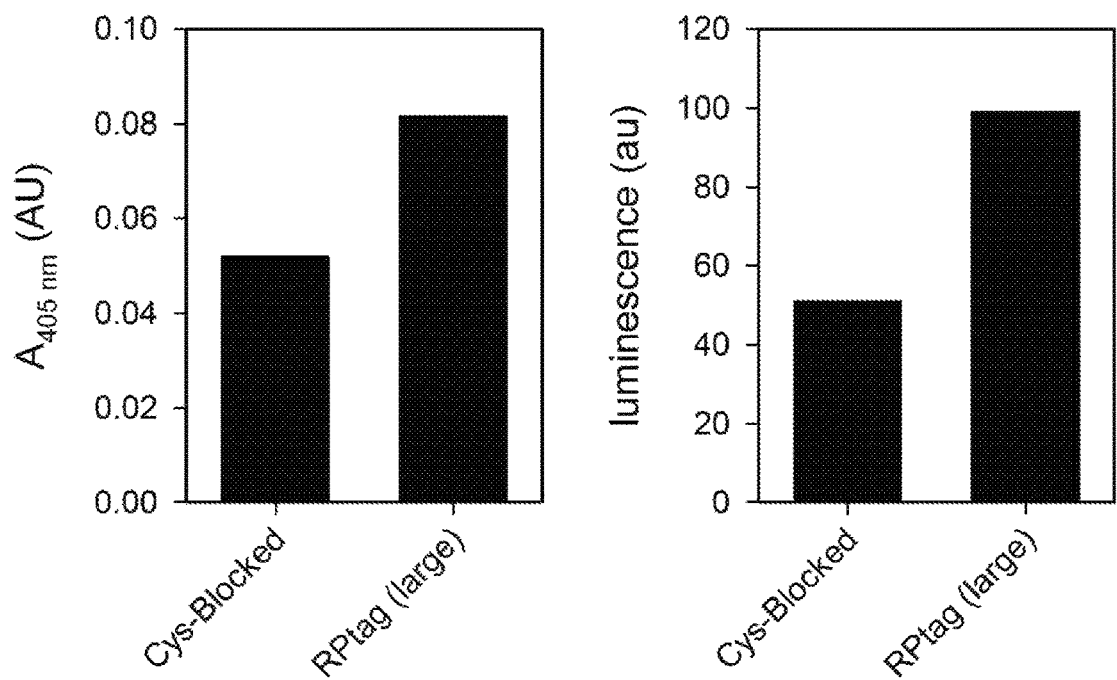
FIG. 12 shows results of ELISA trials, with data for pNPP substrate shown at left, and CSPD at right.

As shown in FIG. 12, both the CSPD and p-nitrophenyl phosphate reagents resulted in a significant difference between experimental wells (containing RPtag(large) immobilized) and the control wells (no RPtag(large)) with their respective signals, indicating that this system is useful for detection, specifically in ELISA (FIG. 12).

Example 15—Mutagenesis Studies to Generalize Binding

Additional mutagenesis studies were carried out on the RPtag(large) and RPtag(small) sequences to further study binding. First, the ability to engineer compensatory mutations in each protein was investigated. Second, native RPtag (large) peptide sequence was modified to study this protein's ability for expanded recognition/specificity.

Compensatory Mutations in RPtag(Large) and RPtag(Small)

Figure 13:
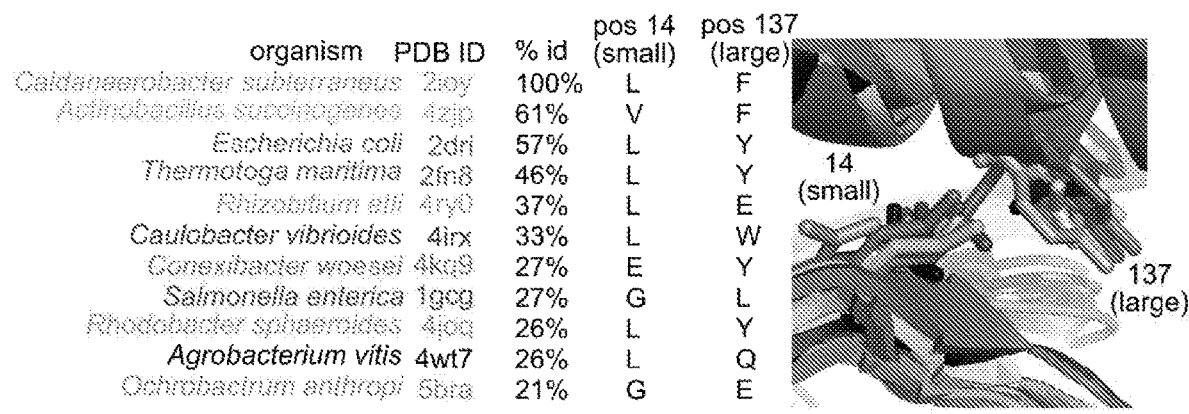
FIG. 13 shows superimposed x-ray crystal structures of periplasmic sugar binding proteins from the protein data bank.

11 PDB crystal structures of periplasmic sugar-binding proteins, from diverse species, were aligned to further investigate residues involved in binding specificity (FIG. 13). Residues indicated in FIG. 13 are those that correspond in in RPtag(small) and RPtag(large) after aligning in 3D space. Specifically, shown are position 14 on RPtag small and 137 on RPtag large. Numbering is according to the full sequence of the native RPtag large construct used in this document including all tags. Alignments and renderings were done with PyMol.

Of the 11 RPtag(small) PDB crystal structures investigated, 8 sequences showed strong conservation of leucine (L) or valine (V) at position 14. 7 of the 11 RPtag(large) PDB crystal structures, possess an aromatic residue at position 137.

Figure 14:
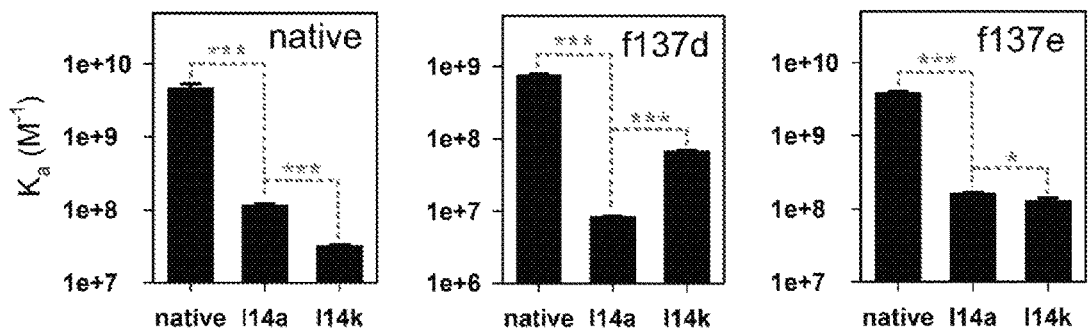
FIG. 14 shows specificity alteration in engineered RPtag (small) construct.
Figure 15:
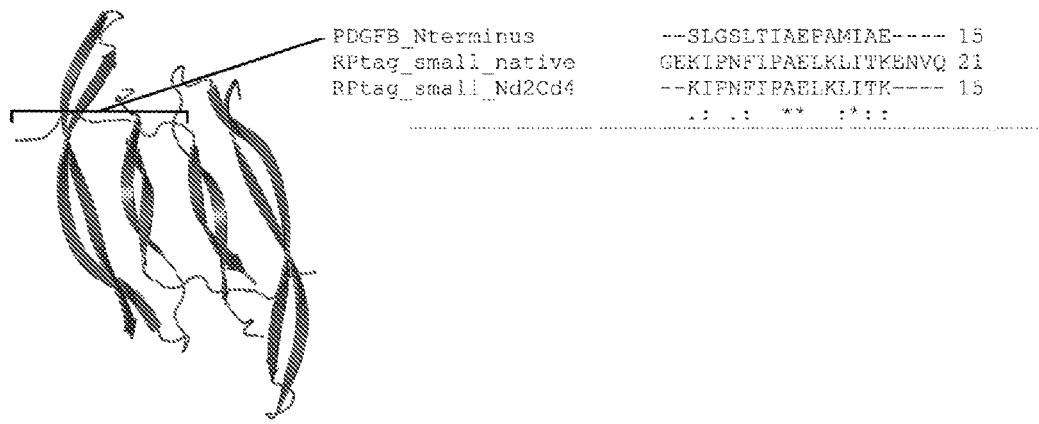
FIG. 15 shows an X-ray crystal structure of mature PDGF-β dimer (left) (SEQ ID NO: 11) and N-terminal sequence alignment with RPtag (small) (right) (SEQ ID NO: 13).

The possibility of creating compensatory mutations in the two sequences was investigated by modifying position 14 of RPtag(small) and position 137 of RPtag(large). First, a positively charged lysine (K) was introduced at position L14 of RPtag(small) (FIG. 14). This substitution significantly impaired binding of the mutant RPtag(small) to native RPtag(large), decreasing its affinity even more than the L14A, mutation (Table 2), which was the most destabilizing mutant identified in the alanine scanning mutagenesis study. Next, position F137 of RPtag(large) was mutated to aspartic acid (D), which is a negatively charged residue under physiologic conditions. This substitution was introduced into RPtag(large) to balance the charge with the L14K substitution, and help restore interaction between the two residues. As shown at FIG. 14, this substitution substantially restored the binding affinity of L14K RPtag(small) for F137D RPtag(large). In other embodiments, different compensatory mutations may be introduced at F137 and L14, as well as other positions in the two RPtag proteins.

These experiments demonstrate that applicants have identified the pocket/cleft in the RPtag (large) protein useful for interacting with the RPtag(small) peptide. Further, as one of skill in the art would understand, additional positions, mutations, and substitutions in the RPtag protein sequences may aid in producing additional binding enhancements.

Modifying Specificity of RPtag(Large) for Non RPtag(Small) Target Proteins (PDGF-β)

PDGF-β was selected as a target protein for these studies because of its clinical importance to diseases such as cancer and macular degeneration. In addition, the physically accessible N-terminus of PDGF-β possesses some homology to RPtag(small) (FIG. 15; showing PDB ID: 1PDG, with N-termini highlighted in magenta; the structure was rendered in PyMol, and alignments shown at right were done in Clustal Omega).

An initial $K_d$ was measured between RPtag(large) and the PDGF-β N-terminal peptide (FIG. 16). These experiments determined a value of 7.3 μM for the initial $K_d$. Next, competition experiments were performed using the mutant RPtag(small) peptide Nd2,P5A,E18A. This study determined that binding of RPtag(large) to the PDGF-β N-terminal peptide could be disrupted by unlabeled Nd2,P5A,E18A (tight) peptide, suggesting a common binding site on RPtag(large) for the two peptides.

Mutation studies were next performed to identify residues in RPtag(large) that could enhance binding to PDGF-β peptide. For these studies, residues within 5 Å of the putative RPtag(small) binding cleft were identified—H122, D126, K129, G130, F137, A253, L233, and M270. Other positions within that area are I108, V120, S121, H122, I123, A124, S125, D126, K129, G130, M133, F137, F237, E241, L244, I247, K248, G250, A253, A254, T255, I256, A257, Q258, Q259, M263, L266, M270, K273, Y274, L275, and K276. Numbering for RPtag(large) for these studies is relative to "NativeRPtag(large)_with_Tags_and_Cys" provided below. This protein includes a 19 aa leader sequence (MGSSCHHHHHHSQDPNSSS). Next, 31 mutants of RPtag(large) were generated at a subset of 32 amino acids (H122, D126, K129, G130, F137, A253, L233, and M270) proximal to non-conserved residues between RPtag(small) and PDGF-β when modeled in the crystal structure. The $K_d$ of each mutant was then measured to identify mutations that improved RPtag(large) affinity for PDGF-β peptide, but not for the a control RPtag(small) peptide (Nd2Cd4) (FIG. 17). Briefly, the data presented in FIG. 17 are aligned such that the wt affinities are in-line with the gray dashed line, so enhanced affinity and specificity is seen when the blue (PDGF-β) bars are above the line and the red bars (Nd2Cd4 control) are below the line.

These studies identified two positions where such mutations (with enhanced binding for PDGF-β peptide, but decreased binding for Nd2Cd4) occurred, H122 and A253. Two substitutions at these positions that provided the best affinity for PDGF-β peptide were H122L and A253R. This double mutant RPtag(large) exhibited a enhanced binding affinity for PDGF-β peptide ($K_d$=1.5 μM versus a $K_d$ of 7.3 μM for binding to native RPtag(large)) and a reduced affinity for RPtag(small) (Nd2Cd4) ($K_d$=3.1 nM versus a $K_d$ of 0.41 nM for binding to native RPtag(large)).

The modeled energy-minimized structure of the RPtag (large) H122L and A253R double mutant suggested a new hydrophobic interaction between PDGF-β peptide L5 and RPtag(large) peptide L122, and a new ion pair between PDGF-β peptide E15 and RPtag(large) peptide R253 (FIG. 18). Briefly, FIG. 18 is a structural rendering using the PDB 2ioy structure as a basis, the aligned corresponding residues in the RPtag small portion of the protein to those of the PDGF-β peptide (top) were mutated and the energy minimized in PyMol. This was repeated with the h122l and a253r mutations (bottom) introduced in the RPtag large portion of the protein. In the double mutant energy minimized structure, a new hydrophobic contact between L122 and L5 was identified along with a new ion pair between R253 and E15 in the double mutant not seen in the single mutant.

This provides a plausible structural explanation for this tighter binding. Notably, the double mutant RPtag(large) bound purified PDGF-β dimer even tighter, with a $K_d$=75 nM. This further-enhanced binding is likely because of the proximity and corresponding high local concentration of two N-termini in the PDGF-β structure (FIG. 19). Briefly, the indicated concentration of recombinant purified, and refolded PDGF-β dimer (see protocol below) was incubated with 100 nM RPtag large labeled with FITC. After 1 h incubation at room temperature, fluorescence anisotropy was measured, and the resultant curves were fit to a standard binding equation.

These studies show that RPtag(large) can be modified to select for binding to proteins other than RPtag(small) and its use as a monobody-type protein. One of skill in the art would understand that additional techniques may provide for further enhancements in both binding specificity and affinity of RPtag (large) for PDGF-β. For example, library based selection techniques such as phage and yeast display may be used to evolve RPtag (large) protein sequences with enhanced affinity for PDGF-β as well as other target proteins. Potential target proteins may include, without limitation, other PDGF isoforms, vascular endothelial growth factor (VEGF), VEGF receptor, erbB-2, HER2/neu, α-tubulin, amyloid-β (1-38, 1-40, 1-42 and other fragments), Estrogen receptors, TNF-α, Lupus anticoagulant antibodies, among others.

Materials and Methods

>NativeRPtag(large)_with_Tags_and_Cys (RPtagLarge sequence proper starts at MKEGKT . . . , all mutant numbering in here is done based off of this sequence including the tags and N-terminal Met.

```
MGSSCHHHHHHSQDPNSSSMKEGKTIGLVISTLNNPFFVTLKNGAEEKA
KELGYKIIVEDSQNDSSKELSNVEDLIQQKVDVLLINPVDSDAVVTAIK
EANSKNIPVITIDRSANGGDVVSHIASDNVKGGEMAAEFIAKALKGKGN
VVELEGIPGASAARDRGKGFDEAIAKYPDIKIVAKQAADFDRSKGLSVM
ENILQAQPKIDAVFAQNDEMALGAIKAIEAANRQGIIVVGFDGTEDALK
AIKEGKMAATIAQQPALMGSLGVEMADKYLK.
```

Regarding the studies shown in FIG. 14, increasing concentrations of unlabeled RPtag large with the indicated mutations (native, f137d, and f137e) were incubated for 1 h with 1 nM rhodamine labeled RPtag small peptide and the fluorescence anisotropy was measured. Resultant curves were fit with the equation f=y0+(ymax−y0)*(Ptot+x+Kd− sqrt((Ptot+x+Kd)^2−4*Ptot*x))/(2*Ptot), where y0 is the baseline anisotropy, ymax is the maximum anisotropy, Ptot is the fixed concentration of labeled peptide used, x is the variable concentration of protein used, and Kd is the measured Kd. Data are presented here as Ka=1/Kd. Log transformed Ka's were then compared by one-way ANOVA with Holm-Sidak post hoc correction. *p<0.001, p<0.01, *p<0.05. data are mean±SEM (n=3-4). Buffer was 50 mM Tris pH 8.0, 0.005% tween20. Proteins were expressed and purified by single step NiNTA chromatography as before. Peptides were synthesized solid-state and handled as previous.

Figure 16:
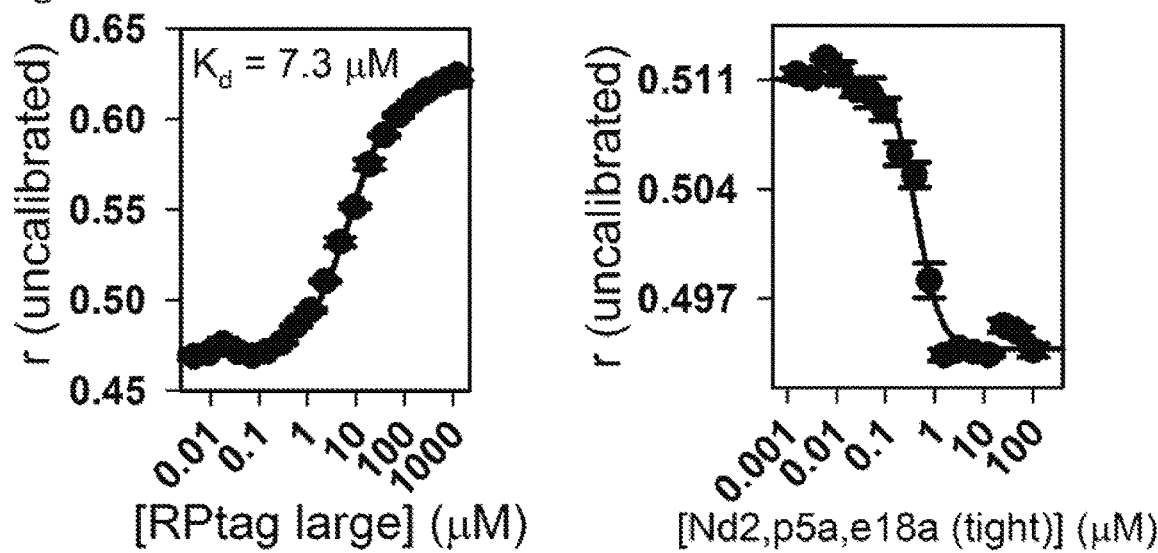
FIG. 16 shows direct binding (left) and competition (right) curves for RPtag (large) and PDGF-β n-terminal peptide.

The direct binding (left) and competition studies (right) presented in FIG. 16 were performed as follows. The indicated concentration of RPtag large was incubated with 20 nM rhodamine labeled PDGF-β n-terminal peptide for 1 h at room temperature, and the fluorescence anisotropy was measured. The curves were fit with the equation f=y0+(ymax−y0)*(Ptot+x+Kd−sqrt((Ptot+x+Kd)^2−4*Ptot*x))/(2*Ptot), where y0 is the baseline anisotropy, ymax is the maximum anisotropy, Ptot is the fixed concentration of labeled peptide used, x is the variable concentration of protein used, and Kd is the measured Kd. For competition binding, 1 uM RPtag large and 1 uM rhodamine labeled PDGF-β n-terminal peptide were mixed with the indicated concentration of unlabeled competitor peptide, Nd2,p5a, e18a, (this engineered peptide demonstrated the tightest binding identified thus far) for 1 h at room temperature and the fluorescence anisotropy was measured. The curves were fit empirically to a 4 parameter logistic regression. In both cases, the buffer was 50 mM Tris pH 8.0, 0.005% Tween20. Curves were fit in 4 independent trials each, and the data was averaged for display. Points are mean±SEM (n=3).

Figure 17:
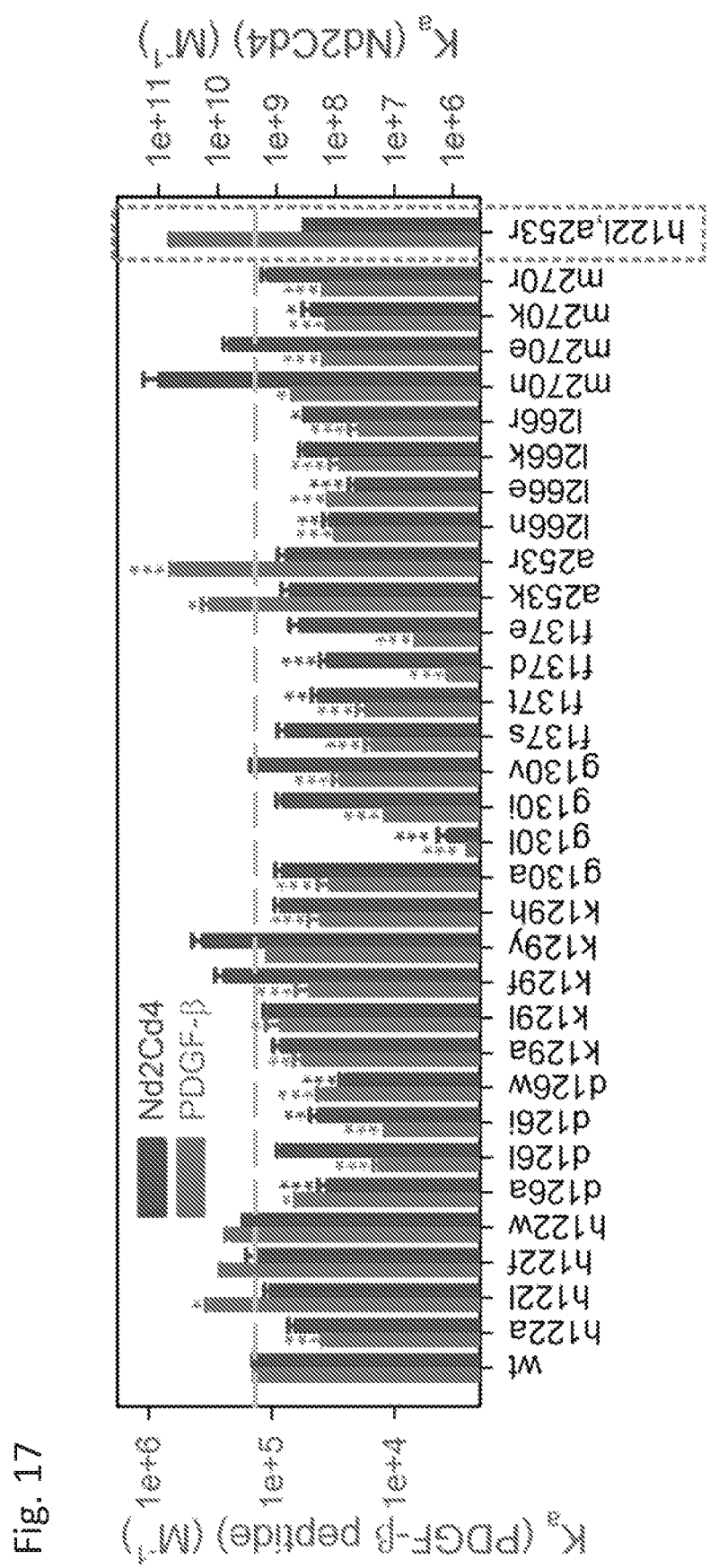
FIG. 17 shows a mutational screen for enhancing specific binding to PDGF-β n-terminal peptide.

As shown in FIG. 17, the indicated mutations were made to RPtag large, and the resultant proteins expressed and purified by single-step NiNTA chromatography as before. Kds were measured by incubating increasing concentrations of unlabeled RPtag large mutant with either 20 nM rhodamine labeled PDGF-β n-terminal peptide or 2 nM rhodamine labeled Nd2Cd4 variant of RPtag small, as it has the same number of amino acids as the PDGF-β peptide but contains the native binding sequence. After the incubation, fluorescence anisotropy was measured, and the resultant curves were fit with the equation f=y0+(ymax−y0)*(Ptot+x+Kd−sqrt((Ptot+x+Kd)^2−4*Ptot*x))/(2*Ptot), where y0 is the baseline anisotropy, ymax is the maximum anisotropy, Ptot is the fixed concentration of labeled peptide used, x is the variable concentration of protein used, and $K_d$ is the measured Kd. Data are presented here as Ka=1/Kd. Log transformed Ka's were then compared by one-way ANOVA relative to wt control with Holm-Sidak post hoc correction. *p<0.001, p<0.01, *p<0.05. data are mean±SEM (n=3-4). Buffer was 50 mM Tris pH 8.0, 0.005% Tween20. For the sake of comparison, the double mutant h122l,a253a is shown on the same axes, but was not included in the statistical analysis as the experiment was done after the initial results identified the two single mutants.

Figure 18:
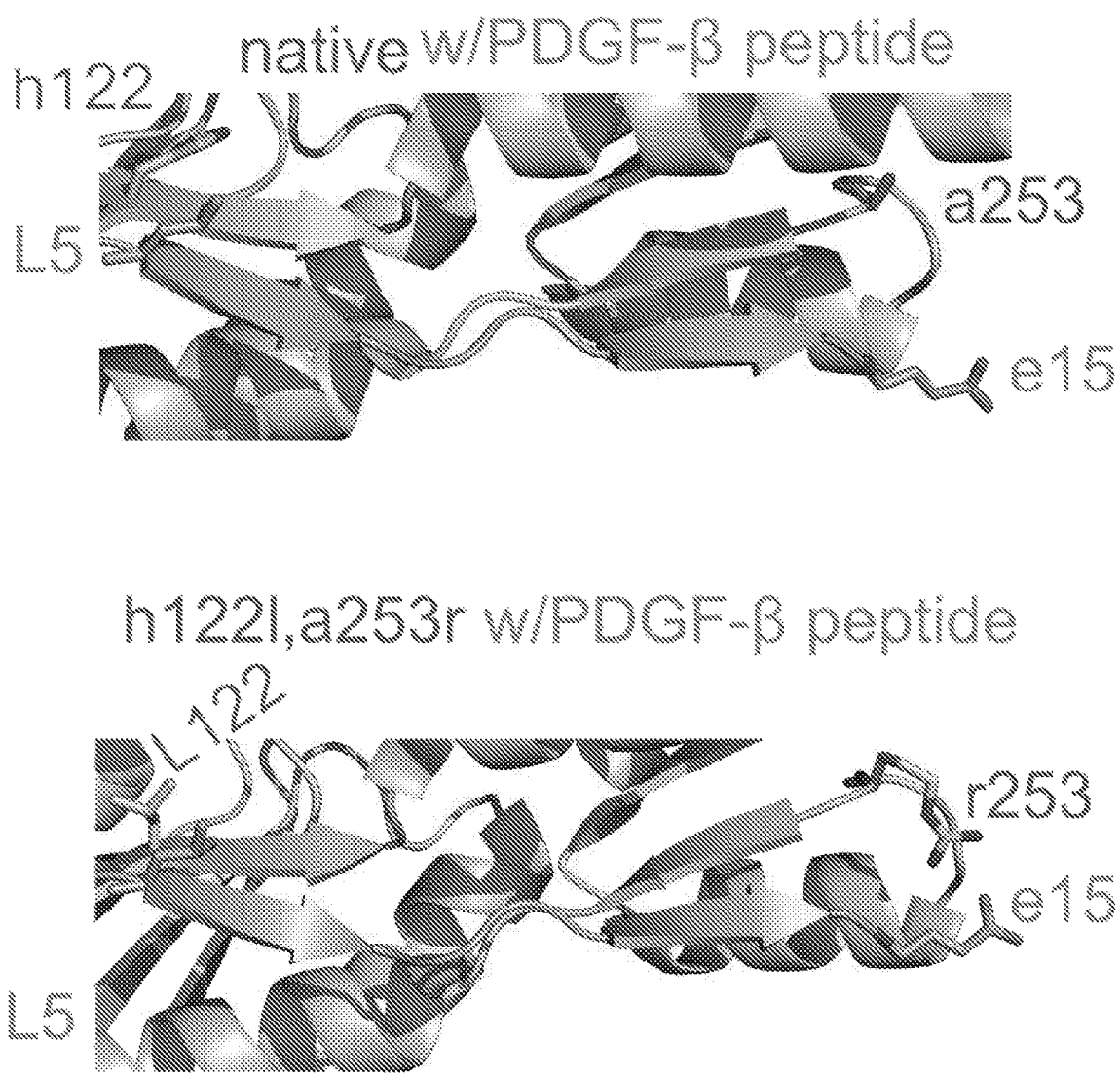
FIG. 18 shows energy minimized modeled crystal structures of native RPtag (large) and RPtag (large) h122l,a253r (blue) with PDGF-β peptide (orange).
Figure 19:
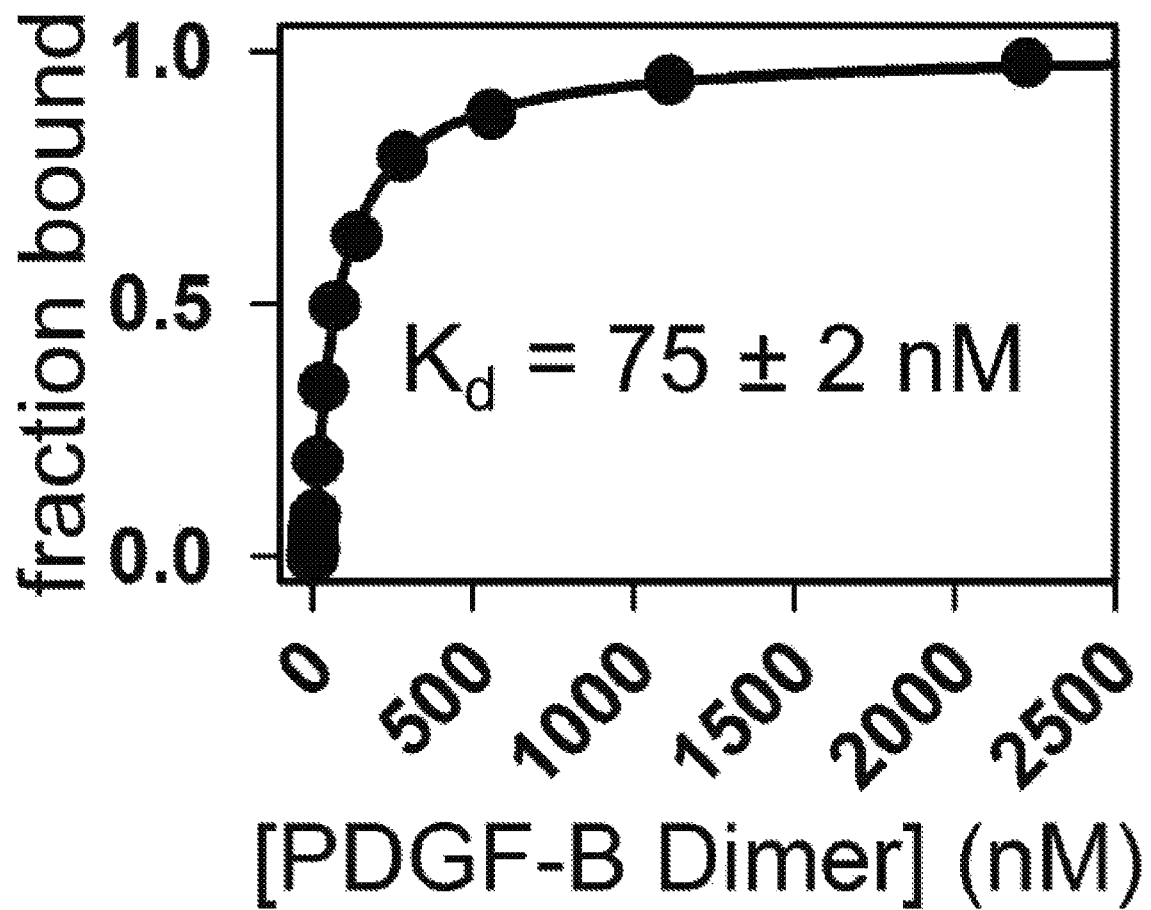
FIG. 19 shows $K_d$ determination between FITC labeled RPtag (large) h122l,a253r and unlabeled PDGF-β dimer.

A standard binding equation was used to generate the plot in FIG. 18, specifically f=y0+(ymax−y0)*(Ptot+x+Kd−sqrt((Ptot+x+Kd)^2−4*Ptot*x))/(2*Ptot), where y0 is the baseline anisotropy, ymax is the maximum anisotropy, Ptot is the fixed concentration of labeled peptide used, x is the variable concentration of protein used, and Kd is the measured Kd. The displayed result is a representative trace. Kd is mean±SEM (n=3). Purifying and refolding recombinant PDGF-β was performed as follows. Mature PDGF-β sequence lacking signaling peptide was cloned downstream of an N-terminal 8×His tag and TEV-protease site with a terminal serine such that, after cleavage, only the native PDGF-β sequence remains. The coding sequence was then subcloned into a pET 28 (+) expression plasmid and transformed into E. coli BL21(DE3) as previous and grown on LB agar with 50 μg/mL kanamycin. After overnight growth at 37° C., colonies were picked and grown in 10 L benchtop bioreactors in LB+50 μg/mL kanamycin until OD600=0.6 (800 rpm agitation, 8 SLPM air, 37° C.) and induced with 100 μM IPTG for 18 h overnight. Cells were harvested by centrifugation and re-suspended in 50 mM Tris pH 8.0, 300 mM NaCl, 10 mM beta mercaptoethanol, 10 mM imidazole and frozen at 20° C. Cells were then thawed and lysed enzymatically with a few crystals of lysozyme and DNAaseI+5 mM MgSO4 for 1 h at room temperature. Solid guanidine hydrochloride was added to the mixture to a final concentration of 6 M and the pH re-adjusted 8.0 with NaOH. Remaining cell debris was pelleted by centrifugation, and the resulting supernatant incubated with NiNTA resin (Qiagen) pre-equilibrated with the same buffer. After incubation, resin was allowed to settle, the supernatant was poured off, and the resin was washed in 20 column volumes of the same buffer. After washing, protein was eluted with the same buffer+0.5 M imidazole. The protein was then spiked with 10 mM dithiothreitol and incubated at room temperature for 1 h to help reduce any disulfide bonds. The protein was then refolded by rapid dilution into 50 mM phosphate, 150 mM NaCl pH 7.4 (10-fold dilution), and exhaustively dialyzed against the same buffer for 48 h at room temperature in the presence of 0.1 mg/mL TEV protease to cleave off the tags. A mild precipitate was removed by centrifugation and 0.2 μm filtering, and the protein further purified by a 0.15-1M NaCl gradient on a SP-sepharose column (GE), and size exclusion chromatography on a superdex S200 (prep grade column) (GE). The resultant protein was a homogenous band on SDS-PAGE, and migrated at the expected weight of the dimer when boiled without reducing agent, and monomer when boiled with 10% beta-mercaptoethanol.

Other methods are described in the text or in the figure legends.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. For example, the experiments presented herein should not be construed to limit the mutations that can be introduced into RPtag(small) or RPtag(large) to alter their binding affinity or specificity. Accordingly, the detailed description is to be regarded as illustrative in nature and not restrictive.

Below is a Table, Table 4 showing some of the sequences used in these and other examples.

TABLE 4

SEQ ID NO: 3 >
NativeRPtag(large)_with_Tags_and_
Cys (RPtag sequence proper starts
at MKEGKT . . . , all mutant
numbering in this manuscript is
done based off of this sequence
including the tags and N-terminal
Met.
MGSSCHHHHHHSQDPNSSSMKEGKTIGLVISTLNNPFEVTL
KNGAEEKAKELGYKIIVEDSQNDSSKELSNVEDLIQQKVDV
LLINPVDSDAVVTAIKEANSKNIPVITIDRSANGGDVVSHI
ASDNVKGGEMAAEFIAKALKGKGNVVELEGIPGASAARDRG TABLE 4-continued KGFDEAIAKYPDIKIVAKQAADFDRSKGLSVMENILQAQPK
IDAVFAQNDEMALGAIKAIEAANRQGIIVVGFDGTEDALKA
IKEGKMAATIAQQPALMGSLGVEMADKYLK SEQ ID NO: 4>
Nterminally tagged NativeRPtag(small)_
tagRFP
MGSSGEKIPNFIPAELKLITKENVQGSENLYFQGGSMVSKG
EELIKENMHMKLYMEGTVNNHHFKCTSEGEGKPYEGTQTMR
IKVVEGGPLPFAFDILATSFMYGSRTFINHTQGIPDFFKQS
FPEGFTWERVTTYEDGGVLTATQDTSLQDGCLIYNVKIRGV
NFPSNGPVMQKKTLGWEANTEMLYPADGGLEGRSDMALKLV
GGGHLICNFKTTYRSKKPAKNLKMPGVYYVDHRLERIKEAD
KETYVEQHEVAVARYCDLPSKLGHKLNGSSGHHHHHHHH SEQ ID NO: 5>
Nterminally_tagged_NativeRPtag(large)_
tagRFP
MGSSSQDPNSSSMKEGKTIGLVISTLNNPFFVTLKNGAEEK
AKELGYKIIVEDSQNDSSKELSNVEDLIQQKVDVLLINPVD
SDAVVTAIKEANSKNIPVITIDRSANGGDVVSHIASDNVKG
GEMAAEFIAKALKGKGNVVELEGIPGASAARDRGKGEDEAI
AKYPDIKIVAKQAADFDRSKGLSVMENILQAQPKIDAVFAQ
NDEMALGAIKAIEAANRQGIIVVGFDGTEDALKAIKEGKMA
ATIAQQPALMGSLGVEMADKYLKGSENLYFQGGSMVSKGEE
LIKENMHMKLYMEGTVNNHHFKCTSEGEGKPYEGTQTMRIK
VVEGGPLPFAFDILATSFMYGSRTFINHTQGIPDFFKQSFP
EGFTWERVTTYEDGGVLTATQDTSLQDGCLIYNVKIRGVNF
PSNGPVMQKKTLGWEANTEMLYPADGGLEGRSDMALKLVGG
GHLICNFKTTYRSKKPAKNLKMPGVYYVDHRLERIKEADKE
TYVEQHEVAVARYCDLPSKLGHKLNGSSGHHHHHHHH SEQ ID NO: 6>
Cterminally_tagged_NativeRPtag(small)_
tagRFP
MGSSHHHHHHHGSMVSKGEELIKENMHMKLYMEGTVNNHH
FKCTSEGEGKPYEGTQTMRIKVVEGGPLPFAFDILATSFMY
GSRTFINHTQGIPDFFKQSFPEGFTWERVTTYEDGGVLTAT
QDTSLQDGCLIYNVKIRGVNFPSNGPVMQKKTLGWEANTEM
LYPADGGLEGRSDMALKLVGGGHLICNFKTTYRSKKPAKNL
KMPGVYYVDHRLERIKEADKETYVEQHEVAVARYCDLPSKL
GHKLNGSSGENLYFQGGSGEKIPNFIPAELKLITKENVQGS SEQ ID NO: 7>
Cterminally_tagged_NativeRPtag(large)_
tagRFP
MGSSHHHHHHHGSMVSKGEELIKENMHMKLYMEGTVNNHH
FKCTSEGEGKPYEGTQTMRIKVVEGGPLPFAFDILATSFMY
GSRTFINHTQGIPDFFKQSFPEGFTWERVTTYEDGGVLTAT
QDTSLQDGCLIYNVKIRGVNFPSNGPVMQKKTLGWEANTEM
LYPADGGLEGRSDMALKLVGGGHLICNFKTTYRSKKPAKNL
KMPGVYYVDHRLERIKEADKETYVEQHEVAVARYCDLPSKL
GHKLNGSSGENLYFQGGSSQDPNSSSMKEGKTIGLVISTLN
NPFFVTLKNGAEEKAKELGYKIIVEDSQNDSSKELSNVEDL
IQQKVDVLLINPVDSDAVVTAIKEANSKNIPVITIDRSANG
GDVVSHIASDNVKGGEMAAEFIAKALKGKGNVVELEGIPGA
SAARDRGKGFDEAIAKYPDIKIVAKQAADFDRSKGLSVMEN
ILQAQPKIDAVFAQNDEMALGAIKAIEAANRQGIIVVGFDG
TEDALKAIKEGKMAATIAQQPALMGSLGVEMADKYLK SEQ ID NO: 8>
Nterminally_tagged_RPtag(small)Nd8,
Cd4(fast)_tagRFP
MGSSPAELKLITKGSENLYFQGGSMVSKGEELIKENMHMKL
YMEGTVNNHHFKCTSEGEGKPYEGTQTMRIKVVEGGPLPFA
FDILATSFMYGSRTFINHTQGIPDFFKQSFPEGFTWERVTT
YEDGGVLTATQDTSLQDGCLIYNVKIRGVNFPSNGPVMQKK
TLGWEANTEMLYPADGGLEGRSDMALKLVGGGHLICNFKTT
YRSKKPAKNLKMPGVYYVDHRLERIKEADKETYVEQHEVAV
ARYCDLPSKLGHKLNGSSGHHHHHHHH SEQ ID NO: 9>
Nterminally_tagged_RPtag(small)Nd2,
p5a, e18a(tight)_tagRFP
MGSSKIANFIPAELKLITKANVQGSENLYFQGGSMVSKGEE
LIKENMHMKLYMEGTVNNHHEKCTSEGEGKPYEGTQTMRIK
VVEGGPLPFAFDILATSFMYGSRTFINHTQGIPDFFKQSFP
EGFTWERVTTYEDGGVLTATQDTSLQDGCLIYNVKIRGVNF
PSNGPVMQKKTLGWEANTEMLYPADGGLEGRSDMALKLVGG TABLE 4-continued

GHLICNFKTTYRSKKPAKNLKMPGVYYVDHRLERIKEADKE
TYVEQHEVAVARYCDLPSKLGHKLNGSSGHHHHHHHH

SEQ ID NO: 10>
DualRPtagNd8, Cd4tagged_alphaTubulin
MGSPAELKLITKGGSEQKLISEEDLGGSMRECISIHVGQAG
VQIGNACWELYCLEHGIQPDGQMPSDKTIGGGDDSFNTFFS
ETGAGKHVPRAVFVDLEPTVIDEVRTGTYRQLFHPEQLITG
KEDAANNYARGHYTIGKEIIDLVLDRIRKLADQCTGLQGFL
VFHSFGGGTGSGFTSLLMERLSVDYGKKSKLEFSIYPAPQV
STAVVEPYNSILTTHTTLEHSDCAFMVDNEAIYDICRRNLD
IERPTYTNLNRLIGQIVSSITASLRFDGALNVDLTEFQTNL
VPYPRIHFPLATYAPVISAEKAYHEQLSVAEITNACFEPAN
QMVKCDPRHGKYMACCLLYRGDVVPKDVNAAIATIKTKRTI
QFVDWCPTGFKVGINYQPPTVVPGGDLAKVQRAVCMLSNTT
AIAEAWARLDHKFDLMYAKRAFVHWYVGEGMEEGEFSEARE
DMAALEKDYEEVGVDSVEGEGEEEGEEY SEQ ID NO: 11> PDGF-β
MGSSHHHHHHHHENLYFQSLGSLTIAEPAMIAECKTRTEVF
EISRRLIDRTNANFLVWPPCVEVQRCSGCCNNRNVQCRPTQ
VQLRPVQVRKIEIVRKKPIFKKATVTLEDHLACKCETVAAA
RPVT

PEPTIDES

SEQ ID NO: 12> MaturePDGF-
β_NterminalPeptide
Note: N-terminal G was to provide a
flexible attachment for the N-terminal
rhodamine to avoid interference by the
fluorophore, and is excluded from the
numbering scheme.
SEQ ID NO: 13> native
GEKIPNFIPAELKLITKENVQ
SEQ ID NO: 14> g1a
AEKIPNFIPAELKLITENVQ
SEQ ID NO: 15> e2a
GAKIPNFIPAELKLITKENVQ
SEQ ID NO: 16> k3a
GEAIPNFIPAELKLITKENVQ
SEQ ID NO: 17> i4a
GEKAPNFIPAELKLITKENVQ
SEQ ID NO: 18> p5a
GEKIANFIPAELKLITKENVQ
SEQ ID NO: 19> n6a
GEKIPAFIPAELKLITKENVQ
SEQ ID NO: 20> f7a
GEKIPNAIPAELKLITKENVQ
SEQ ID NO: 21> i8a
GEKIPNFAPAELKLITKENVQ
SEQ ID NO: 22> p9a
GEKIPNFIAELKLITKENVQ
SEQ ID NO: 23> e11a
GEKIPNFIPAALKLITKENVQ
SEQ ID NO: 24> l12a
GEKIPNFIPAEAKLITKENVQ
SEQ ID NO: 25> k13a
GEKIPNFIPAELALITKENVQ
SEQ ID NO: 26> l14a
GEKIPNFIPAELKAITKENVQ
SEQ ID NO: 27> i15a
GEKIPNFIPAELKLATKENVQ
SEQ ID NO: 28> t16a
GEKIPNFIPAELKLIAKENVQ
SEQ ID NO: 29> k17a
GEKIPNFIPAELKLITAENVQ
SEQ ID NO: 30> e18a
GEKIPNFIPAELKLITKANVQ
SEQ ID NO: 31> n19a
GEKIPNFIPAELKLITKENVQ
SEQ ID NO: 32> v20a
GEKIPNFIPAELKLITKENVQ
SEQ ID NO: 33> q21a
GEKIPNFIPAELKLITKENVQ
SEQ ID NO: 34> Nd1
EKIPNFIPAELKLITKENVQ
SEQ ID NO: 35> Nd2
KIPNFIPAELKLITKENVQ

TABLE 4-continued

| SEQ ID NO | Name | Sequence |
|---|---|---|
| 36 | Nd3 | IPNFIPAELKLITKENVQ |
| 37 | Nd4 | PNFIPAELKLITKENVQ |
| 38 | Nd5 | NFIPAELKLITKENVQ |
| 39 | Nd6 | FIPAELKLITKENVQ |
| 40 | Nd7 | IPAELKLITKENVQ |
| 41 | Nd8 | PAELKLITKENVQ |
| 42 | Nd9 | AELKLITKENVQ |
| 43 | Nd10 | ELKLITKENVQ |
| 44 | Nd11 | LKLITKENVQ |
| 45 | Nd12 | KLITKENVQ |
| 46 | Nd13 | LITKENVQ |
| 47 | Nd14 | ITKENVQ |
| 48 | Nd15 | TKENVQ |
| 49 | Nd16 | KENVQ |
| 50 | Nd17 | ENVQ |
| 51 | Cd1 | GEKIPNFIPAELKLITKENV |
| 52 | Cd2 | GEKIPNFIPAELKLITKEN |
| 53 | Cd3 | GEKIPNFIPAELKLITKE |
| 54 | Cd4 | GEKIPNFIPAELKLITK |
| 55 | Cd5 | GEKIPNFIPAELKLIT |
| 56 | Cd6 | GEKIPNFIPAELKLI |
| 57 | Cd7 | GEKIPNFIPAELKL |
| 58 | Cd8 | GEKIPNFIPAELK |
| 59 | Cd9 | GEKIPNFIPAEL |
| 60 | Cd10 | GEKIPNFIPAE |
| 61 | Cd11 | GEKIPNFIPA |
| 62 | Cd12 | GEKIPNFIP |
| 63 | Cd13 | GEKIPNFI |
| 64 | Cd14 | GEKIPNF |
| 65 | Cd15 | GEKIPN |
| 66 | Cd16 | GEKIP |
| 67 | Nd10Cd3 | ELKLITKE |
| 68 | Nd10, Cd3, e18a | ELKLITKA |
| 69 | Nd10, Cd5 | ELKLIT |
| 70 | Nd8, Cd3 | PAELKLITKE |
| 71 | Nd8, Cd3, e18a | PAELKLITKA |
| 72 | Nd8, Cd4 | PAELKLITK |
| 73 | Nd6, Cd3 | FIPAELKLITKE |
| 74 | Nd6, Cd3, e18a | FIPAELKLITKA |
| 75 | Nd6, Cd4 | FIPAELKLITK |
| 76 | Nd3, p5a, e18a | IANFIPAELKLITKANVQ |
| 77 | Nd2, Cd3 | KIPNFIPAELKLITKE |
| 78 | Nd2, Cd3, e18a | KIPNFIPAELKLITKA |
| 79 | Nd2, Cd4 | KIPNFIPAELKLITK |
| 80 | Nd2, Cd3, p5a | KIANFIPAELKLITKE |
| 81 | Nd2, Cd3, p5a, e18a | KIANFIPAELKLITKA |
| 82 | Nd2, Cd4, p5a | KIANFIPAELKLITK |
| 83 | Nd2, e18a | KIPNFIPAELKLITKANVQ |
| 84 | Nd2, p5a, e18a | KIANFIPAELKLITKANVQ |
| 85 | Nd2, k3r, p5a, e18a | RIANFIPAELKLITKANVQ |
| 86 | Nd2, k3a, p5a, e18a | AIANFIPAELKLITKANVQ |
| 87 | Nd2, k3a, p5a | AIANFIPAELKLITKENVQ |
| 88 | Nd2, e18a, v20a, v21a | KIPNFIPAELKLITKANAA |
| 89 | Nd2, p5a, e18a, v20a, q21a | KIANFIPAELKLITKANAA |
| 90 | l14k | GEKIPNFIPAELKKITKENVQ |
| 91 | NativeRPtag small for immobilization | GEKIPNFIPAELKLITKENVQGGC |
| 92 | Nd2, p5a, e18a, (tight) peptide for immobilization | KIANFIPAELKLITKANVQGGC |

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

We claim:

1. A composition comprising:
   a first protein comprising an amino acid sequence with greater than about 80% identity to RP-Tag Large (a.a. 1-257 of SEQ ID NO:94), and lacking an amino acid sequence with greater than about 80% identity to RP-Tag Small (a.a. 258-278 of SEQ ID NO:94), and
   a second protein comprising an amino acid sequence with greater than about 80% identity to the RP-Tag Small, and lacking an amino acid sequence with greater than about 80% identity to the RP-Tag Large, wherein the first and second protein are not covalently connected.

2. The composition of claim 1, wherein the second protein is a fusion protein comprising a third protein sequence.

3. The composition of claim 1, further comprising a selectable or detectable molecule or tag, selected from a fluorophore, a peroxidase, biotin, radioactive isotopes, chromophores, gold, iron, quantum dots or combinations thereof, wherein the tag is covalently attached to the first or second protein.

4. The composition of claim 1, further comprising a salt, a pH Buffer, or a combination thereof.

5. The composition of claim 1, wherein the first protein is less than about forty amino acids, and covalently fused to a fusion protein comprising a third protein sequence.

6. A nucleic acid encoding the second protein of claim 5, wherein the nucleic acid is part of a vector.

7. The nucleic acid of claim 6, wherein the nucleic acid is part of an expression vector.

8. The nucleic acid of claim 7, wherein the nucleic acid includes an inducible gene promoter.

9. A cell comprising the composition of claim 1.

10. A kit comprising:
    the composition of claim 1; and
    instructions for their use.

11. A method of detecting a target protein, comprising:
    expressing a fusion protein comprising the first protein of the composition of claim 1 and the target protein to create a first composition;
    expressing a second protein comprising an amino acid sequence with greater than about 80% identity to the RP-Tag Large, and lacking an amino acid sequence with greater than about 80% identity to the RP-Tag Small to create a second composition;

combining the first composition comprising the fusion protein and the second composition;

allowing the first protein to bind the second protein to create a protein complex; and detecting the protein complex.

12. The method of claim 11, wherein the second protein is conjugated, or immobilized to solid support.

13. The method of claim 11, wherein the method includes quantification of the target protein.

14. The method of claim 11, wherein detection is by one or more of western blot, pull down assays, gel retardation assays, enzyme linked immunosorbant assays, surface plasmon resonance chips, biolayer interferometry chips, immunohistochemistry, immunocytochemistry, fluorescence microscopy, electron microscopy, flow cytometry, fluorescence activated cell sorting, and tagged cell purification.

* * * * *

UNITED STATES PATENT AND TRADEMARK OFFICE
CERTIFICATE OF CORRECTION

| | |
|---|---|
| PATENT NO. | : 11,414,454 B2 |
| APPLICATION NO. | : 16/492038 |
| DATED | : August 16, 2022 |
| INVENTOR(S) | : Adam Blanden and Aaron Wolfe |

It is certified that error appears in the above-identified patent and that said Letters Patent is hereby corrected as shown below:

On the Title Page

Item (71) Applicant and item (73) Assignee sections read:
"Auctus Biologies, Inc."
Should be:
--Auctus Biologics, Inc.--

In the Specification

At Column 19, Line 40 reads:
""Nd8Cd4)""
Should be:
--"Nd8Cd4)" SEQ ID No: 72--

At Column 19, Line 43 reads:
""Nd2p5ae18a""
Should be:
--"Nd2p5ae18a" SEQ ID No: 84--

At Column 24, Line 60 reads:
"AIKEGKMAATIAQQPALMGSLGVEMADYLK."
Should be:
--AIKEGKMAATIAQQPALMGSLGVEMADYLK SEQ ID No. 3.--

At Column 28, Lines 28-29 reads:
"numbering scheme. SEQ ID No: 13> native"
Should be:
--numbering scheme. GSLGSLTIAEPAMIAE SEQ ID No: 13> native--

Signed and Sealed this
Sixteenth Day of May, 2023

Katherine Kelly Vidal
*Director of the United States Patent and Trademark Office*